US010077477B2

(12) United States Patent
Zhang et al.

(10) Patent No.: US 10,077,477 B2
(45) Date of Patent: Sep. 18, 2018

(54) SERUM/PLASMA MICRORNAS AND USES THEREOF

(71) Applicant: JIANGSU MINGMA BIOTECH CO., LTD., Taizhou (CN)

(72) Inventors: Chenyu Zhang, Nanjing (CN); Junfeng Zhang, Nanjing (CN); Xi Chen, Hoover, AL (US); Yi Ba, Tianjin (CN); Jiangning Chen, Jiangsu (CN); Jin Wang, Jiangsu (CN); Ke Zeng, Jiangsu (CN); Hongjie Zhang, Jiangsu (CN)

(73) Assignee: JIANGSU MINGMA BIOTECH CO., LTD., Taizhou (CN)

( * ) Notice: Subject to any disclaimer, the term of this patent is extended or adjusted under 35 U.S.C. 154(b) by 0 days.

(21) Appl. No.: 14/144,127

(22) Filed: Dec. 30, 2013

(65) Prior Publication Data

US 2014/0121133 A1    May 1, 2014

Related U.S. Application Data

(62) Division of application No. 12/302,196, filed as application No. PCT/CN2007/003463 on Dec. 6, 2007, now abandoned.

(30) Foreign Application Priority Data

Nov. 2, 2007  (CN) .......................... 2007 1 0134620

(51) Int. Cl.
*C12Q 1/68*     (2018.01)
*C12Q 1/6886*   (2018.01)
(Continued)

(52) U.S. Cl.
CPC .......... *C12Q 1/6886* (2013.01); *C12Q 1/6809* (2013.01); *C12Q 1/6876* (2013.01);
(Continued)

(58) Field of Classification Search
USPC ........ 435/6.11, 91.1, 6.1, 6.12, 91.31, 287.2, 435/91.312, 87.2; 536/23.1, 24.5, 24;
(Continued)

(56) References Cited

U.S. PATENT DOCUMENTS

| 2008/0200416 | A1* | 8/2008 | Li | C12N 15/113 514/44 A |
| 2009/0004668 | A1  | 1/2009 | Chen et al. | |
| 2009/0010908 | A1* | 1/2009 | Gow et al. | 424/94.1 |
| 2009/0239818 | A1* | 9/2009 | Cheng | 514/52 |
| 2010/0099746 | A1* | 4/2010 | Yamada | C12N 15/113 514/44 R |
| 2010/0298151 | A1* | 11/2010 | Taylor et al. | 506/2 |
| 2010/0305188 | A1* | 12/2010 | Nakano | A61K 31/7088 514/44 A |
| 2012/0288476 | A1* | 11/2012 | Hartmann | A61K 31/7105 424/85.4 |
| 2012/0321647 | A1* | 12/2012 | Breaker | C12N 15/115 424/178.1 |
| 2012/0322109 | A1* | 12/2012 | Shuman | C07H 21/02 435/91.2 |

(Continued)

OTHER PUBLICATIONS

Kruhoffer et al, J. Molecular Diagnostics, vol. 9, No. 4, pp. 452-458 (2007).*

(Continued)

*Primary Examiner* — Jane Zara
(74) *Attorney, Agent, or Firm* — Hamre, Schumann, Mueller & Larson, P.C.

(57) ABSTRACT

This invention provides a combination of microRNAs for evaluating the physiological and/or pathological condition of a subject, wherein the combination comprises all detectable microRNAs stably existing in the serum/plasma of a subject; and a method for evaluating the physiological and/or pathological condition of a subject, wherein the method includes determining all detectable microRNAs stably existing in the serum/plasma of a subject; and a kit for evaluating the physiological and/or pathological condition of a subject, wherein the kit contains the tools for determining all detectable microRNAs that stably existing in the serum/plasma of a subject; and a biochip for evaluating the physiological and/or pathological condition of a subject, wherein the biochip contains the components for determining all detectable microRNAs stably existing in the serum/plasma of a subject. The aforementioned combination, method, kit and biochip can be used for diagnosis as well as differentially diagnosis of diseases including various tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary system, diseases of reproductive system and diseases of locomotor system, prediction of complications occurrence and malignant diseases relapse, evaluation of therapeutic effects, screening of pharmaceutical active ingredients, assessment of drug efficacy as well as forensic authentication and prohibited drug inspection and the like, possessing a number of advantages such as extensive detection spectrum, high sensitivity, low cost, convenience for sampling, ease for sample preservation, etc. The said method can be widely used in work related to general survey of diseases and so on, improve the low-specificity and low-sensitivity caused by individual differences which single markers are difficult to overcome, significantly increasing the clinical detection rate of diseases, all of which make it become an effective means for diagnosing diseases in an early phase.

16 Claims, 4 Drawing Sheets

Specification includes a Sequence Listing.

(51) Int. Cl.
 C12Q 1/6809 (2018.01)
 C12Q 1/6883 (2018.01)
 C12Q 1/6876 (2018.01)
(52) U.S. Cl.
 CPC ..... *C12Q 1/6883* (2013.01); *C12Q 2600/158* (2013.01); *C12Q 2600/178* (2013.01)
(58) Field of Classification Search
 USPC .............................. 514/44; 424/9.1; 506/16
 See application file for complete search history.

(56) References Cited

U.S. PATENT DOCUMENTS

2013/0029874 A1* 1/2013 Mambo ................ C12Q 1/6886 506/9
2013/0184175 A1* 7/2013 Beaudenon-Huibregtse ............... C12Q 1/6886 506/9

OTHER PUBLICATIONS

Calin et al, Cancer Research, vol. 66, No. 15, pp. 7390-7394 (2006).*
Vigneault et al, Nature Methods, vol. 5, No. 9, pp. 777-779 (2008).*
Aravin et al, FEBS Letter, vol. 579, No. 26, pp. 5830-5840 (2005).*
Kruhoffer et al., J. Molecular Diagnostics, vol. 9, No. 4, pp. 452-458 (2007).
Galin et al., Cancer Res., vol. 66, No. 15, pp. 7390-7394 (2006).
Opalinska et al., Nature Rev., vol. 1, pp. 503-514 (2002).
Doench et al., Genes and Development, vol. 18, No. 5, pp. 504-511 (2004).
Alberts, et al., "Molecular Biology of the Cell," 4th ed.
Bartel, D.P., "MicroRNAs: Genomics, Biogenesis, Mechanism, and Function," Cell, 2004, vol. 116, pp. 281-297.
Furukawa, N., et al., "Optimization of a microRNA expression vector for function analysis of microRNA," J. of Controlled Release, 2011, vol. 150, pp. 94-101.
He, L., et al., "MicroRNAs: Small RNAs with a Big Role in Gene Regulation," Nature, 2004, vol. 5, pp. 522-532.
Houseley, J., et al., "The Many Pathways of RNA Degradation," Cell, 2009, vol. 136, pp. 763-776.
Kottel, R. H., et al., "Serum Ribonuclease Activity in Cancer Patients," Br. J. Cancer, 1978, vol. 38, pp. 280-286.
Nilsen, T. W., "Mechanisms of microRNA-mediated gene regulation in animal cells," TRENDS in Genetics, 2007, vol. 23, No. 5, pp. 243-249.
Pillai, R. S., "MicroRNA function: Multiple mechanisms for a tiny RNA?" RNA, 2005, vol. 11, pp. 1753-1761.
Reddi, K. K., et al., "Elevated serum ribonuclease in patients with pancreatic cancer," Pro. Natl. Acad. Sci. USA, 1976, vol. 73, No. 7, pp. 2308-2310.
Berg, J. M., et al., "8.3.2. The Active Sites of Enzymes Have Some Common Features," Biochemistry, 5th ed., W. H. Freeman and Company. (2002).
Stansfield, W. D., "Molecular Genetics," Theory and Problems of Genetics, 3rd ed., Schaum's Outline Series, McGraw-Hill, p. 356. (Oct. 1, 1991).
Steeg, et al., "2. Secondary Structure of RNA: Its Importance and Methods of Determination," Artificial Intelligence and Molecular Biology, p. 123. (1993).
Turksen, "Methods in Molecular Biology," Embryonic Stem Cells, Methods and Protocols, vol. 185, Humana Press, pp. 137-138; (2002).

* cited by examiner

SERUM/PLASMA MICRORNAS AND USES THEREOF

REFERENCE OF RELATED APPLICATIONS

The present application is a divisional application of U.S. application Ser. No. 12/302,196 titled SERUM/PLASMA MICRORNAS AND USES THEREOF, which was filed on Nov. 24, 2008, and the entire contents of which are incorporated by reference herein.

SUBMISSION OF SEQUENCE LISTING

The Sequence Listing associated with this application is filed in electronic format via EFS-Web and hereby incorporated by reference into the specification in its entirety. The name of the text filecontaining the Sequence Listing is Sequence_Listing_15454_00029. The size of the text file is 84 KB, and the text file was created on Dec. 30, 2013.

TECHNICAL FIELD

The present invention relates to microRNAs and uses thereof, more specifically, to serum/plasma microRNAs and the uses of serum/plasma microRNAs for diagnosis and differential diagnosis of diseases, prediction of complication occurrence and malignant disease relapse, evaluation of therapeutic effects, screening of pharmaceutical active ingredients, assessment of drug efficacy, forensic authentication and prohibited drug inspection and the like.

BACKGROUND ART

To locate and precisely detect disease markers has already been the important precondition for the diagnosis and treatment of various clinical diseases including various tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary system, diseases of reproductive system and diseases of locomotor system. Although more and more disease markers have been found and utilized in general survey and diagnosis of clinical diseases as well as monitoring and controlling of therapeutic effects, their clinical application effects are obviously insufficient. For instance, tumor marker, e.g. alphafetoprotein, lactic dehydrogenase and carcinoembryonic antigen have been widely used in clinic. But these disease markers are far from meeting the needs of early diagnosis for cancer for the following two main reasons: (1) the sensitivity and specificity for the above-mentioned disease markers are relatively low, thus their detection results cannot be used as a diagnostic indicator of disease; (2) the early diagnosis rate of disease shall be positively correlative with the therapeutic effects. However, it is difficult for any of the aforesaid disease markers to meet such requirements for early diagnosis. Take cancer for example, the specificity of tumor differentiation is too high, the integrated sensitivity of tumor is relatively low, the samples sent to be detected are difficult to be repeatedly taken and the conditions to meet the preservation requirements for samples are too exacting, meanwhile, the cost is very high, thus under existing technology the spreading and use of the tumor markers available are hard to realize. The inherent defects of some traditional medical means such as biopsy, for example, incorrect material-extraction position, the inadequacy of sample materials for histocytes and human inexperience, etc., will all lead to misdiagnosis. Although other techniques such as imaging technique have been widely used for examination and diagnosis of diseases, there exists considerable limitation on the determination for disease degree. Consequently, it is very necessary to find out a maker for disease detection which is novel, sensitive and convenient to use and can also overcome the defects of existing markers as mentioned above.

MicroRNAs are defined as a kind of non-coding single-stranded small RNA molecules of approximately from 19 to 23 nucleotides in length. They are highly conservative in evolution; and are closely related to many normal physiological activities of animals such as development process, tissue differentiation, cell apoptosis and energy metabolism; in addition, bear close relation with the occurrence and development of many diseases. Recent studies show that the expression levels of several microRNAs in chronic lymphocytic leukemia and Burkitt lymphoma are on average down-regulated to various extents; and that by analyzing and comparing the expressions of microRNAs in tissues of human lung cancer and human breast cancer, the expression levels of several tissue specific microRNAs have changed relative to normal tissues. Some studies demonstrate that microRNAs affect the occurrence and development of cardio-cerebrovascular diseases such as myocardial hypertrophy, heart failure, atherosclerosis, and are closely relative to metabolic diseases such as Diabetes II. These experimental results indicate that there exists inevitable connection between the expression and specificity changes of microRNAs and the occurrence and development of diseases.

For the unimaginable important role microRNAs played in the regulation of expression after gene transcription, microRNAs have some associations with diseases. First of all, the changes of microRNAs may be the cause of diseases. This is because both the inhibitor and the promoter of diseases may be target sites for microRNAs. If the expression of microRNA itself is disturbed, e.g., the expression level of microRNA which is originally to inhibit disease promoters decreases or the expression level of microRNA which is to inhibit disease inhibitor increases, its end results will both lead to changes in the expression of downstream genes and the overall disorder of some pathways, further inducing the occurrence of diseases. Secondly, the changes of microRNAs may also result from diseases. This is because, when a kind of disease such as cancer occurs, it will lead to the loss of chromosome segments, gene mutation or rapid amplification of chromosome segments; moreover, if the microRNAs happen to locate in the changing segment, then their expression level will extremely significantly change. Therefore, in theory, microRNAs can be completely regarded as a kind of new disease markers, the specificity changes of which inevitably correlate with the occurrence and development of diseases. Meanwhile, microRNA can also be used as a potential drug target, and it may greatly alleviate the occurrence and development of diseases by inhibiting the up-regulated microRNAs and overexpressedly down-regulated microRNAs in the course of a disease.

The inventor has carried out the research in the relevant fields of using microRNAs as disease markers, for instance, choosing colonic carcinoma which ranks forth in the incidence of malignant tumor as the research object. The research suggests that, during the process of colon benign polyps developing into malignant tumor, some microRNAs exhibit specificity changes, thereby a more sensitive and accurate method for the early diagnosis of colonic carcinoma having been set up through detecting the specific changes in microRNAs. However, since the sampling for tissue specimen is not easy, the wide application of this method in clinics is limited.

DETAILED DESCRIPTION OF THE INVENTION

The inventor focuses the research on the blood which is relatively easy to obtain and even can be collected via routine physical examination. Blood will circulate to all tissues in body and convey nutrients to cells whilst scavenging waste materials; therefore, blood is able to reflect the physiological pathology of the whole organism and its detection results is an indicator of human health. It is known that in serum/plasma there are many kinds of proteins such as total protein, albumin and globulin, many kinds of lipids such as HDL cholesterol and triglycerides, many kinds of carbohydrates, pigments, electrolytes, inorganic salts, and many kinds of enzymes such as amylase, alkaline phosphatase, acid phosphatase, cholinesterase and aldolase; moreover, there also exist many kinds of signaling molecules such as cytokines and hormone from tissues and organs in whole body. Currently, disease diagnosis is only limited to the above-mentioned biochemical indexes in serum/plasma, and no report is available regarding microRNAs in serum/plasma. It traditionally believed that there is no microRNA in serum/plasma, and that, if any, it will be rapidly degraded by RNase into small molecule segments and hence cannot be detected. However, microRNAs, consisting of from 19 to 23 nucleotides, possess specificity and relative stability in structure and hence are very likely present in serum/plasma. Meanwhile, since microRNAs are a new type of disease markers, it is anticipated that by studying whether or not microRNAs are present in serum/plasma, whether or not they can be detected and the connection between microRNAs and diseases, a new technology is established for the early disease diagnosis, disease identification as well as monitoring and controlling of course of diseases, prediction of malignant disease relapse and prognosis and complication occurrence, assessment of drug efficacy, guide of medication, individualized treatment, screening of active ingredients of Chinese Traditional Medicines, population taxonomy, etc., by use of the microRNAs stably existing in serum/plasma as well as their specificity changes.

The present invention provides a combination of microRNAs for evaluating physiological and/or pathological condition in a subject, wherein the combination comprises all detectable microRNAs stably existing in the serum/plasma of the subject.

The present invention further provides a method for evaluating physiological and/or pathological condition in a subject, wherein the method comprises determining all detectable microRNAs stably existing in the serum/plasma of the subject.

In the above-mentioned combination or method, all detectable microRNAs stably existing in serum/plasma of a subject may be all mature microRNAs in human serum/plasma, specifically include let-7a, let-7b, let-7c, let-7d, let-7e, let-7f, let-7g, let-7i, miR-1, miR-100, miR-101, miR-103, miR-105, miR-106a, miR-106b, miR-107, miR-10a, miR-10b, miR-122a, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-142-5p, miR-143, miR-144, miR-145, miR-146a, miR-146b, miR-147, miR-148a, miR-148b, miR-149, miR-150, miR-151, miR-152, miR-153, miR-154, miR-154*, miR-155, miR-15a, miR-15b, miR-16, miR-17-3p, miR-17-5p, miR-181a, miR-181b, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193a, miR-193b, miR-194, miR-195, miR-196a, miR-196b, miR-197, miR-198, miR-199a, miR-199a*, miR-199b, miR-19a, miR-19b, miR-200a, miR-200a*, miR-200b, miR-200c, miR-202, miR-202*, miR-203, miR-204, miR-205, miR-206, miR-208, miR-20a, miR-20b, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-483, miR-484, miR-485-3p, miR-485-5p, miR-486, miR-487a, miR-487b, miR-488, miR-489, miR-490, miR-491, miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548th miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591, miR-592, miR-593, miR-594, miR-595, miR-596, miR-597, miR-598, miR-599, miR-600, miR-601, miR-602, miR-603, miR-604, miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-7, miR-9, miR-9*, miR-92, miR-93, miR-95, miR-96, miR-98, miR-99 and miR-99b.

The aforesaid method for determining all detectable microRNAs stably existing in serum/plasma of a subject is one or more selected from the group consisting of RT-PCR method, Real-time PCR method, Northern blotting method, RNase protection assay, Solexa sequencing technology and biochip method.

The aforesaid RT-PCR method includes the following steps:

(1) extracting the total RNA from the serum/plasma of a subject and obtaining cDNA samples by RNA reverse transcription reaction; or collecting serum/plasma samples from the subject and conducting reverse transcription reaction with serum/plasma being a buffer so as to prepare cDNA samples;

(2) designing a primer by use of microRNAs and conducting PCR reaction;

(3) conducting agarose gel electrophoresis of PCR products;

(4) observing agarose gel under ultraviolet lamp after EB staining.

The aforesaid real-time PCR method includes the following steps:

(1) extracting the total RNA from the serum/plasma of a subject and obtaining cDNA samples by RNA reverse transcription reaction; or collecting serum/plasma samples from the subject and conducting reverse transcription reaction with serum/plasma being a buffer so as to prepare cDNA samples;

(2) designing a primer by use of microRNAs;

(3) adding a fluorescent probe to conduct PCR reaction;

(4) detecting and comparing the variation in levels of microRNAs in the serum/plasma relative to those of microRNAs in normal serum/plasma.

The present invention further provides a kit for evaluating physiological and/or pathological condition of a subject, wherein the kit comprises the tools for determining all detectable microRNAs stably existing in the serum/plasma of the subject. The kit may comprises the primers of all mature microRNAs in human serum/plasma, specifically comprises the primers of let-7a, let-7b, let-7c, let-7d, let-7e, let-7f, let-7g, let-7i, miR-1, miR-100, miR-101, miR-103, miR-105, miR-106a, miR-106b, miR-107, miR-10a, miR-10b, miR-122a, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-142-5p, miR-143, miR-144, miR-145, miR-146a, miR-146b, miR-147, miR-148a, miR-148b, miR-149, miR-150, miR-151, miR-152, miR-153, miR-154, miR-154*, miR-155, miR-15a, miR-15b, miR-16, miR-17-3p, miR-17-5p, miR-181a, miR-181b, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193a, miR-193b, miR-194, miR-195, miR-196a, miR-196b, miR-197, miR-198, miR-199a, miR-199a*, miR-199b, miR-19a, miR-19b, miR-200a, miR-200a*, miR-200b, miR-200c, miR-202, miR-202*, miR-203, miR-204, miR-205, miR-206, miR-208, miR-20a, miR-20b, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-483, miR-484, miR-485-3p, miR-485-5p, miR-486, miR-487a, miR-487b, miR-488, miR-489, miR-490, miR-491, miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548th miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591, miR-592, miR-593, miR-594, miR-595, miR-596, miR-597, miR-598, miR-599, miR-600, miR-601, miR-602, miR-603, miR-604, miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-7, miR-9, miR-9*, miR-92, miR-93, miR-95, miR-96, miR-98, miR-99a and miR-99b.

The present invention also provides a biochip for evaluating physiological and/or pathological condition of a subject, wherein the biochip contains the components for determining all detectable microRNAs stably existing in the serum/plasma of the subject. The biochip may also contain the probes for all mature microRNAs in human serum/plasma. The probes specifically include the probes as shown in Table 1.

TABLE 1

Probes of all mature microRNAs in human serum/plasma

| SEQ ID NO | Probes | Corresponding microRNAs | Sequences of probes |
|---|---|---|---|
| SEQ ID NO: 001 | probe-let-7a | let-7a | AACTATACAACCTACTACCTCA |
| SEQ ID NO: 002 | probe-let-7b | let-7b | AACCACACAACCTACTACCTCA |
| SEQ ID NO: 003 | probe-let-7c | let-7c | AACCATACAACCTACTACCTCA |
| SEQ ID NO: 004 | probe-let-7d | let-7d | ACTATGCAACCTACTACCTCT |
| SEQ ID NO: 005 | probe-let-7e | let-7e | ACTATACAACCTCCTACCTCA |
| SEQ ID NO: 006 | probe-let-7f | let-7f | AACTATACAATCTACTACCTCA |
| SEQ ID NO: 007 | probe-let-7g | let-7g | ACTGTACAAACTACTACCTCA |
| SEQ ID NO: 008 | probe-let-7i | let-7i | ACAGCACAAACTACTACCTCA |
| SEQ ID NO: 009 | probe-miR-1 | miR-1 | TACATACTTCTTTACATTCCA |
| SEQ ID NO: 010 | probe-miR-100 | miR-100 | CACAAGTTCGGATCTACGGGTT |
| SEQ ID NO: 011 | probe-miR-101 | miR-101 | CTTCAGTTATCACAGTACTGTA |
| SEQ ID NO: 012 | probe-miR-103 | miR-103 | TCATAGCCCTGTACAATGCTGCT |
| SEQ ID NO: 013 | probe-miR-105 | miR-105 | ACAGGAGTCTGAGCATTTGA |
| SEQ ID NO: 014 | probe-miR-106a | miR-106a | GCTACCTGCACTGTAAGCACTTTT |
| SEQ ID NO: 015 | probe-miR-106b | miR-106b | ATCTGCACTGTCAGCACTTTA |
| SEQ ID NO: 016 | probe-miR-107 | miR-107 | TGATAGCCCTGTACAATGCTGCT |
| SEQ ID NO: 017 | probe-miR-10a | miR-10a | CACAAATTCGGATCTACAGGGTA |
| SEQ ID NO: 018 | probe-miR-10b | miR-10b | ACAAATTCGGTTCTACAGGGTA |
| SEQ ID NO: 019 | probe-miR-122a | miR-122a | ACAAACACCATTGTCACACTCCA |

TABLE 1-continued

Probes of all mature microRNAs in human serum/plasma

| SEQ ID NO | Probes | Corresponding microRNAs | Sequences of probes |
|---|---|---|---|
| SEQ ID NO: 020 | probe-miR-124a | miR-124a | TGGCATTCACCGCGTGCCTTAA |
| SEQ ID NO: 021 | probe-miR-125a | miR-125a | CACAGGTTAAAGGGTCTCAGGGA |
| SEQ ID NO: 022 | probe-miR-125b | miR-125b | TCACAAGTTAGGGTCTCAGGGA |
| SEQ ID NO: 023 | probe-miR-126 | miR-126 | GCATTATTACTCACGGTACGA |
| SEQ ID NO: 024 | probe-miR-126* | miR-126* | CGCGTACCAAAAGTAATAATG |
| SEQ ID NO: 025 | probe-miR-127 | miR-127 | AGCCAAGCTCAGACGGATCCGA |
| SEQ ID NO: 026 | probe-miR-128a | miR-128a | AAAAGAGACCGGTTCACTGTGA |
| SEQ ID NO: 027 | probe-miR-128b | miR-128b | GAAAGAGACCGGTTCACTGTGA |
| SEQ ID NO: 028 | probe-miR-129 | miR-129 | GCAAGCCCAGACCGCAAAAAG |
| SEQ ID NO: 029 | probe-miR-130a | miR-130a | ATGCCCTTTTAACATTGCACTG |
| SEQ ID NO: 030 | probe-miR-130b | miR-130b | ATGCCCTTTCATCATTGCACTG |
| SEQ ID NO: 031 | probe-miR-132 | miR-132 | CGACCATGGCTGTAGACTGTTA |
| SEQ ID NO: 032 | probe-miR-133a | miR-133a | ACAGCTGGTTGAAGGGGACCAA |
| SEQ ID NO: 033 | probe-miR-133b | miR-133b | TAGCTGGTTGAAGGGGACCAA |
| SEQ ID NO: 034 | probe-miR-134 | miR-134 | CCCTCTGGTCAACCAGTCACA |
| SEQ ID NO: 035 | probe-miR-135a | miR-135a | TCACATAGGAATAAAAAGCCATA |
| SEQ ID NO: 036 | probe-miR-135b | miR-135b | CACATAGGAATGAAAAGCCATA |
| SEQ ID NO: 037 | probe-miR-136 | miR-136 | TCCATCATCAAAACAAATGGAGT |
| SEQ ID NO: 038 | probe-miR-137 | miR-137 | CTACGCGTATTCTTAAGCAATA |

TABLE 1-continued

Probes of all mature microRNAs in human serum/plasma

| SEQ ID NO | Probes | Corresponding microRNAs | Sequences of probes |
|---|---|---|---|
| SEQ ID NO: 039 | probe-miR-138 | miR-138 | GATTCACAACACCAGCT |
| SEQ ID NO: 040 | probe-miR-139 | miR-139 | AGACACGTGCACTGTAGA |
| SEQ ID NO: 041 | probe-miR-140 | miR-140 | CTACCATAGGGTAAAACCACT |
| SEQ ID NO: 042 | probe-miR-141 | miR-141 | CCATCTTTACCAGACAGTGTTA |
| SEQ ID NO: 043 | probe-miR-142-3p | miR-142-3p | TCCATAAAGTAGGAAACACTACA |
| SEQ ID NO: 044 | probe-miR-142-5p | miR-142-5p | GTAGTGCTTTCTACTTTATG |
| SEQ ID NO: 045 | probe-miR-143 | miR-143 | TGAGCTACAGTGCTTCATCTCA |
| SEQ ID NO: 046 | probe-miR-144 | miR-144 | CTAGTACATCATCTATACTGTA |
| SEQ ID NO: 047 | probe-miR-145 | miR-145 | AAGGGATTCCTGGGAAAACTGGAC |
| SEQ ID NO: 048 | probe-miR-146a | miR-146a | AACCCATGGAATTCAGTTCTCA |
| SEQ ID NO: 049 | probe-miR-146b | miR-146b | AGCCTATGGAATTCAGTTCTCA |
| SEQ ID NO: 050 | probe-miR-147 | miR-147 | GCAGAAGCATTTCCACACAC |
| SEQ ID NO: 051 | probe-miR-148a | miR-148a | ACAAAGTTCTGTAGTGCACTGA |
| SEQ ID NO: 052 | probe-miR-148b | miR-148b | ACAAAGTTCTGTGATGCACTGA |
| SEQ ID NO: 053 | probe-miR-149 | miR-149 | GGAGTGAAGACACGGAGCCAGA |
| SEQ ID NO: 054 | probe-miR-150 | miR-150 | CACTGGTACAAGGGTTGGGAGA |
| SEQ ID NO: 055 | probe-miR-151 | miR-151 | CCTCAAGGAGCTTCAGTCTAGT |
| SEQ ID NO: 056 | probe-miR-152 | miR-152 | CCCAAGTTCTGTCATGCACTGA |
| SEQ ID NO: 057 | probe-miR-153 | miR-153 | TCACTTTTGTGACTATGCAA |

TABLE 1-continued

Probes of all mature microRNAs in human serum/plasma

| SEQ ID NO | Probes | Corresponding microRNAs | Sequences of probes |
|---|---|---|---|
| SEQ ID NO: 058 | probe-miR-154 | miR-154 | CGAAGGCAACACGGATAACCTA |
| SEQ ID NO: 059 | probe-miR-154* | miR-154* | AATAGGTCAACCGTGTATGATT |
| SEQ ID NO: 060 | probe-miR-155 | miR-155 | CCCCTATCACGATTAGCATTAA |
| SEQ ID NO: 061 | probe-miR-15a | miR-15a | CACAAACCATTATGTGCTGCTA |
| SEQ ID NO: 062 | probe-miR-15b | miR-15b | TGTAAACCATGATGTGCTGCTA |
| SEQ ID NO: 063 | probe-miR-16 | miR-16 | CGCCAATATTTACGTGCTGCTA |
| SEQ ID NO: 064 | probe-miR-17-3p | miR-17-3p | ACAAGTGCCTTCACTGCAGT |
| SEQ ID NO: 065 | probe-miR-17-5p | miR-17-5p | ACTACCTGCACTGTAAGCACTTTG |
| SEQ ID NO: 066 | probe-miR-181a | miR-181a | ACTCACCGACAGCGTTGAATGTT |
| SEQ ID NO: 067 | probe-miR-181b | miR-181b | CCCACCGACAGCAATGAATGTT |
| SEQ ID NO: 068 | probe-miR-181c | miR-181c | ACTCACCGACAGGTTGAATGTT |
| SEQ ID NO: 069 | probe-miR-181d | miR-181d | AACCCACCGACAACAATGAATGTT |
| SEQ ID NO: 070 | probe-miR-182 | miR-182 | TGTGAGTTCTACCATTGCCAAA |
| SEQ ID NO: 071 | probe-miR-182* | miR-182* | TAGTTGGCAAGTCTAGAACCA |
| SEQ ID NO: 072 | probe-miR-183 | miR-183 | CAGTGAATTCTACCAGTGCCATA |
| SEQ ID NO: 073 | probe-miR-184 | miR-184 | ACCCTTATCAGTTCTCCGTCCA |
| SEQ ID NO: 074 | probe-miR-185 | miR-185 | GAACTGCCTTTCTCTCCA |
| SEQ ID NO: 075 | probe-miR-186 | miR-186 | AAGCCCAAAAGGAGAATTCTTTG |
| SEQ ID NO: 076 | probe-miR-187 | miR-187 | CGGCTGCAACACAAGACACGA |

TABLE 1-continued

Probes of all mature microRNAs in human serum/plasma

| SEQ ID NO | Probes | Corresponding microRNAs | Sequences of probes |
|---|---|---|---|
| SEQ ID NO: 077 | probe-miR-188 | miR-188 | ACCCTCCACCATGCAAGGGATG |
| SEQ ID NO: 078 | probe-miR-189 | miR-189 | ACTGATATCAGCTCAGTAGGCAC |
| SEQ ID NO: 079 | probe-miR-18a | miR-18a | TATCTGCACTAGATGCACCTTA |
| SEQ ID NO: 080 | probe-miR-18a* | miR-18a* | AGAAGGAGCACTTAGGGCAGT |
| SEQ ID NO: 081 | probe-miR-18b | miR-18b | TAACTGCACTAGATGCACCTTA |
| SEQ ID NO: 082 | probe-miR-190 | miR-190 | ACCTAATATATCAAACATATCA |
| SEQ ID NO: 083 | probe-miR-191 | miR-191 | AGCTGCTTTTGGGATTCCGTTG |
| SEQ ID NO: 084 | probe-miR-191* | miR-191* | GGGGACGAAATCCAAGCGCAGC |
| SEQ ID NO: 085 | probe-miR-192 | miR-192 | GGCTGTCAATTCATAGGTCAG |
| SEQ ID NO: 086 | probe-miR-193a | miR-193a | CTGGGACTTTGTAGGCCAGTT |
| SEQ ID NO: 087 | probe-miR-193b | miR-193b | AAAGCGGGACTTTGAGGGCCAGTT |
| SEQ ID NO: 088 | probe-miR-194 | miR-194 | TCCACATGGAGTTGCTGTTACA |
| SEQ ID NO: 089 | probe-miR-195 | miR-195 | GCCAATATTTCTGTGCTGCTA |
| SEQ ID NO: 090 | probe-miR-196a | miR-196a | CCAACAACATGAAACTACCTA |
| SEQ ID NO: 091 | probe-miR-196b | miR-196b | CCAACAACAGGAAACTACCTA |
| SEQ ID NO: 092 | probe-miR-197 | miR-197 | GCTGGGTGGAGAAGGTGGTGAA |
| SEQ ID NO: 093 | probe-miR-198 | miR-198 | CCTATCTCCCCTCTGGACC |
| SEQ ID NO: 094 | probe-miR-199a | miR-199a | GAACAGGTAGTCTGAACACTGGG |
| SEQ ID NO: 095 | probe-miR-199a* | miR-199a* | AACCAATGTGCAGACTACTGTA |

TABLE 1-continued

Probes of all mature microRNAs in human serum/plasma

| SEQ ID NO | Probes | Corresponding microRNAs | Sequences of probes |
|---|---|---|---|
| SEQ ID NO: 096 | probe-miR-199b | miR-199b | GAACAGATAGTCTAAACACTGGG |
| SEQ ID NO: 097 | probe-miR-19a | miR-19a | TCAGTTTTGCATAGATTTGCACA |
| SEQ ID NO: 098 | probe-miR-19b | miR-19b | TCAGTTTTGCATGGATTTGCACA |
| SEQ ID NO: 099 | probe-miR-200a | miR-200a | ACATCGTTACCAGACAGTGTTA |
| SEQ ID NO: 100 | probe-miR-200a* | miR-200a* | TCCAGCACTGTCCGGTAAGATG |
| SEQ ID NO: 101 | probe-miR-200b | miR-200b | GTCATCATTACCAGGCAGTATTA |
| SEQ ID NO: 102 | probe-miR-200c | miR-200c | CCATCATTACCCGGCAGTATTA |
| SEQ ID NO: 103 | probe-miR-202 | miR-202 | TTTTCCCATGCCCTATACCTCT |
| SEQ ID NO: 104 | probe-miR-202* | miR-202* | AAAGAAGTATATGCATAGGAAA |
| SEQ ID NO: 105 | probe-miR-203 | miR-203 | CTAGTGGTCCTAAACATTTCAC |
| SEQ ID NO: 106 | probe-miR-204 | miR-204 | AGGCATAGGATGACAAAGGGAA |
| SEQ ID NO: 107 | probe-miR-205 | miR-205 | CAGACTCCGGTGGAATGAAGGA |
| SEQ ID NO: 108 | probe-miR-206 | miR-206 | CCACACACTTCCTTACATTCCA |
| SEQ ID NO: 109 | probe-miR-208 | miR-208 | ACAAGCTTTTTGCTCGTCTTAT |
| SEQ ID NO: 110 | probe-miR-20a | miR-20a | CTACCTGCACTATAAGCACTTTA |
| SEQ ID NO: 111 | probe-miR-20b | miR-20b | CTACCTGCACTATGAGCACTTTG |
| SEQ ID NO: 112 | probe-miR-21 | miR-21 | TCAACATCAGTCTGATAAGCTA |
| SEQ ID NO: 113 | probe-miR-210 | miR-210 | TCAGCCGCTGTCACACGCACAG |
| SEQ ID NO: 114 | probe-miR-211 | miR-211 | AGGCGAAGGATGACAAAGGGAA |

TABLE 1-continued

Probes of all mature microRNAs in human serum/plasma

| SEQ ID NO | Probes | Corresponding microRNAs | Sequences of probes |
|---|---|---|---|
| SEQ ID NO: 115 | probe-miR-212 | miR-212 | GGCCGTGACTGGAGACTGTTA |
| SEQ ID NO: 116 | probe-miR-213 | miR-213 | GGTACAATCAACGGTCGATGGT |
| SEQ ID NO: 117 | probe-miR-214 | miR-214 | CTGCCTGTCTGTGCCTGCTGT |
| SEQ ID NO: 118 | probe-miR-215 | miR-215 | GTCTGTCAATTCATAGGTCAT |
| SEQ ID NO: 119 | probe-miR-216 | miR-216 | CACAGTTGCCAGCTGAGATTA |
| SEQ ID NO: 120 | probe-miR-217 | miR-217 | ATCCAATCAGTTCCTGATGCAGTA |
| SEQ ID NO: 121 | probe-miR-218 | miR-218 | ACATGGTTAGATCAAGCACAA |
| SEQ ID NO: 122 | probe-miR-219 | miR-219 | AGAATTGCGTTTGGACAATCA |
| SEQ ID NO: 123 | probe-miR-22 | miR-22 | ACAGTTCTTCAACTGGCAGCTT |
| SEQ ID NO: 124 | probe-miR-220 | miR-220 | AAAGTGTCAGATACGGTGTGG |
| SEQ ID NO: 125 | probe-miR-221 | miR-221 | GAAACCCAGCAGACAATGTAGCT |
| SEQ ID NO: 126 | probe-miR-222 | miR-222 | GAGACCCAGTAGCCAGATGTAGCT |
| SEQ ID NO: 127 | probe-miR-223 | miR-223 | GGGGTATTTGACAAACTGACA |
| SEQ ID NO: 128 | probe-miR-224 | miR-224 | TAAACGGAACCACTAGTGACTTG |
| SEQ ID NO: 129 | probe-miR-23a | miR-23a | GGAAATCCCTGGCAATGTGAT |
| SEQ ID NO: 130 | probe-miR-23b | miR-23b | GGTAATCCCTGGCAATGTGAT |
| SEQ ID NO: 131 | probe-miR-24 | miR-24 | CTGTTCCTGCTGAACTGAGCCA |
| SEQ ID NO: 132 | probe-miR-25 | miR-25 | TCAGACCGAGACAAGTGCAATG |
| SEQ ID NO: 133 | probe-miR-26a | miR-26a | GCCTATCCTGGATTACTTGAA |

TABLE 1-continued

Probes of all mature microRNAs in human serum/plasma

| SEQ ID NO | Probes | Corresponding microRNAs | Sequences of probes |
|---|---|---|---|
| SEQ ID NO: 134 | probe-miR-26b | miR-26b | AACCTATCCTGAATTACTTGAA |
| SEQ ID NO: 135 | probe-miR-27a | miR-27a | GCGGAACTTAGCCACTGTGAA |
| SEQ ID NO: 136 | probe-miR-27b | miR-27b | GCAGAACTTAGCCACTGTGAA |
| SEQ ID NO: 137 | probe-miR-28 | miR-28 | CTCAATAGACTGTGAGCTCCTT |
| SEQ ID NO: 138 | probe-miR-296 | miR-296 | ACAGGATTGAGGGGGGGCCCT |
| SEQ ID NO: 139 | probe-miR-299-3p | miR-299-3p | AAGCGGTTTACCATCCCACATA |
| SEQ ID NO: 140 | probe-miR-299-5p | miR-299-5p | ATGTATGTGGGACGGTAAACCA |
| SEQ ID NO: 141 | probe-miR-29a | miR-29a | AACCGATTTCAGATGGTGCTA |
| SEQ ID NO: 142 | probe-miR-29b | miR-29b | AACACTGATTTCAAATGGTGCTA |
| SEQ ID NO: 143 | probe-miR-29c | miR-29c | ACCGATTTCAAATGGTGCTA |
| SEQ ID NO: 144 | probe-miR-301 | miR-301 | GCTTTGACAATACTATTGCACTG |
| SEQ ID NO: 145 | probe-miR-302a | miR-302a | TCACCAAAACATGGAAGCACTTA |
| SEQ ID NO: 146 | probe-miR-302a* | miR-302a* | AAAGCAAGTACATCCACGTTTA |
| SEQ ID NO: 147 | probe-miR-302b | miR-302b | CTACTAAAACATGGAAGCACTTA |
| SEQ ID NO: 148 | probe-miR-302b* | miR-302b* | AGAAAGCACTTCCATGTTAAAGT |
| SEQ ID NO: 149 | probe-miR-302c | miR-302c | CCACTGAAACATGGAAGCACTTA |
| SEQ ID NO: 150 | probe-miR-302c* | miR-302c* | CAGCAGGTACCCCCATGTTAAA |
| SEQ ID NO: 151 | probe-miR-302d | miR-302d | ACACTCAAACATGGAAGCACTTA |
| SEQ ID NO: 152 | probe-miR-30a-3p | miR-30a-3p | GCTGCAAACATCCGACTGAAAG |

TABLE 1-continued

Probes of all mature microRNAs in human serum/plasma

| SEQ ID NO | Probes | Corresponding microRNAs | Sequences of probes |
|---|---|---|---|
| SEQ ID NO: 153 | probe-miR-30a-5p | miR-30a-5p | CTTCCAGTCGAGGATGTTTACA |
| SEQ ID NO: 154 | probe-miR-30b | miR-30b | AGCTGAGTGTAGGATGTTTACA |
| SEQ ID NO: 155 | probe-miR-30c | miR-30c | GCTGAGAGTGTAGGATGTTTACA |
| SEQ ID NO: 156 | probe-miR-30d | miR-30d | CTTCCAGTCGGGGATGTTTACA |
| SEQ ID NO: 157 | probe-miR-30e-3p | miR-30e-3p | GCTGTAAACATCCGACTGAAAG |
| SEQ ID NO: 158 | probe-miR-30e-5p | miR-30e-5p | TCCAGTCAAGGATGTTTACA |
| SEQ ID NO: 159 | probe-miR-31 | miR-31 | CAGCTATGCCAGCATCTTGCC |
| SEQ ID NO: 160 | probe-miR-32 | miR-32 | GCAACTTAGTAATGTGCAATA |
| SEQ ID NO: 161 | probe-miR-320 | miR-320 | TTCGCCCTCTCAACCCAGCTTTT |
| SEQ ID NO: 162 | probe-miR-323 | miR-323 | AGAGGTCGACCGTGTAATGTGC |
| SEQ ID NO: 163 | probe-miR-324-3p | miR-324-3p | CCAGCAGCACCTGGGGCAGTGG |
| SEQ ID NO: 164 | probe-miR-324-5p | miR-324-5p | ACACCAATGCCCTAGGGGATGCG |
| SEQ ID NO: 165 | probe-miR-325 | miR-325 | ACACTTACTGGACACCTACTAGG |
| SEQ ID NO: 166 | probe-miR-326 | miR-326 | CTGGAGGAAGGGCCCAGAGG |
| SEQ ID NO: 167 | probe-miR-328 | miR-328 | ACGGAAGGGCAGAGAGGGCCAG |
| SEQ ID NO: 168 | probe-miR-329 | miR-329 | AAAGAGGTTAACCAGGTGTGTT |
| SEQ ID NO: 169 | probe-miR-33 | miR-33 | CAATGCAACTACAATGCAC |
| SEQ ID NO: 170 | probe-miR-330 | miR-330 | TCTCTGCAGGCCGTGTGCTTTGC |
| SEQ ID NO: 171 | probe-miR-331 | miR-331 | TTCTAGGATAGGCCCAGGGGC |

TABLE 1-continued

Probes of all mature microRNAs in human serum/plasma

| SEQ ID NO | Probes | Corresponding microRNAs | Sequences of probes |
|---|---|---|---|
| SEQ ID NO: 172 | probe-miR-335 | miR-335 | ACATTTTTCGTTATTGCTCTTGA |
| SEQ ID NO: 173 | probe-miR-337 | miR-337 | AAAGGCATCATATAGGAGCTGGA |
| SEQ ID NO: 174 | probe-miR-338 | miR-338 | TCAACAAAATCACTGATGCTGGA |
| SEQ ID NO: 175 | probe-miR-339 | miR-339 | TGAGCTCCTGGAGGACAGGGA |
| SEQ ID NO: 176 | probe-miR-33b | miR-33b | TGCAATGCAACAGCAATGCAC |
| SEQ ID NO: 177 | probe-miR-340 | miR-340 | GGCTATAAAGTAACTGAGACGGA |
| SEQ ID NO: 178 | probe-miR-342 | miR-342 | GACGGGTGCGATTTCTGTGTGAGA |
| SEQ ID NO: 179 | probe-miR-345 | miR-345 | GCCCTGGACTAGGAGTCAGCA |
| SEQ ID NO: 180 | probe-miR-346 | miR-346 | AGAGGCAGGCATGCGGGCAGACA |
| SEQ ID NO: 181 | probe-miR-34a | miR-34a | AACAACCAGCTAAGACACTGCCA |
| SEQ ID NO: 182 | probe-miR-34b | miR-34b | CAATCAGCTAATGACACTGCCTA |
| SEQ ID NO: 183 | probe-miR-34c | miR-34c | GCAATCAGCTAACTACACTGCCT |
| SEQ ID NO: 184 | probe-miR-361 | miR-361 | GTACCCCTGGAGATTCTGATAA |
| SEQ ID NO: 185 | probe-miR-362 | miR-362 | CTCACACCTAGGTTCCAAGGATT |
| SEQ ID NO: 186 | probe-miR-363 | miR-363 | TTACAGATGGATACCGTGCAAT |
| SEQ ID NO: 187 | probe-miR-363* | miR-363* | AAATTGCATCGTGATCCACCCG |
| SEQ ID NO: 188 | probe-miR-365 | miR-365 | ATAAGGATTTTTAGGGGCATTA |
| SEQ ID NO: 189 | probe-miR-367 | miR-367 | TCACCATTGCTAAAGTGCAATT |
| SEQ ID NO: 190 | probe-miR-368 | miR-368 | AAACGTGGAATTTCCTCTATGT |

TABLE 1-continued

Probes of all mature microRNAs in human serum/plasma

| SEQ ID NO | Probes | Corresponding microRNAs | Sequences of probes |
|---|---|---|---|
| SEQ ID NO: 191 | probe-miR-369-3p | miR-369-3p | AAAGATCAACCATGTATTATT |
| SEQ ID NO: 192 | probe-miR-369-5p | miR-369-5p | GCGAATATAACACGGTCGATCT |
| SEQ ID NO: 193 | probe-miR-370 | miR-370 | CCAGGTTCCACCCCAGCAGGC |
| SEQ ID NO: 194 | probe-miR-371 | miR-371 | ACACTCAAAAGATGGCGGCAC |
| SEQ ID NO: 195 | probe-miR-372 | miR-372 | ACGCTCAAATGTCGCAGCACTTT |
| SEQ ID NO: 196 | probe-miR-373 | miR-373 | ACACCCCAAAATCGAAGCACTTC |
| SEQ ID NO: 197 | probe-miR-373* | miR-373* | GGAAAGCGCCCCCATTTTGAGT |
| SEQ ID NO: 198 | probe-miR-374 | miR-374 | CACTTATCAGGTTGTATTATAA |
| SEQ ID NO: 199 | probe-miR-375 | miR-375 | TCACGCGAGCCGAACGAACAAA |
| SEQ ID NO: 200 | probe-miR-376a | miR-376a | ACGTGGATTTTCCTCTATGAT |
| SEQ ID NO: 201 | probe-miR-376a* | miR-376a* | CTCATAGAAGGAGAATCTACC |
| SEQ ID NO: 202 | probe-miR-376b | miR-376b | AACATGGATTTTCCTCTATGAT |
| SEQ ID NO: 203 | probe-miR-377 | miR-377 | ACAAAAGTTGCCTTTGTGTGAT |
| SEQ ID NO: 204 | probe-miR-378 | miR-378 | ACACAGGACCTGGAGTCAGGAG |
| SEQ ID NO: 205 | probe-miR-379 | miR-379 | TACGTTCCATAGTCTACCA |
| SEQ ID NO: 206 | probe-miR-380-3p | miR-380-3p | AAGATGTGGACCATATTACATA |
| SEQ ID NO: 207 | probe-miR-380-5p | miR-380-5p | GCGCATGTTCTATGGTCAACCA |
| SEQ ID NO: 208 | probe-miR-381 | miR-381 | ACAGAGAGCTTGCCCTTGTATA |
| SEQ ID NO: 209 | probe-miR-382 | miR-382 | CGAATCCACCACGAACAACTTC |

TABLE 1-continued

Probes of all mature microRNAs in human serum/plasma

| SEQ ID NO | Probes | Corresponding microRNAs | Sequences of probes |
|---|---|---|---|
| SEQ ID NO: 210 | probe-miR-383 | miR-383 | AGCCACAATCACCTTCTGATCT |
| SEQ ID NO: 211 | probe-miR-384 | miR-384 | TATGAACAATTTCTAGGAAT |
| SEQ ID NO: 212 | probe-miR-409-3p | miR-409-3p | AGGGGTTCACCGAGCAACATTCG |
| SEQ ID NO: 213 | probe-miR-409-5p | miR-409-5p | TGCAAAGTTGCTCGGGTAACCT |
| SEQ ID NO: 214 | probe-miR-410 | miR-410 | AACAGGCCATCTGTGTTATATT |
| SEQ ID NO: 215 | probe-miR-411 | miR-411 | CGTACGCTATACGGTCTACTA |
| SEQ ID NO: 216 | probe-miR-412 | miR-412 | ACGGCTAGTGGACCAGGTGAAGT |
| SEQ ID NO: 217 | probe-miR-421 | miR-421 | GCGCCCAATTAATGTCTGTTGAT |
| SEQ ID NO: 218 | probe-miR-422a | miR-422a | GGCCTTCTGACCCTAAGTCCAG |
| SEQ ID NO: 219 | probe-miR-422b | miR-422b | GGCCTTCTGACTCCAAGTCCAG |
| SEQ ID NO: 220 | probe-miR-423 | miR-423 | CTGAGGGGCCTCAGACCGAGCT |
| SEQ ID NO: 221 | probe-miR-424 | miR-424 | TTCAAAACATGAATTGCTGCTG |
| SEQ ID NO: 222 | probe-miR-425 | miR-425 | GGCGGACACGACATTCCCGAT |
| SEQ ID NO: 223 | probe-miR-425-5p | miR-425-5p | TCAACGGGAGTGATCGTGTCATT |
| SEQ ID NO: 224 | probe-miR-429 | miR-429 | ACGGTTTTACCAGACAGTATTA |
| SEQ ID NO: 225 | probe-miR-431 | miR-431 | TGCATGACGGCCTGCAAGACA |
| SEQ ID NO: 226 | probe-miR-432 | miR-432 | CCACCCAATGACCTACTCCAAGA |
| SEQ ID NO: 227 | probe-miR-432* | miR-432* | AGACATGGAGGAGCCATCCAG |
| SEQ ID NO: 228 | probe-miR-433 | miR-433 | ACACCGAGGAGCCCATCATGAT |

TABLE 1-continued

Probes of all mature microRNAs in human serum/plasma

| SEQ ID NO | Probes | Corresponding microRNAs | Sequences of probes |
|---|---|---|---|
| SEQ ID NO: 229 | probe-miR-448 | miR-448 | ATGGGACATCCTACATATGCAA |
| SEQ ID NO: 230 | probe-miR-449 | miR-449 | ACCAGCTAACAATACACTGCCA |
| SEQ ID NO: 231 | probe-miR-450 | miR-450 | TATTAGGAACACATCGCAAAAA |
| SEQ ID NO: 232 | probe-miR-451 | miR-451 | AAACTCAGTAATGGTAACGGTTT |
| SEQ ID NO: 233 | probe-miR-452 | miR-452 | GTCTCAGTTTCCTCTGCAAACA |
| SEQ ID NO: 234 | probe-miR-452* | miR-452* | CTTCTTTGCAGATGAGACTGA |
| SEQ ID NO: 235 | probe-miR-453 | miR-453 | CGAACTCACCACGGACAACCTC |
| SEQ ID NO: 236 | probe-miR-455 | miR-455 | CGATGTAGTCCAAAGGCACATA |
| SEQ ID NO: 237 | probe-miR-483 | miR-483 | AGAAGACGGGAGGAGAGGAGTGA |
| SEQ ID NO: 238 | probe-miR-484 | miR-484 | ATCGGGAGGGGACTGAGCCTGA |
| SEQ ID NO: 239 | probe-miR-485-3p | miR-485-3p | AGAGGAGAGCCGTGTATGAC |
| SEQ ID NO: 240 | probe-miR-485-5p | miR-485-5p | GAATTCATCACGGCCAGCCTCT |
| SEQ ID NO: 241 | probe-miR-486 | miR-486 | CTCGGGGCAGCTCAGTACAGGA |
| SEQ ID NO: 242 | probe-miR-487a | miR-487a | AACTGGATGTCCCTGTATGATT |
| SEQ ID NO: 243 | probe-miR-487b | miR-487b | AAGTGGATGACCCTGTACGATT |
| SEQ ID NO: 244 | probe-miR-488 | miR-488 | TTGAGAGTGCCATTATCTGGG |
| SEQ ID NO: 245 | probe-miR-489 | miR-489 | GCTGCCGTATATGTGATGTCACT |
| SEQ ID NO: 246 | probe-miR-490 | miR-490 | CAGCATGGAGTCCTCCAGGTTG |
| SEQ ID NO: 247 | probe-miR-491 | miR-491 | TCCTCATGGAAGGGTTCCCCACT |

TABLE 1-continued

Probes of all mature microRNAs in human serum/plasma

| SEQ ID NO | Probes | Corresponding microRNAs | Sequences of probes |
|---|---|---|---|
| SEQ ID NO: 248 | probe-miR-492 | miR-492 | AAGAATCTTGTCCCGCAGGTCCT |
| SEQ ID NO: 249 | probe-miR-493 | miR-493 | AATGAAAGCCTACCATGTACAA |
| SEQ ID NO: 250 | probe-miR-493-3p | miR-493-3p | CTGGCACACAGTAGACCTTCA |
| SEQ ID NO: 251 | probe-miR-494 | miR-494 | AAGAGGTTTCCCGTGTATGTTTCA |
| SEQ ID NO: 252 | probe-miR-495 | miR-495 | AAAGAAGTGCACCATGTTTGTTT |
| SEQ ID NO: 253 | probe-miR-496 | miR-496 | GAGATTGGCCATGTAAT |
| SEQ ID NO: 254 | probe-miR-497 | miR-497 | ACAAACCACAGTGTGCTGCTG |
| SEQ ID NO: 255 | probe-miR-498 | miR-498 | GAAAAACGCCCCCTGGCTTGAAA |
| SEQ ID NO: 256 | probe-miR-499 | miR-499 | TTAAACATCACTGCAAGTCTTAA |
| SEQ ID NO: 257 | probe-miR-500 | miR-500 | CAGAATCCTTGCCCAGGTGCAT |
| SEQ ID NO: 258 | probe-miR-501 | miR-501 | TCTCACCCAGGGACAAAGGATT |
| SEQ ID NO: 259 | probe-miR-502 | miR-502 | TAGCACCCAGATAGCAAGGAT |
| SEQ ID NO: 260 | probe-miR-503 | miR-503 | CTGCAGAACTGTTCCCGCTGCTA |
| SEQ ID NO: 261 | probe-miR-504 | miR-504 | ATAGAGTGCAGACCAGGGTCT |
| SEQ ID NO: 262 | probe-miR-505 | miR-505 | GAGGAAACCAGCAAGTGTTGAC |
| SEQ ID NO: 263 | probe-miR-506 | miR-506 | TCTACTCAGAAGGGTGCCTTA |
| SEQ ID NO: 264 | probe-miR-507 | miR-507 | TTCACTCCAAAAGGTGCAAAA |
| SEQ ID NO: 265 | probe-miR-508 | miR-508 | TCTACTCCAAAAGGCTACAATCA |
| SEQ ID NO: 266 | probe-miR-509 | miR-509 | TCTACCCACAGACGTACCAATCA |

TABLE 1-continued

Probes of all mature microRNAs in human serum/plasma

| SEQ ID NO | Probes | Corresponding microRNAs | Sequences of probes |
|---|---|---|---|
| SEQ ID NO: 267 | probe-miR-510 | miR-510 | TGTGATTGCCACTCTCCTGAGTA |
| SEQ ID NO: 268 | probe-miR-511 | miR-511 | TGACTGCAGAGCAAAAGACAC |
| SEQ ID NO: 269 | probe-miR-512-3p | miR-512-3p | GACCTCAGCTATGACAGCACTT |
| SEQ ID NO: 270 | probe-miR-512-5p | miR-512-5p | GAAAGTGCCCTCAAGGCTGAGTG |
| SEQ ID NO: 271 | probe-miR-513 | miR-513 | ATAAATGACACCTCCCTGTGAA |
| SEQ ID NO: 272 | probe-miR-514 | miR-514 | CTACTCACAGAAGTGTCAAT |
| SEQ ID NO: 273 | probe-miR-515-3p | miR-515-3p | ACGCTCCAAAAGAAGGCACTC |
| SEQ ID NO: 274 | probe-miR-515-5p | miR-515-5p | CAGAAAGTGCTTTCTTTTGGAGAA |
| SEQ ID NO: 275 | probe-miR-516-3p | miR-516-3p | ACCCTCTGAAAGGAAGCA |
| SEQ ID NO: 276 | probe-miR-516-5p | miR-516-5p | AAAGTGCTTCTTACCTCCAGAT |
| SEQ ID NO: 277 | probe-miR-517* | miR-517* | AGACAGTGCTTCCATCTAGAGG |
| SEQ ID NO: 278 | probe-miR-517a | miR-517a | AACACTCTAAAGGGATGCACGAT |
| SEQ ID NO: 279 | probe-miR-517b | miR-517b | AACACTCTAAAGGGATGCACGA |
| SEQ ID NO: 280 | probe-miR-517c | miR-517c | ACACTCTAAAAGGATGCACGAT |
| SEQ ID NO: 281 | probe-miR-518a | miR-518a | TCCAGCAAAGGGAAGCGCTTT |
| SEQ ID NO: 282 | probe-miR-518a-2* | miR-518a-2* | AAAGGGCTTCCCTTTGCAGA |
| SEQ ID NO: 283 | probe-miR-518b | miR-518b | ACCTCTAAAGGGGAGCGCTTTG |
| SEQ ID NO: 284 | probe-miR-518c | miR-518c | CACTCTAAAGAGAAGCGCTTTG |
| SEQ ID NO: 285 | probe-miR-518c* | miR-518c* | CAGAAAGTGCTTCCCTCCAGAGA |

TABLE 1-continued

Probes of all mature microRNAs in human serum/plasma

| SEQ ID NO | Probes | Corresponding microRNAs | Sequences of probes |
|---|---|---|---|
| SEQ ID NO: 286 | probe-miR-518d | miR-518d | GCTCCAAAGGGAAGCGCTTTG |
| SEQ ID NO: 287 | probe-miR-518e | miR-518e | ACACTCTGAAGGGAAGCGCTTT |
| SEQ ID NO: 288 | probe-miR-518f | miR-518f | TCCTCTAAAGAGAAGCGCTTT |
| SEQ ID NO: 289 | probe-miR-518f* | miR-518f* | AGAGAAAGTGCTTCCCTCTAGAG |
| SEQ ID NO: 290 | probe-miR-519a | miR-519a | GTAACACTCTAAAAGGATGCACTTT |
| SEQ ID NO: 291 | probe-miR-519b | miR-519b | AAACCTCTAAAAGGATGCACTTT |
| SEQ ID NO: 292 | probe-miR-519c | miR-519c | ATCCTCTAAAAAGATGCACTTT |
| SEQ ID NO: 293 | probe-miR-519d | miR-519d | ACACTCTAAAGGGAGGCACTTTG |
| SEQ ID NO: 294 | probe-miR-519e | miR-519e | ACACTCTAAAAGGAGGCACTTT |
| SEQ ID NO: 295 | probe-miR-519e* | miR-519e* | GAAAGTGCTCCCTTTTGGAGAA |
| SEQ ID NO: 296 | probe-miR-520a | miR-520a | ACAGTCCAAAGGGAAGCACTTT |
| SEQ ID NO: 297 | probe-miR-520a* | miR-520a* | AGAAAGTACTTCCCTCTGGAG |
| SEQ ID NO: 298 | probe-miR-520b | miR-520b | CCCTCTAAAAGGAAGCACTTT |
| SEQ ID NO: 299 | probe-miR-520c | miR-520c | AACCCTCTAAAAGGAAGCACTTT |
| SEQ ID NO: 300 | probe-miR-520d | miR-520d | AACCCACCAAAGAGAAGCACTTT |
| SEQ ID NO: 301 | probe-miR-520d* | miR-520d* | CAGAAAGGGCTTCCCTTTGTAGA |
| SEQ ID NO: 302 | probe-miR-520e | miR-520e | CCCTCAAAAAGGAAGCACTTT |
| SEQ ID NO: 303 | probe-miR-520f | miR-520f | AACCCTCTAAAAGGAAGCACTT |
| SEQ ID NO: 304 | probe-miR-520g | miR-520g | ACACTCTAAAGGGAAGCACTTTGT |

TABLE 1-continued

Probes of all mature microRNAs in human serum/plasma

| SEQ ID NO | Probes | Corresponding microRNAs | Sequences of probes |
|---|---|---|---|
| SEQ ID NO: 305 | probe-miR-520h | miR-520h | ACTCTAAAGGGAAGCACTTTGT |
| SEQ ID NO: 306 | probe-miR-521 | miR-521 | ACACTCTAAAGGGAAGTGCGTT |
| SEQ ID NO: 307 | probe-miR-522 | miR-522 | AACACTCTAAAGGGAACCATTTT |
| SEQ ID NO: 308 | probe-miR-523 | miR-523 | CCCTCTATAGGGAAGCGCGTT |
| SEQ ID NO: 309 | probe-miR-524 | miR-524 | ACTCCAAAGGGAAGCGCCTTC |
| SEQ ID NO: 310 | probe-miR-524* | miR-524* | GAGAAAGTGCTTCCCTTTGTAG |
| SEQ ID NO: 311 | probe-miR-525 | miR-525 | AGAAAGTGCATCCCTCTGGAG |
| SEQ ID NO: 312 | probe-miR-525* | miR-525* | GCTCTAAAGGGAAGCGCCTTC |
| SEQ ID NO: 313 | probe-miR-526a | miR-526a | AGAAAGTGCTTCCCTCTAGAG |
| SEQ ID NO: 314 | probe-miR-526b | miR-526b | AACAGAAAGTGCTTCCCTCAAGAG |
| SEQ ID NO: 315 | probe-miR-526b* | miR-526b* | GCCTCTAAAAGGAAGCACTTT |
| SEQ ID NO: 316 | probe-miR-526c | miR-526c | AACAGAAAGCGCTTCCCTCTAGAG |
| SEQ ID NO: 317 | probe-miR-527 | miR-527 | AGAAAGGGCTTCCCTTTGCAG |
| SEQ ID NO: 318 | probe-miR-532 | miR-532 | ACGGTCCTACACTCAAGGCATG |
| SEQ ID NO: 319 | probe-miR-542-3p | miR-542-3p | TTTCAGTTATCAATCTGTCACA |
| SEQ ID NO: 320 | probe-miR-542-5p | miR-542-5p | CTCGTGACATGATGATCCCCGA |
| SEQ ID NO: 321 | probe-miR-544 | miR-544 | ACTTGCTAAAAATGCAGAAT |
| SEQ ID NO: 322 | probe-miR-545 | miR-545 | CACACAATAAATGTTTGCTGAT |
| SEQ ID NO: 323 | probe-miR-548a | miR-548a | GCAAAAGTAATTGCCAGTTTTG |

TABLE 1-continued

Probes of all mature microRNAs in human serum/plasma

| SEQ ID NO | Probes | Corresponding microRNAs | Sequences of probes |
|---|---|---|---|
| SEQ ID NO: 324 | probe-miR-548b | miR-548b | ACAAAAGCAACTGAGGTTCTTG |
| SEQ ID NO: 325 | probe-miR-548c | miR-548c | GCAAAAGTAATTGAGATTTTTG |
| SEQ ID NO: 326 | probe-miR-548d | miR-548d | GCAAAAGAAACTGTGGTTTTTG |
| SEQ ID NO: 327 | probe-miR-549 | miR-549 | AGAGCTCATCCATAGTTGTCA |
| SEQ ID NO: 328 | probe-miR-550 | miR-550 | ATGTGCCTGAGGGAGTAAGACA |
| SEQ ID NO: 329 | probe-miR-551a | miR-551a | TGGAAACCAAGAGTGGGTCGC |
| SEQ ID NO: 330 | probe-miR-552 | miR-552 | TTGTCTAACCAGTCACCTGTT |
| SEQ ID NO: 331 | probe-miR-553 | miR-553 | AAAACAAAATCTCACCGTTTT |
| SEQ ID NO: 332 | probe-miR-554 | miR-554 | ACTGGCTGAGTCAGGACTAGC |
| SEQ ID NO: 333 | probe-miR-555 | miR-555 | ATCAGAGGTTCAGCTTACCCT |
| SEQ ID NO: 334 | probe-miR-556 | miR-556 | CATATTACAATGAGCTCATC |
| SEQ ID NO: 335 | probe-miR-557 | miR-557 | AGACAAGGCCCACCCGTGCAAAC |
| SEQ ID NO: 336 | probe-miR-558 | miR-558 | ATTTTGGTACAGCAGCTCA |
| SEQ ID NO: 337 | probe-miR-559 | miR-559 | TTTTGGTGCATATTTACTTTA |
| SEQ ID NO: 338 | probe-miR-560 | miR-560 | GGCGGCCGGCCGGCGCACGC |
| SEQ ID NO: 339 | probe-miR-561 | miR-561 | ACTTCAAGGATCTTAAACTTTG |
| SEQ ID NO: 340 | probe-miR-562 | miR-562 | GCAAATGGTACAGCTACTTT |
| SEQ ID NO: 341 | probe-miR-563 | miR-563 | GGGAAACGTATGTCAACCT |
| SEQ ID NO: 342 | probe-miR-564 | miR-564 | GCCTGCTGACACCGTGCCT |

TABLE 1-continued

Probes of all mature microRNAs in human serum/plasma

| SEQ ID NO | Probes | Corresponding microRNAs | Sequences of probes |
|---|---|---|---|
| SEQ ID NO: 343 | probe-miR-565 | miR-565 | AAACAGACATCGCGAGCCAGCC |
| SEQ ID NO: 344 | probe-miR-566 | miR-566 | GTTGGGATCACAGGCGCCC |
| SEQ ID NO: 345 | probe-miR-567 | miR-567 | GTTCTGTCCTGGAAGAACATACT |
| SEQ ID NO: 346 | probe-miR-568 | miR-568 | GTGTGTATACATTTATACAT |
| SEQ ID NO: 347 | probe-miR-569 | miR-569 | ACTTTCCAGGATTCATTAACT |
| SEQ ID NO: 348 | probe-miR-570 | miR-570 | TGCAAAGGTAATTGCTGTTTC |
| SEQ ID NO: 349 | probe-miR-571 | miR-571 | CTCACTCAGATGGCCAACTCA |
| SEQ ID NO: 350 | probe-miR-572 | miR-572 | TGGGCCACCGCCGAGCGGAC |
| SEQ ID NO: 351 | probe-miR-573 | miR-573 | CTGATCAGTTACACATCACTTCAG |
| SEQ ID NO: 352 | probe-miR-574 | miR-574 | GTGGGTGTGTGCATGAGCGTG |
| SEQ ID NO: 353 | probe-miR-575 | miR-575 | GCTCCTGTCCAACTGGCTC |
| SEQ ID NO: 354 | probe-miR-576 | miR-576 | CAAAGACGTGGAGAAATTAGAAT |
| SEQ ID NO: 355 | probe-miR-577 | miR-577 | CAGGTACCAATATTTTATCTA |
| SEQ ID NO: 356 | probe-miR-578 | miR-578 | ACAATCCTAGAGCACAAGAAG |
| SEQ ID NO: 357 | probe-miR-579 | miR-579 | ATCGCGGTTTATACCAAATGAAT |
| SEQ ID NO: 358 | probe-miR-580 | miR-580 | CCTAATGATTCATCATTCTCAA |
| SEQ ID NO: 359 | probe-miR-581 | miR-581 | ACTGATCTAGAGAACACAAGA |
| SEQ ID NO: 360 | probe-miR-582 | miR-582 | AGTAACTGGTTGAACAACTGTAA |
| SEQ ID NO: 361 | probe-miR-583 | miR-583 | GTAATGGGACCTTCCTCTTTG |

TABLE 1-continued

Probes of all mature microRNAs in human serum/plasma

| SEQ ID NO | Probes | Corresponding microRNAs | Sequences of probes |
|---|---|---|---|
| SEQ ID NO: 362 | probe-miR-584 | miR-584 | CTCAGTCCCAGGCAAACCATAA |
| SEQ ID NO: 363 | probe-miR-585 | miR-585 | TAGCATACAGATACGCCCA |
| SEQ ID NO: 364 | probe-miR-586 | miR-586 | GGACCTAAAAATACAATGCATA |
| SEQ ID NO: 365 | probe-miR-587 | miR-587 | GTGACTCATCACCTATGGAAA |
| SEQ ID NO: 366 | probe-miR-588 | miR-588 | GTTCTAACCCATTGTGGCCAA |
| SEQ ID NO: 367 | probe-miR-589 | miR-589 | TCTGGGAACCGGCATTTGTTCTGA |
| SEQ ID NO: 368 | probe-miR-590 | miR-590 | CTGCACTTTTATGAATAAGCTC |
| SEQ ID NO: 369 | probe-miR-591 | miR-591 | ACAATGAGAACCCATGGTCT |
| SEQ ID NO: 370 | probe-miR-592 | miR-592 | ACATCATCGCATATTGACACAA |
| SEQ ID NO: 371 | probe-miR-593 | miR-593 | GCTGAGCAATGCCTGGCTGGTGCCT |
| SEQ ID NO: 372 | probe-miR-594 | miR-594 | AAAGTCACAGGCCACCCCAGATGGG |
| SEQ ID NO: 373 | probe-miR-595 | miR-595 | AGACACACCACGGCACACTTC |
| SEQ ID NO: 374 | probe-miR-596 | miR-596 | CCCGAGGAGCCGGGCAGGCTT |
| SEQ ID NO: 375 | probe-miR-597 | miR-597 | ACAGTGGTCATCGAGTGACACA |
| SEQ ID NO: 376 | probe-miR-598 | miR-598 | TGACGATGACAACGATGACGTA |
| SEQ ID NO: 377 | probe-miR-599 | miR-599 | GTTTGATAAACTGACACAAC |
| SEQ ID NO: 378 | probe-miR-600 | miR-600 | GAGCAAGGCTCTTGTCTGTAAGT |
| SEQ ID NO: 379 | probe-miR-601 | miR-601 | CTCCTCCAACAATCCTAGACCA |
| SEQ ID NO: 380 | probe-miR-602 | miR-602 | GGGCCGCAGCTGTCGCCCGTGTC |

TABLE 1-continued

Probes of all mature microRNAs in human serum/plasma

| SEQ ID NO | Probes | Corresponding microRNAs | Sequences of probes |
|---|---|---|---|
| SEQ ID NO: 381 | probe-miR-603 | miR-603 | GCAAAAGTAATTGCAGTGTGTG |
| SEQ ID NO: 382 | probe-miR-604 | miR-604 | GTCCTGAATTCCGCAGCCT |
| SEQ ID NO: 383 | probe-miR-605 | miR-605 | AGGAGAAGGCACCATGGGATTTA |
| SEQ ID NO: 384 | probe-miR-606 | miR-606 | ATCTTTGATTTTCAGTAGTTT |
| SEQ ID NO: 385 | probe-miR-607 | miR-607 | GTTATAGATCTGGATTTGAAC |
| SEQ ID NO: 386 | probe-miR-608 | miR-608 | ACGGAGCTGTCCCAACACCACCCCT |
| SEQ ID NO: 387 | probe-miR-609 | miR-609 | AGAGATGAGAGAAACACCCT |
| SEQ ID NO: 388 | probe-miR-610 | miR-610 | TCCCAGCACACATTTAGCTCA |
| SEQ ID NO: 389 | probe-miR-611 | miR-611 | GTCAGACCCCGAGGGGTCCTCGC |
| SEQ ID NO: 390 | probe-miR-612 | miR-612 | AAGGAGCTCAGAAGCCCTGCCCAGC |
| SEQ ID NO: 391 | probe-miR-613 | miR-613 | GGCAAAGAAGGAACATTCCT |
| SEQ ID NO: 392 | probe-miR-614 | miR-614 | CCACCTGGCAAGAACAGGCGTTC |
| SEQ ID NO: 393 | probe-miR-615 | miR-615 | AGAGGGAGACCCAGGCTCGGA |
| SEQ ID NO: 394 | probe-miR-616 | miR-616 | AAGTCACTGAAGGGTTTTGAGT |
| SEQ ID NO: 395 | probe-miR-617 | miR-617 | GCCACCTTCAAATGGGAAGTCT |
| SEQ ID NO: 396 | probe-miR-618 | miR-618 | ACTCAGAAGGACAAGTAGAGTTT |
| SEQ ID NO: 397 | probe-miR-619 | miR-619 | ACTGGGCACAAACATGTCCAGGTC |
| SEQ ID NO: 398 | probe-miR-620 | miR-620 | ATTTCTATATCTATCTCCAT |
| SEQ ID NO: 399 | probe-miR-621 | miR-621 | AGGTAAGCGCTGTTGCTAGCC |

TABLE 1-continued

Probes of all mature microRNAs in human serum/plasma

| SEQ ID NO | Probes | Corresponding microRNAs | Sequences of probes |
|---|---|---|---|
| SEQ ID NO: 400 | probe-miR-622 | miR-622 | GCTCCAACCTCAGCAGACTGT |
| SEQ ID NO: 401 | probe-miR-623 | miR-623 | ACCCAACAGCCCCTGCAAGGGAT |
| SEQ ID NO: 402 | probe-miR-624 | miR-624 | TGAACACAAGGTACTGGTACTA |
| SEQ ID NO: 403 | probe-miR-625 | miR-625 | AGGACTATAGAACTTTCCCCCT |
| SEQ ID NO: 404 | probe-miR-626 | miR-626 | AAGACATTTTCAGACAGCT |
| SEQ ID NO: 405 | probe-miR-627 | miR-627 | TCCTCTTTTCTTAGAGACTCAC |
| SEQ ID NO: 406 | probe-miR-628 | miR-628 | CGACTGCCACTCTTACTAGA |
| SEQ ID NO: 407 | probe-miR-629 | miR-629 | GCTGGGCTTACGTTGGGAGAAC |
| SEQ ID NO: 408 | probe-miR-630 | miR-630 | ACCTTCCCTGGTACAGAATACT |
| SEQ ID NO: 409 | probe-miR-631 | miR-631 | GCTGAGGTCTGGGCCAGGTCT |
| SEQ ID NO: 410 | probe-miR-632 | miR-632 | TCCCACAGGAAGCAGACAC |
| SEQ ID NO: 411 | probe-miR-633 | miR-633 | TTTATTGTGGTAGATACTATTAG |
| SEQ ID NO: 412 | probe-miR-634 | miR-634 | GTCCAAAGTTGGGGTGCTGGTT |
| SEQ ID NO: 413 | probe-miR-635 | miR-635 | GGACATTGTTTCAGTGCCCAAGT |
| SEQ ID NO: 414 | probe-miR-636 | miR-636 | CTGCGGGCGGGACGAGCAAGCACA |
| SEQ ID NO: 415 | probe-miR-637 | miR-637 | ACGCAGAGCCCGAAAGCCCCCAGT |
| SEQ ID NO: 416 | probe-miR-638 | miR-638 | AGGCCGCCACCCGCCCGCGATCCCT |
| SEQ ID NO: 417 | probe-miR-639 | miR-639 | ACAGCGCTCGCAACCGCAGCGAT |
| SEQ ID NO: 418 | probe-miR-640 | miR-640 | AGAGGCAGGTTCCTGGATCAT |

TABLE 1-continued

Probes of all mature microRNAs in human serum/plasma

| SEQ ID NO | Probes | Corresponding microRNAs | Sequences of probes |
|---|---|---|---|
| SEQ ID NO: 419 | probe-miR-641 | miR-641 | GAGGTGACTCTATCCTATGTCTTT |
| SEQ ID NO: 420 | probe-miR-642 | miR-642 | CAAGACACATTTGGAGAGGGAC |
| SEQ ID NO: 421 | probe-miR-643 | miR-643 | CTACCTGAGCTAGCATACAAGT |
| SEQ ID NO: 422 | probe-miR-644 | miR-644 | GCTCTAAGAAAGCCACACT |
| SEQ ID NO: 423 | probe-miR-645 | miR-645 | TCAGCAGTACCAGCCTAGA |
| SEQ ID NO: 424 | probe-miR-646 | miR-646 | GCCTCAGAGGCAGCTGCTT |
| SEQ ID NO: 425 | probe-miR-647 | miR-647 | GAAGGAAGTGAGTGCAGCCAC |
| SEQ ID NO: 426 | probe-miR-648 | miR-648 | ACCAGTGCCCTGCACACTT |
| SEQ ID NO: 427 | probe-miR-649 | miR-649 | GACTCTTGAACAACACAGGTTT |
| SEQ ID NO: 428 | probe-miR-650 | miR-650 | GTCCTGAGAGCGCTGCCTCCT |
| SEQ ID NO: 429 | probe-miR-651 | miR-651 | CAAAAGTCAAGCTTATCCTAAA |
| SEQ ID NO: 430 | probe-miR-652 | miR-652 | TGCACAACCCTAGTGGCGCCATT |
| SEQ ID NO: 431 | probe-miR-653 | miR-653 | GTTCAGTAGAGATTGTTTCAA |
| SEQ ID NO: 432 | probe-miR-654 | miR-654 | GCACATGTTCTGCGGCCCACCA |
| SEQ ID NO: 433 | probe-miR-655 | miR-655 | AAAGAGGTTAACCATGTATTAT |
| SEQ ID NO: 434 | probe-miR-656 | miR-656 | AGAGGTTGACTGTATAATATT |
| SEQ ID NO: 435 | probe-miR-657 | miR-657 | CCTAGAGAGGGTGAGAACCTGCC |
| SEQ ID NO: 436 | probe-miR-658 | miR-658 | ACCAACGGACCTACTTCCCTCCGCC |
| SEQ ID NO: 437 | probe-miR-659 | miR-659 | TGGGGACCCTCCCTGAACCAAG |

TABLE 1-continued

Probes of all mature microRNAs in human serum/plasma

| SEQ ID NO | Probes | Corresponding microRNAs | Sequences of probes |
|---|---|---|---|
| SEQ ID NO: 438 | probe-miR-660 | miR-660 | CAACTCCGATATGCAATGGGTA |
| SEQ ID NO: 439 | probe-miR-661 | miR-661 | ACGCGCAGGCCAGAGACCCAGGCA |
| SEQ ID NO: 440 | probe-miR-662 | miR-662 | CTGCTGGGCCACAACGTGGGA |
| SEQ ID NO: 441 | probe-miR-663 | miR-663 | GCGGTCCCGCGGCGCCCCGCCT |
| SEQ ID NO: 442 | probe-miR-7 | miR-7 | CAACAAAATCACTAGTCTTCCA |
| SEQ ID NO: 443 | probe-miR-9 | miR-9 | TCATACAGCTAGATAACCAAAGA |
| SEQ ID NO: 444 | probe-miR-9* | miR-9* | ACTTTCGGTTATCTAGCTTTA |
| SEQ ID NO: 445 | probe-miR-92 | miR-92 | CAGGCCGGGACAAGTGCAATA |
| SEQ ID NO: 446 | probe-miR-93 | miR-93 | CTACCTGCACGAACAGCACTTT |
| SEQ ID NO: 447 | probe-miR-95 | miR-95 | TGCTCAATAAATACCCGTTGAA |
| SEQ ID NO: 448 | probe-miR-96 | miR-96 | GCAAAAATGTGCTAGTGCCAAA |
| SEQ ID NO: 449 | probe-miR-98 | miR-98 | AACAATACAACTTACTACCTCA |
| SEQ ID NO: 450 | probe-miR-99a | miR-99a | CACAAGATCGGATCTACGGGTT |
| SEQ ID NO: 451 | probe-miR-99b | miR-99b | CGCAAGGTCGGTTCTACGGGTG |

Specifically, among the above-mentioned combinations, methods, kits or biochips, the said evaluation of the physiological and/or pathological condition of a subject is to determine the physiological and/or pathological condition of the subject after being administrated a test sample, which is specifically useful for screening the test sample for the activities on the prevention and/or treatment of diseases; the said evaluation of the physiological and/or pathological condition of a subject is to diagnose and/or differentially diagnose the diseases of the subject; the said evaluation of the physiological and/or pathological condition of a subject is to evaluate the effectiveness of the treatment on the diseases of the subject; the said evaluation of the physiological and/or pathological condition of a subject is to predict the disease occurrence of the subject, which is specifically the occurrence of complications and/or the relapse of malignant diseases; the above-mentioned combinations, methods, kits or biochips can also be useful for detecting the subject for prohibited drugs-taking.

The above-mentioned diseases include a variety of tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary, diseases of reproductive system and diseases of locomotor system.

The above-mentioned serum/plasma derives from the living bodies, tissues, organs and/or corpuses of the subject.

The problems to be solved by the present invention include: (1) analyzing and identifying the microRNA molecules and their stability in serum/plasma of a variety of animals such as human, mice and rats; (2) studying the specificity changes of microRNAs in serum/plasma during the course of various clinical diseases including a variety of tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary system, diseases of reproductive system and diseases of locomotor system; (3) detecting the respective changes of microRNAs in serum/plasma for different diseases through biochip and sequencing technology for microRNAs in serum/plasma; (4) screening a kind of microRNA molecules in serum/plasma which have relatively greater differential expression during the course of diseases and normal physiological conditions to develop detection technologies for serum/plasma microRNAs, and then preparing biochips and diagnostic kits useful for disease diagnosis etc.

Specifically, the present invention analyzes and identifies the existence of microRNA molecules in serum/plasma of various animals such as human, mice and rats through the methods of RT-PCR, Real-time PCR, Northern blotting, RNase protection assay, Solexa sequencing technology and biochip. The stability of microRNAs in serum/plasma is studied by comparing the changes of microRNAs by the effect of DNase and RNase. The existence of serum/plasma microRNAs molecules and the correctness of their sequences are further verified through sequencing and comparing the PCR products of serum/plasma microRNAs.

The detailed preparation and analysis for serum/plasma microRNAs are as follows:

RT-PCR method: collecting serum/plasma samples; conducting reverse transcription reaction on serum/plasma samples to prepare cDNA samples, or extracting total RNA of serum/plasma with Trizol reagent and then conducting reverse transcription reaction so as to prepare cDNA samples; designing a primer through mature microRNAs so as to conduct PCR reaction; carrying out agarose gel electrophoresis with the products of PCR; and observing and taking photographs for the results under ultraviolet lamp after EB staining Real-time PCR method: collecting serum/plasma samples; conducting reverse transcription reaction on serum/plasma samples to prepare cDNA samples, or extracting total RNA of serum/plasma with Trizol reagent and then conducting reverse transcription reaction so as to prepare cDNA samples; designing a primer of PCR through mature microRNAs and adding a fluorescent probe EVA GREEN so as to carry out PCR reaction; analyzing and processing the data and then comparing the results.

Northern blotting method: collecting serum/plasma samples; extracting total RNA of serum/plasma with Trizol reagent; conducting denaturing PAGE-electrophoresis and membrane transferring experiment; preparing isotope-labeled microRNA probes; conducting membrane hybridization reaction; detecting the isotope signal for results such as using phosphor-screen scanning technology.

RNase protection assay: firstly synthesizing an antisense RNA probe, labelling it with isotopes and purifying it; collecting serum/plasma samples and extracting RNA; dissolving the extracted DNA in a hybrid buffer and then adding an antisense RNA probe so as to conduct hybridization reaction; adding a RNase digestion solution to irritate reaction; subjecting the resultant material to electrophoresis and radioautography; and analyzing the results.

Solexa sequencing technology: collecting serum/plasma samples; extracting total RNA of serum/plasma with Trizol reagent; conducting PAGE-electrophoresis to recover RNA molecules of 17~27 nt; enzyme-linking adaptor prime to the 3' and 5' end of small RNA molecules respectively; conducting RT-PCR reaction prior to sequencing; and analyzing and processing the data.

Biochip method: arraying a library of all over 500 mature microRNAs to prepare biochips; collecting serum/plasma samples; extracting total RNA of serum/plasma; separating microRNAs by column separation; fluorescently-labelling microRNAs by use of T4 RNA ligase; conducting hybridization reaction with a biochip; and detecting and analyzing the data.

The change trend and change volume of serum/plasma microRNAs during various diseases and their relevancy with various diseases are analyzed through the above-mentioned technologies of RT-PCR, Real-time PCR, Northern blotting, RNase protection assay, Solexa sequencing technology, Biochip, etc. Among others, what to do firstly is to detect and analyze the changes of let-7a, let-7b, let-7c, let-7d, let-7e, let-7f, let-7g, let-7i, miR-1, miR-100, miR-101, miR-103, miR-105, miR-106a, miR-106b, miR-107, miR-10a, miR-10b, miR-122a, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-142-5p, miR-143, miR-144, miR-145, miR-146a, miR-146b, miR-147, miR-148a, miR-148b, miR-149, miR-150, miR-151, miR-152, miR-153, miR-154, miR-154*, miR-155, miR-15a, miR-15b, miR-16, miR-17-3p, miR-17-5p, miR-181a, miR-181b, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193a, miR-193b, miR-194, miR-195, miR-196a, miR-196b, miR-197, miR-198, miR-199a, miR-199a*, miR-199b, miR-19a, miR-19b, miR-200a, miR-200a*, miR-200b, miR-200c, miR-202, miR-202*, miR-203, miR-204, miR-205, miR-206, miR-208, miR-20a, miR-20b, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-483, miR-484, miR-485-3p, miR-485-5p, miR-486, miR-487a, miR-487b, miR-488, miR-489, miR-490, miR-491, miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548d, miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591, miR-592, miR-593, miR-594, miR-595, miR-596, miR-597, miR-598, miR-599, miR-600, miR-601, miR-602, miR-603, miR-604, miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-7, miR-9, miR-9*, miR-92, miR-93, miR-95, miR-96, miR-98, miR-99a and miR-99b in various clinical diseases (including a variety of tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary system, diseases of reproductive system and diseases of locomotor system); Biochips of serum/plasma microRNAs are prepared to determine the changes of serum/plasma microRNAs in different diseases, and meanwhile, Solexa sequencing and analysis on microRNAs in serum/plasma in different diseases are conducted.

The research and development of a technology for detecting disease-related serum/plasma microRNAs. Specifically, the microRNAs with disease-related specificity changes are screened out, their primers are collected into a PCR kit (RT-PCR or Real-time PCR) to prepare a disease-diagnostic kit, or their reverse complementary sequences are dripped on chips as probes so as to prepare the biochips for detecting serum/plasma microRNAs specific for a certain disease.

Presently, the technologies of traditional biochemistry and molecular biology for the clinical diagnosis of diseases are relatively complicated and insensitive. Novel techniques developed in recent years possibly useful for disease diagnosis are gene chip technique, protein (antibody) chip technique, etc. The changes at mRNA level measured through gene chips cannot completely reflect the actual changes at protein level, since the bioactivity of protein is closely related to post-transcriptional modification such as glycosylation and phosphorylation. In addition, for detection of many diseases, marker molecules in body fluids and blood cannot be detected through gene chip technology. Meanwhile, protein (antibody) chip technique and proteomic techniques also bear their limitations. In human body, especially in serum/plasma, there are tens of thousands of protein and polypeptide segments with extensively distributed concentrations, and the number of proteins definitely reported is very small, let alone those quantified. It is an extremely arduous task to find out those proteins having close relation with specific diseases from the large quantity of proteins and understand their roles in histopathologic changes. Moreover, lacking of complete antibody resources is the bottleneck restraining the development of antibody biochip technology. The detection technology for serum/plasma microRNAs based on biochips of serum/plasma microRNAs and diagnostic kits skillfully combines the peculiar properties of serum/plasma microRNAs with conventional molecular biology detection technique together, which can rapidly analyze the respective constitution of serum/plasma microRNAs in respect of various diseases with high throughput and hence be of extremely clinical practicality. Since the changes of physiological conditions in organs and tissues will cause the constitutional changes of serum/plasma microRNAs, serum/plasma microRNAs can be used as "fingerprints for diseases" to realize early diagnosis of diseases.

The advantages of the technology of detecting serum/plasma microRNAs are as follows:

(1) As novel disease markers, serum/plasma microRNAs possess certain advantages such as extensive spectrum for detection, high sensitivity, low cost for detection, convenient sampling, easy preservation for samples (preserving serum/plasma at −20° C. will do), etc. This method can be widely used in general survey of diseases and other relevant tasks and has become an efficient means for early diagnosis of diseases.

(2) As novel disease markers, serum/plasma microRNAs will improve the low-specificity and low-sensitivity caused by individual differences which single markers are difficult to overcome, and notably increase the clinical detection rate of diseases so as to realize early diagnosis of diseases.

(3) The advantages of the technology of detecting serum/plasma microRNAs lie in that what to be detected is series of disease related markers, thus it can address the differences (i.e., age, sex, race, diet, circumstance, etc.) between individual patients, which are exactly a primary problem difficult to overcome by single disease markers.

In summary, utilizing the technology of detecting serum/plasma microRNAs can confirm diagnosis of histopathologic changes in early stage. These novel serum/plasma markers not only provide material foundation for people to comprehensively understand the mechanism of histopathologic changes in molecule level, but also accelerate the progress in diagnostics and therapeutics of clinical diseases. Of course, a majority of molecular diagnostic techniques used for disease detection in early period are at initial experimental stage and their validity needs to be further verified and improved. Moreover, since every disease has the characteristics of its own, this requires a peculiar method for the detection of said disease. In this manner, it is impossible for all diseases to be detected out only through one or only a few of detection methods. Nevertheless, based on the superiority of serum/plasma microRNAs, it is believed that, in the near future, the diagnostic technique of serum/plasma microRNAs for severe diseases such as cancer will become part of routine physical examination. In addition, microRNA related gene therapy will be widely utilized. Consequently, the overcoming of these diseases will come true, not just a dream.

BRIEF DESCRIPTION OF THE DRAWINGS

The following are the detailed description of the embodiments of this invention with reference to the drawings, wherein:

In FIG. 1 and FIG. 2, U6 is a snRNA with a molecular weight of 100 bp, serving as an internal reference molecule in microRNAs experiments. The rest of 12 microRNAs are each miR-181a(181a), miR-181b(181b), miR-223(223), miR-142-3p(142-3p), miR-142-5p(142-5p), miR-150(150) with blood cell specificity; miR-1(1), miR-133a(133a), miR-206(206) from cardiac muscles and skeletal muscles; miR-9(9), miR-124a(124a) from brain tissues; and miR-122a (122a) from liver.

THE BEST MODE FOR CARRYING OUT THE INVENTION

EXAMPLE 1

The RT-PCR Experiments of MicroRNAs in Serum/Plasma

Figure 1:
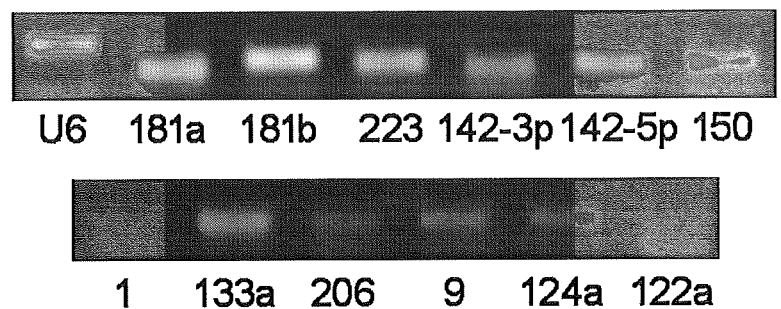
FIG. 1 shows the RT-PCR result of partial microRNAs directly detected in the serum of a normal person.

By using RT-PCR technique, it is found and proved that there stably exist various microRNAs in serum/plasma of both human beings and animals, and that their expression levels are considerably high. The specific RT-PCR steps are as follows:

(1) collecting serum/plasma of mice, rats, normal persons and some patients;

(2) preparing samples of cDNA. This operation has two options: one is to directly conduct reverse transcription reaction using 10 μl of serum/plasma; the other is to firstly extract the total RNA from serum/plasma (usually, about 10 μg of RNA can be enriched from 10 ml of serum/plasma) with Trizol reagent (Invitrogen Co.), subsequently obtain cDNA through RNA reverse transcription reaction. The reaction system of reverse transcription includes 4 μl 5×AMV buffer, 2 μl 10 mM each dNTP mixture (Takara Co.), 0.5 μl RNase Inhibitor (Takara Co.), 2 μl AMV (Takara Co.) and 1.50 gene specific reverse primers mixtures. The reaction steps successively include 15 minutes of incubation at 16, 1 hour of reaction at 42 and 5 minutes of incubation at 85;

(3) PCR and Electrophoresis observation. The cDNA is diluted by 1/50. To 1 μl diluted cDNA are added 0.3 μl Taq polymerase (Takara Co.), 0.20 μl 10 μM forward primer, 0.2 μl 10 μM universal reverse primer, 1.2 μl 25 mM $MgCl_2$, 1.60 μl 2.5 mM each dNTP mixture (Takara Co.), 2 μl 10×PCR buffer, 13.5 μl $H_2O$, and PCR reaction is conducted in the 20 μl system. The PCR reaction is done under the following conditions: one cycle at 95 for 5 mins followed by 40 cycles at 95 for 15 seconds and 60 for 1 minute. 10 μl PCR product is subjected to 3% Agarose Gel Electrophoresis, which is observed under ultraviolet lamp after EB staining The detailed experimental results are shown in FIG. 1. FIG. 1 shows the experimental results of RT-PCR directly conducted on the serum of normal persons. The all over 500 mature microRNAs in human being are selected for conducting RT-PCR reaction, of which 12 microRNAs are shown in FIG. 1 and each miR-181a, miR-181b, miR-223, miR-142-3p, miR-142-5p, miR-150 with blood cell specificity; miR-1, miR-133a, miR-206 from cardiac muscles and skeletal muscles; miR-9 and miR-124a from brain tissues; and miR-122a from liver. It can be seen from the results that all microRNAs from the above-mentioned four tissues are detectable in blood, and that not all over 500 mature microRNAs have high expression level in the serum/plasma, with some microRNAs being in fairly trace amount and even being normally nondetectable.

Figure 2:
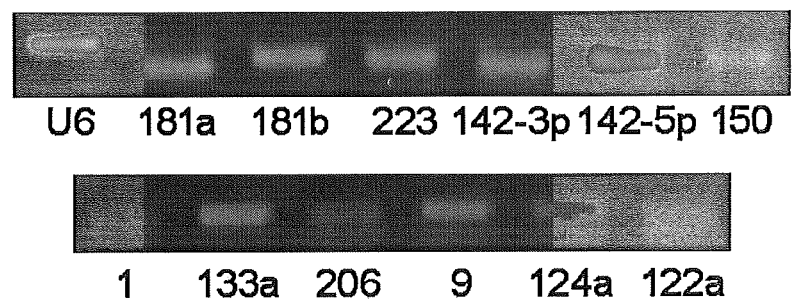
FIG. 2 shows the RT-PCR results of the microRNAs in the RNA extracted from the serum of a normal person.
Figure 3:
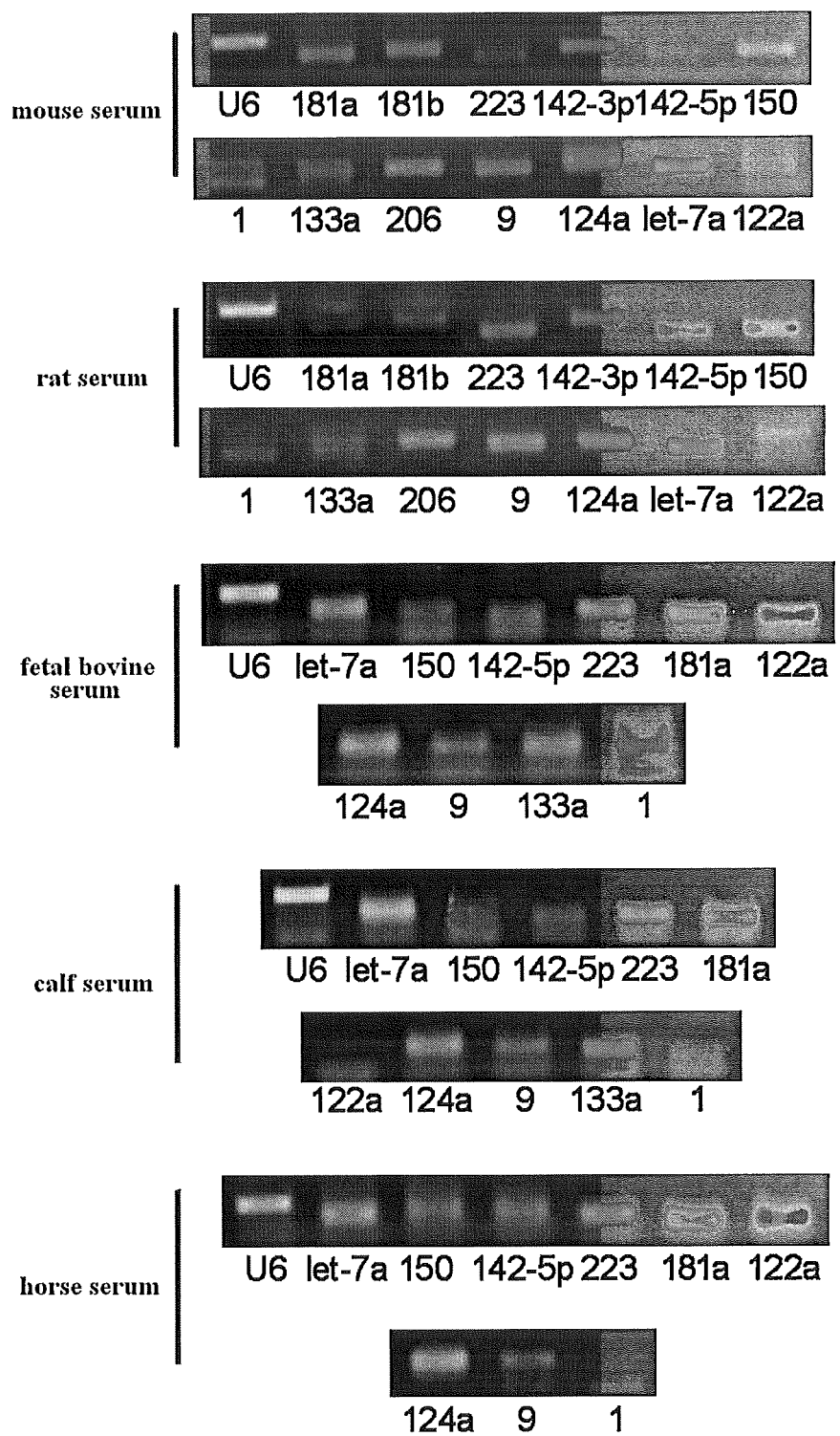
FIG. 3 shows the RT-PCR results of partial micro-RNAs directly detected in the serum of mouse, rat, fetal bovine, calf and horse respectively.

To further verify that there stably exist the microRNAs in serum/plasma, RNA is firstly extracted from the serum of normal persons, then all over 500 mature microRNAs of human are selected for PCR experiment. As shown in FIG. 2, the results of FIG. 2 is quite consistent with that of FIG. 1, the singleness of the PCR products indicating that both two assays can detect the expression and level of the microRNAs in people's serum/plasma, and proving that there stably exist microRNAs of various tissues sources in people's serum/plasma. In addition, the same method is used to detect the expression and level of over 500 microRNAs in the serum/plasma of mouse, rat, fetal bovine, calf and horse, it is also found that there is stable expression of microRNAs of various tissues sources in serum/plasma of mouse, rat, fetal bovine, calf and horse (see FIG. 3).

EXAMPLE 2

The Real-Time PCR Experiments of MicroRNAs in Serum/Plasma

Quantitative PCR experiments of microRNAs in serum/plasma are conducted to study the specific variation of microRNAs quantity in serum/plasma during the course of various diseases, including various tumors, various acute and chronic infectious diseases, e.g. viral diseases such as viral influenza, viral hepatitis, AIDS, SARS, bacterial diseases such as tuberculosis, bacterial pneumonia, and other acute and chronic infectious diseases caused by various pathogenic microorganisms; other acute and chronic diseases such as diseases of respiratory system, diseases of immune system, diseases of blood and hematopoietic system, diseases of circulatory system such as cardio-cerebrovascular disease, metabolic diseases of endocrine system, diseases of digestive system, diseases of nervous system, diseases of urinary system, diseases of reproductive system and diseases of locomotor system. The experimental principles and experimental steps of quantitative PCR are basically the same as those of RT-PCR, with the only difference between them being the addition of a fluorescent dye EVA GREEN in the process of PCR. An ABI Prism 7300 fluorescent quantitative PCR instrument is used to conduct PCR reaction under the following conditions: one cycle at 95° C. for 5 mins followed by 40 cycles at 95° C. for 15 seconds and 60° C. for 1 minute. The data processing method used is ΔΔCT method, wherein CT is the number of cycles when the reaction reaches the threshold. The expression level of each microRNAs relative to that of internal standard reference can be expressed by the equation of 2-ΔCT, wherein $\Delta CT = CT_{sample} - CT_{Internal\ reference}$. Reverse transcription reactions are directly conducted on serum/plasma samples of a patient and those of a normal person, and the quantities of microRNAs contained in each sample of serum/plasma are compared through quantitative PCR reactions.

Figure 4:
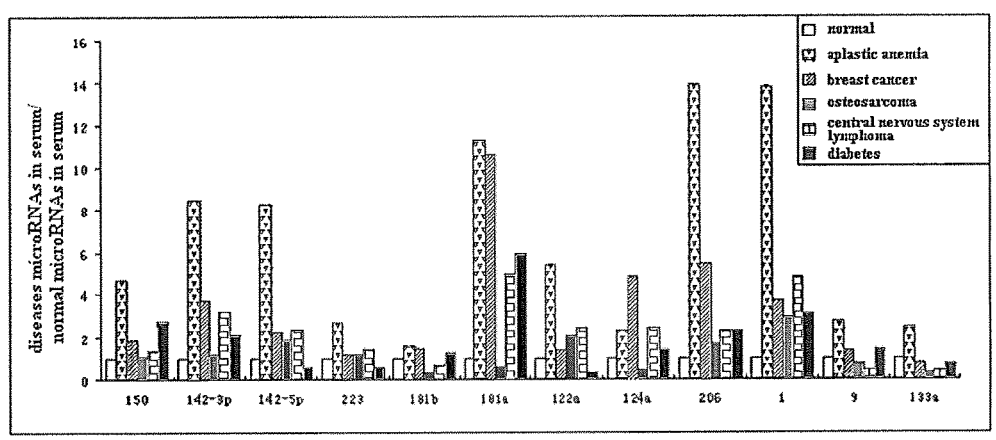
FIG. 4 shows the variable quantity of the partial microRNAs in the serum of a patient suffering from the shown diseases compared with microRNAs in the serum of a normal person.

Serum samples of patients who suffer from aplastic anemia, breast cancer, osteosarcoma, CNS (Central Nervous System) lymphoma, diabetes are selected, and at the same time, all over 500 mature microRNAs of human beings are used to conduct PCR reaction experiments. FIG. 4 shows the quantitative PCR experimental results of microRNAs within serum of patients and normal persons which include the above-mentioned miR-181a, miR-181b, miR-223, miR-142-3p, miR-142-5p, miR-150 with blood cell specificity; miR-1, miR-133a, miR-206 from cardiac muscles and skeletal muscles; miR-9, miR-124a from brain tissues; and miR-122a from liver. The ratio of the microRNAs quantity in serum between normal persons and patients suffering from aplastic anemia, breast cancer, osteosarcoma, CNS (Central Nervous System) lymphoma, diabetes are respectively up-regulated or down-regulated, and the variation extent of the microRNAs quantity from the same tissue source differs in patients with different diseases, indicating that there is specificity variation of microRNAs quantity in the serum/plasma of patients with different diseases. They can be taken as a type of novel markers for disease diagnosis.

Example 3

The Superiority of Serum/Plasma MicroRNAs as Disease Markers

Figure 5:
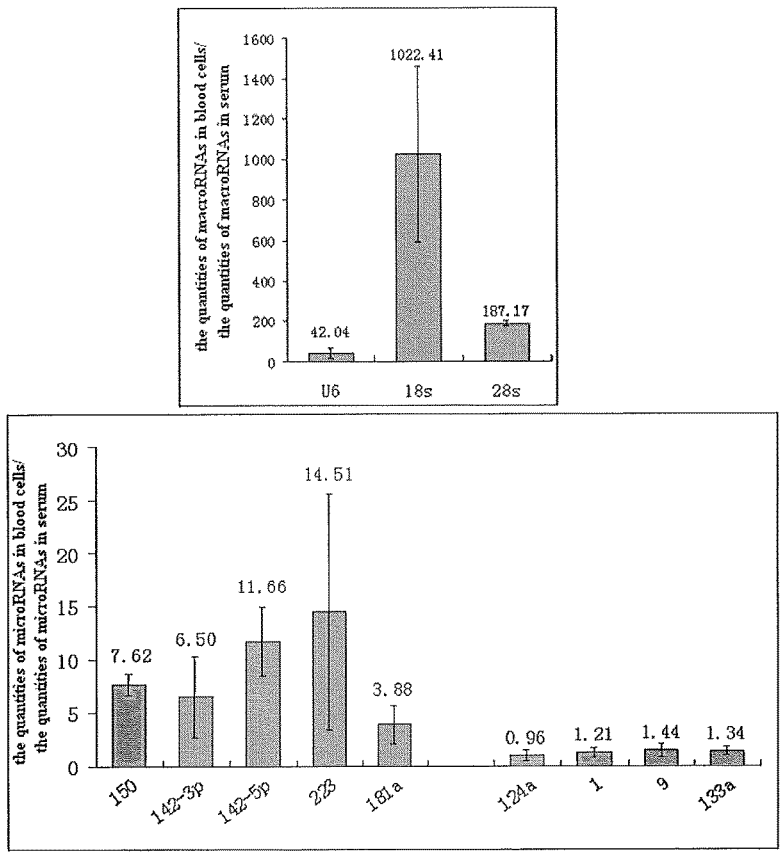
FIG. 5 shows the ratio between the quantities of macroRNAs and microRNAs in blood cells and serum.

Through detecting the quantities of microRNAs and macroRNAs in serum and blood cells, it is found that there is an abundant content of microRNAs in serum. See FIG. 5. As represented by U6 molecules with a molecular weight of 100 bp and ribosomal RNA molecules with molecular weights being 18 S and 28 S respectively, the quantity of macroRNAs in blood cells is at least tens times that in serum; while the quantity of microRNAs in serum remains the same as that in blood cells except the microRNAs with blood cell specificity. Therefore, serum/plasma will specifically enrich small molecule RNAs, especially microRNAs.

It is also found that microRNAs are to some extent able to resist the action of endonuclease, which is possibly one of the reasons why microRNAs can stably exist in serum/plasma. Total RNAs extracted from cultured cell line are processed with endonuclease RNase A and the remaining quantity of macroRNAs and microRNAs are then detected.

Figure 6:
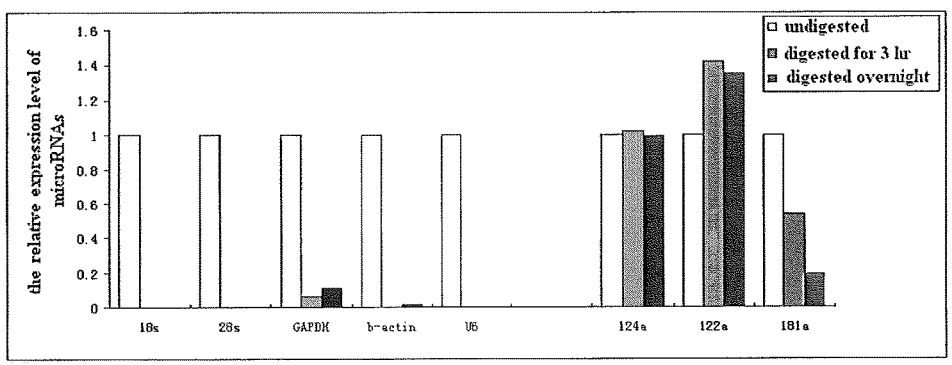
FIG. 6 shows the enzyme digested results of macroRNAs and microRNAs.

As shown in FIG. 6, it is found that microRNAs can to some extent resist the degradation of endonuclease while the macroRNAs are substantially completely cut off. Therefore microRNAs can stably exist in serum/plasma.

Based on the two characteristics of abundance in content and stable existence of microRNAs in serum/plasma, microRNAs could be well applied in clinical test.

EXAMPLE 4

Preparation of the Biochip of Serum/Plasma MicroRNAs Useful for Disease Diagnosis A biochip of serum/plasma microRNAs is fabricated to verify the reliability of a kind of serum/plasma microRNAs probes relating to diseases which are selected through quantitative PCR method. The biochip contains all microRNAs probes that can be normally detected in people's serum/plasma, constituting a probe library. See Table 1.

When the probes are specifically applied in certain disease diagnosis or efficacy screening, some probes of the probe library are put together to construct a probe collection which makes it possible to quantitatively detect the variation of microRNAs in the specific conditions. For example, when diagnosing colon cancer, the collection of probes that have interaction with microRNAs of numbers 17-5p, 21, 103, 106a, 107, 126*, 143, 145, 150, 155 and 210 is used. For another example, when diagnosing myocardial hypertrophy and chronic heart failure, the collection of probes that have interaction with microRNAs of numbers 21, 23a, 23b, 24, 27a, 27b, 125b, 195, 199a, 214, 217, 133a is used. In addition, the chip can also do high-throughput screening of the probes of microRNAs varying stably in serum/plasma, and diseases can be predicted and diagnosed based on the overall variation of microRNAs in serum/plasma.

Sequencing method or quantitative PCR method is firstly used to determine that there is more than one copy of microRNAs in serum/plasma, and then reverse complementary probes of these microRNAs are synthesized, after which these probes are spotted on a chemically-modified slide in a size of 75×25 mm using a biochip microarrayer SmartArray™. The samples spotted on the chip also include U6 and tRNA as internal standard, artificially-prepared external standard in length of 30 bases, Hex as positive control etc. The entire lattice is divided into 4 sub-lattices and each sub-lattice has 23 rows and 21 columns, wherein the spot distance is 185 μm and the spot diameter is about 130 μm and each probe was repeatedly spotted for 3 times.

The operational procedure of the biochip is: (1) extracting the total RNA from serum/plasma and detecting its quality through formaldehyde denaturing gel electrophoresis; (2) separation of microRNAs: 50-100 μg total RNA is taken to separate microRNAs from total RNA with Ambion's miRNA Isolation Kit (Cat #. 1560); (3) fluorescently-labeling of microRNAs samples: microRNAs samples are fluorescently-labeling with T4 RNA ligase, then precipitated with absolute ethanol, and then blown to dryness for chip hybridization; (4) hybridization and cleaning: RNA is dissolved into 164, hybridizing solution (15% formamide, 0.2% SDS, 3×SSC and 50×Denhardt's solution), and hybridized at 42 overnight. After completion of the hybridization, it is washed in a solution containing 0.2% SDS and 2×SSC at about 42 for 4 minutes, and then washed in a solution containing 0.2×SSC at room temperature for 4 minutes. Thereafter, the slides can be used for scanning immediately after being dried; (5) chip scanning: the chip is scanned with two-channel laser scanner LuxScan 10K/A; (6)

data extracting and analysis: the chip image is analyzed with an image analyzing software LuxScan 3.0, the image signal is transformed into digital signal, and finally differentially-expressed genes are analyzed and selected with SAM method.

A biochip is prepared as above by using a kind of serum/plasma microRNAs probes which express greatly differently under disease condition and normal physiological condition double-verified by quantitative PCR technique and biochip technique. As compared with the traditional chip, there is no significant improvement in the manufacturing process and operational procedure of this biochip, but this chip simplifies the probe library, thereby greatly reducing the manufacturing cost and production time of the chip, and hence is easy to prepare. Meanwhile it increases the pertinence and practicability of chip. The application of the chip in practice can detect diseases in an early phase with only need of the serum/plasma of a patient and no need of other tissues, which helps guide the diagnosis and treatment.

EXAMPLE 5

Preparation of Kits of MicroRNAs Useful for Disease Diagnosis and Prediction

The manufacturing processed and operational procedures of microRNAs kits useful for diagnosis, prediction of complication occurrence and malignant disease relapse, evaluation of therapeutic effects, screening of pharmaceutical active ingredients, assessment of drug efficacy, forensic authentication and prohibited drug inspection, etc. of all diseases are based on quantitative PCR technique and semi-quantitative PCR technique and biochip technique. The above-mentioned diseases include various tumors; various acute/chronic infectious diseases, e.g. viral diseases such as viral influenza, viral hepatitis, AIDS, SARS, bacterial diseases such as tuberculosis, bacterial pneumonia, and other acute/chronic infectious diseases caused by various pathogenic microorganisms; other acute/chronic diseases such as diseases of respiratory system, diseases of immune system, diseases of blood and hematopoietic system, diseases of circulatory system such as cardio-cerebrovascular diseases, metabolic diseases of endocrine system, diseases of digestive system, diseases of nervous system, diseases of urinary system, diseases of reproductive system and diseases of locomotor system.

Sequencing method or quantitative PCR method is firstly used to determine that there is more than one copy of microRNAs in serum/plasma. Then, a kind of serum/plasma mircoRNAs that have a big difference between the expression levels in disease condition and in normal physiological condition are screened out through the techniques of quantitative PCR and biochip, which are taken as an indicator for predicting whether canceration or other disease occurs and diagnosing the pathological degree. Finally the number of screened corresponding serum/plasma microRNAs of each disease would be controlled to over ten to tens, which is the optimized condensement of the chip-probe library. The kit contains a batch of serum/plasma mircoRNAs primers, Taq polymerase, dNTP, etc. The value of the kit lies in making it possible to detect the changing trend of microRNAs through the most simplified probe library and with only need of serum/plasma and no need of any other tissue samples, and further predict the probability of occurrence of diseases or diagnose the pathological phase of diseases based on this changing trend detected. Thus, the application of this kit in practice can increase the possibility of discovering diseases in an early phase, which helps guide the diagnosis and treatment of diseases.

The invention claimed is:

1. A kit for evaluating a pathological condition of a subject, wherein the kit comprises:
   (a) tools useful for dephosphorylating a microRNA,
   (b) tools useful for artificially extending dephosphorylated microRNA, and
   (c) probes that detect cDNAs of a combination of miRNAs from serum/plasma of the subject,
      wherein the combination of miRNAs comprises miR-181a, miR-181b, miR-223, miR-142-3p, miR-142-5p, miR-150, miR-1, miR-133a, miR-206, miR-9, miR-124a, and miR-122a,
      wherein each of the probes is fluorescently labeled, and
      wherein the cDNAs detected by the fluorescently labeled probes are indicative of dephosphorylated microRNAs stably existing in the serum/plasma of the subject.

2. The kit according to claim 1, wherein said evaluating the pathological condition of the subject is to determine the pathological condition of the subject after being administrated a test sample.

3. The kit according to claim 2, wherein the kit is useful for screening the test sample during treatment of the pathological condition.

4. The kit according to claim 1, wherein said evaluating the pathological condition of the subject is to diagnose the pathological condition of the subject.

5. The kit according to claim 1, wherein said evaluating the pathological condition of the subject is to evaluate effectiveness of treating the pathological condition of the subject.

6. The kit according to claim 1, wherein said evaluating the pathological condition of the subject is to predict an occurrence of a disease of the subject.

7. The kit according to claim 6, wherein the occurrence of the disease is the occurrence of a complication and/or relapse of a malignant disease.

8. The kit according to claim 6, wherein the disease is a tumor.

9. The kit according to claim 1, wherein the serum/plasma of the subject are from living bodies, tissues, organs, and/or corpuses of the subject.

10. A kit for evaluating a pathological condition of a subject,
   wherein the kit comprises an endonuclease and tools useful for determining all detectable endonuclease-resistant, dephosphorylated and artificially extended microRNAs stably existing in serum/plasma of the subject, and to add a detectable probe,
   wherein the kit also comprises probes that detect cDNAs of a combination of miRNAs, wherein the combination of miRNAs comprises let-7a, let-7b, let-7c, let-7d, let-7e, let-7f, let-7g, let-7i, miR-1, miR-100, miR-101, miR-103, miR-105, miR-106a, miR-106b, miR-107, miR-10a, miR-10b, miR-122a, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-142-5p, miR-143, miR-144, miR-145, miR-146a, miR-146b, miR-147, miR-148a, miR-148b, miR-149, miR-150, miR-151, miR-152, miR-153, miR-154, miR-154*, miR-155, miR-15a, miR-15b, miR-16, miR-17-3p, miR-17-5p, miR-181a, miR-181b, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193a, miR-193b, miR-194, miR-195, miR-196a, miR-196b, miR-197, miR-198, miR-199a, miR-199a*, miR-199b, miR-19a, miR-19b, miR-200a, miR-200a*, miR-200b, miR-200c, miR-202, miR-202*, miR-203, miR-204, miR-205, miR-206, miR-208, miR-20a, miR-20b, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-483, miR-484, miR-485-3p, miR-485-5p, miR-486, miR-487a, miR-487b, miR-488, miR-489, miR-490, miR-491 miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548d, miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591 miR-592, miR-593, miR-594, miR-595, miR-596, miR-597, miR-598, miR-599, miR-600, miR-601, miR-602, miR-603, miR-604, miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-7, miR-9, miR-9*, miR-92, miR-93, miR-95, miR-96, miR-98, miR-99a and miR-99b, and wherein each of the probes is fluorescently labeled.

11. The kit of claim 10, further comprising reagents to artificially extend endonuclease resistant, dephosphorylated microRNAs.

12. The kit of claim 10, further comprising reagents to add fluorescent labels to endonuclease resistant, dephosphorylated microRNAs.

13. The kit of claim 10, wherein the probes are SEQ ID NO:1 to 451.

14. The kit according to claim 1, wherein the combination of miRNAs further comprises miR-193a, miR-7, miR-214, miR-483, and miR-25.

15. The kit according to claim 14, wherein the combination of miRNAs further comprises miR-17-5p, miR-21, miR-103, miR-106a, miR-107, miR-126*, miR-143, miR-145, miR-155, miR-23a, miR-23b, miR-24, miR-27a, miR-27b, miR-125b, miR-195, miR-199a, and miR-217.

16. The kit according to claim 15, wherein the combination of miRNAs further comprises let-7a, let-7b, let-7c, let-7d, let-7e, let-7f, let-7g, let-7i, miR-100, miR-101, miR-105, miR-106b, miR-10a, miR-10b, miR-125a, miR-126, miR-127, miR-128a, miR-128b, miR-129, miR-130a, miR-130b, miR-132, miR-133b, miR-134, miR-135a, miR-135b, miR-136, miR-137, miR-138, miR-139, miR-140, miR-141, miR-144, miR-146a, miR-146b, miR-147, miR-148a, miR-148b, miR-149, miR-151, miR-152, miR-153, miR-154, miR-154*, miR-15a, miR-15b, miR-16, miR-17-3p, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193b, miR-194, miR-196a, miR-196b, miR-197, miR-198, miR-199a*, miR-199b, miR-19a, miR-19b, miR-200a, miR-200a*, miR-200b, miR-200c, miR-202, miR-202*, miR-203, miR-204, miR-205, miR-208, miR-20a, miR-20b, miR-210, miR-211 miR-212, miR-213, miR-215, miR-216, miR-218, miR-219, miR-22, miR-220, miR-221 miR-222, miR-224, miR-26a, miR-26b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-484, miR-485-3p, miR-485-5p, miR-486, miR-487a, miR-487b, miR-488, miR-489, miR-490, miR-491 miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548d, miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591 miR-592, miR-593, miR-594, miR-595, miR-596, miR-597, miR-598, miR-599, miR-600, miR-601, miR-602, miR-603, miR-604., miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-9*, miR-92, miR-93, miR-95, miR-96, miR-98, miR-99a and miR-99b.

* * * * *

SEQUENCE LISTING

```
<160> NUMBER OF SEQ ID NOS: 451

<210> SEQ ID NO 1
<211> LENGTH: 22
<212> TYPE: DNA
<213> ORGANISM: Artificial Sequence
<220> FEATURE:
<223> OTHER INFORMATION: Synthetic Probe

<400> SEQUENCE: 1
aactatacaa cctactacct ca                                             22

<210> SEQ ID NO 2
<211> LENGTH: 22
<212> TYPE: DNA
<213> ORGANISM: Artificial Sequence
<220> FEATURE:
<223> OTHER INFORMATION: Synthetic Probe

<400> SEQUENCE: 2
aaccacacaa cctactacct ca                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic Probe
```

```
<400> SEQUENCE: 3
aaccatacaa cctactacct ca                                        22

<210> SEQ ID NO 4
<211> LENGTH: 21
<212> TYPE: DNA
<213> ORGANISM: Artificial Sequence
<220> FEATURE:
<223> OTHER INFORMATION: Synthetic Probe

<400> SEQUENCE: 4
actatgcaac ctactacctc t                                         21

<210> SEQ ID NO 5
<211> LENGTH: 21
<212> TYPE: DNA
<213> ORGANISM: Artificial Sequence
<220> FEATURE:
<223> OTHER INFORMATION: Synthetic Probe

<400> SEQUENCE: 5
actatacaac ctcctacctc a                                         21

<210> SEQ ID NO 6
<211> LENGTH: 22
<212> TYPE: DNA
<213> ORGANISM: Artificial Sequence
<220> FEATURE:
<223> OTHER INFORMATION: Synthetic Probe

<400> SEQUENCE: 6
aactatacaa tctactacct ca                                        22

<210> SEQ ID NO 7
<211> LENGTH: 21
<212> TYPE: DNA
<213> ORGANISM: Artificial Sequence
<220> FEATURE:
<223> OTHER INFORMATION: Synthetic Probe

<400> SEQUENCE: 7
actgtacaaa ctactacctc a                                         21

<210> SEQ ID NO 8
<211> LENGTH: 21
<212> TYPE: DNA
<213> ORGANISM: Artificial Sequence
<220> FEATURE:
<223> OTHER INFORMATION: Synthetic Probe

<400> SEQUENCE: 8
acagcacaaa ctactacctc a                                         21

<210> SEQ ID NO 9
<211> LENGTH: 21
<212> TYPE: DNA
<213> ORGANISM: Artificial Sequence
<220> FEATURE:
<223> OTHER INFORMATION: Synthetic Probe

<400> SEQUENCE: 9
tacatacttc tttacattcc a                                         21

<210> SEQ ID NO 10
<211> LENGTH: 22
```

```
<212> TYPE: DNA
<213> ORGANISM: Artificial Sequence
<220> FEATURE:
<223> OTHER INFORMATION: Synthetic Probe

<400> SEQUENCE: 10
cacaagttcg gatctacggg tt                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Probe

<400> SEQUENCE: 11
cttcagttat cacagtactg ta                                              22

<210> SEQ ID NO 12
<211> LENGTH: 23
<212> TYPE: DNA
<213> ORGANISM: Artificial Sequence
<220> FEATURE:
<223> OTHER INFORMATION: Synthetic Probe

<400> SEQUENCE: 12
tcatagccct gtacaatgct gct                                             23

<210> SEQ ID NO 13
<211> LENGTH: 20
<212> TYPE: DNA
<213> ORGANISM: Artificial Sequence
<220> FEATURE:
<223> OTHER INFORMATION: Synthetic Probe

<400> SEQUENCE: 13
acaggagtct gagcatttga                                                 20

<210> SEQ ID NO 14
<211> LENGTH: 24
<212> TYPE: DNA
<213> ORGANISM: Artificial Sequence
<220> FEATURE:
<223> OTHER INFORMATION: Synthetic Probe

<400> SEQUENCE: 14
gctacctgca ctgtaagcac tttt                                            24

<210> SEQ ID NO 15
<211> LENGTH: 21
<212> TYPE: DNA
<213> ORGANISM: Artificial Sequence
<220> FEATURE:
<223> OTHER INFORMATION: Synthetic Probe

<400> SEQUENCE: 15
atctgcactg tcagcacttt a                                               21

<210> SEQ ID NO 16
<211> LENGTH: 23
<212> TYPE: DNA
<213> ORGANISM: Artificial Sequence
<220> FEATURE:
<223> OTHER INFORMATION: Synthetic Probe

<400> SEQUENCE: 16
```

```
tgatagccct gtacaatgct gct                                             23
```

<210> SEQ ID NO 17
<211> LENGTH: 23
<212> TYPE: DNA
<213> ORGANISM: Artificial Sequence
<220> FEATURE:
<223> OTHER INFORMATION: Synthetic Probe

<400> SEQUENCE: 17

```
cacaaattcg gatctacagg gta                                             23
```

<210> SEQ ID NO 18
<211> LENGTH: 22
<212> TYPE: DNA
<213> ORGANISM: Artificial Sequence
<220> FEATURE:
<223> OTHER INFORMATION: Synthetic Probe

<400> SEQUENCE: 18

```
acaaattcgg ttctacaggg ta                                              22
```

<210> SEQ ID NO 19
<211> LENGTH: 23
<212> TYPE: DNA
<213> ORGANISM: Artificial Sequence
<220> FEATURE:
<223> OTHER INFORMATION: Synthetic Probe

<400> SEQUENCE: 19

```
acaaacacca ttgtcacact cca                                             23
```

<210> SEQ ID NO 20
<211> LENGTH: 22
<212> TYPE: DNA
<213> ORGANISM: Artificial Sequence
<220> FEATURE:
<223> OTHER INFORMATION: Synthetic Probe

<400> SEQUENCE: 20

```
tggcattcac cgcgtgcctt aa                                              22
```

<210> SEQ ID NO 21
<211> LENGTH: 23
<212> TYPE: DNA
<213> ORGANISM: Artificial Sequence
<220> FEATURE:
<223> OTHER INFORMATION: Synthetic Probe

<400> SEQUENCE: 21

```
cacaggttaa agggtctcag gga                                             23
```

<210> SEQ ID NO 22
<211> LENGTH: 22
<212> TYPE: DNA
<213> ORGANISM: Artificial Sequence
<220> FEATURE:
<223> OTHER INFORMATION: Synthetic Probe

<400> SEQUENCE: 22

```
tcacaagtta gggtctcagg ga                                              22
```

<210> SEQ ID NO 23
<211> LENGTH: 21
<212> TYPE: DNA
<213> ORGANISM: Artificial Sequence

```
<220> FEATURE:
<223> OTHER INFORMATION: Synthetic Probe

<400> SEQUENCE: 23
gcattattac tcacggtacg a                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Probe

<400> SEQUENCE: 24
cgcgtaccaa aagtaataat g                                              21

<210> SEQ ID NO 25
<211> LENGTH: 22
<212> TYPE: DNA
<213> ORGANISM: Artificial Sequence
<220> FEATURE:
<223> OTHER INFORMATION: Synthetic Probe

<400> SEQUENCE: 25
agccaagctc agacggatcc ga                                             22

<210> SEQ ID NO 26
<211> LENGTH: 22
<212> TYPE: DNA
<213> ORGANISM: Artificial Sequence
<220> FEATURE:
<223> OTHER INFORMATION: Synthetic Probe

<400> SEQUENCE: 26
aaaagagacc ggttcactgt ga                                             22

<210> SEQ ID NO 27
<211> LENGTH: 22
<212> TYPE: DNA
<213> ORGANISM: Artificial Sequence
<220> FEATURE:
<223> OTHER INFORMATION: Synthetic Probe

<400> SEQUENCE: 27
gaaagagacc ggttcactgt ga                                             22

<210> SEQ ID NO 28
<211> LENGTH: 21
<212> TYPE: DNA
<213> ORGANISM: Artificial Sequence
<220> FEATURE:
<223> OTHER INFORMATION: Synthetic Probe

<400> SEQUENCE: 28
gcaagcccag accgcaaaaa g                                              21

<210> SEQ ID NO 29
<211> LENGTH: 22
<212> TYPE: DNA
<213> ORGANISM: Artificial Sequence
<220> FEATURE:
<223> OTHER INFORMATION: Synthetic Probe

<400> SEQUENCE: 29
atgccctttt aacattgcac tg                                             22
```

<210> SEQ ID NO 30
<211> LENGTH: 22
<212> TYPE: DNA
<213> ORGANISM: Artificial Sequence
<220> FEATURE:
<223> OTHER INFORMATION: Synthetic Probe

<400> SEQUENCE: 30 atgcccttc atcattgcac tg                                    22

<210> SEQ ID NO 31
<211> LENGTH: 22
<212> TYPE: DNA
<213> ORGANISM: Artificial Sequence
<220> FEATURE:
<223> OTHER INFORMATION: Synthetic Probe

<400> SEQUENCE: 31
cgaccatggc tgtagactgt ta                                   22

<210> SEQ ID NO 32
<211> LENGTH: 22
<212> TYPE: DNA
<213> ORGANISM: Artificial Sequence
<220> FEATURE:
<223> OTHER INFORMATION: Synthetic Probe

<400> SEQUENCE: 32
acagctggtt gaagggacc aa                                    22

<210> SEQ ID NO 33
<211> LENGTH: 21
<212> TYPE: DNA
<213> ORGANISM: Artificial Sequence
<220> FEATURE:
<223> OTHER INFORMATION: Synthetic Probe

<400> SEQUENCE: 33
tagctggttg aaggggacca a                                    21

<210> SEQ ID NO 34
<211> LENGTH: 21
<212> TYPE: DNA
<213> ORGANISM: Artificial Sequence
<220> FEATURE:
<223> OTHER INFORMATION: Synthetic Probe

<400> SEQUENCE: 34
ccctctggtc aaccagtcac a                                    21

<210> SEQ ID NO 35
<211> LENGTH: 23
<212> TYPE: DNA
<213> ORGANISM: Artificial Sequence
<220> FEATURE:
<223> OTHER INFORMATION: Synthetic Probe

<400> SEQUENCE: 35
tcacatagga ataaaaagcc ata                                  23

<210> SEQ ID NO 36
<211> LENGTH: 22
<212> TYPE: DNA
<213> ORGANISM: Artificial Sequence
<220> FEATURE:
<223> OTHER INFORMATION: Synthetic Probe

<400> SEQUENCE: 36
cacataggaa tgaaaagcca ta                                    22

<210> SEQ ID NO 37
<211> LENGTH: 23
<212> TYPE: DNA
<213> ORGANISM: Artificial Sequence
<220> FEATURE:
<223> OTHER INFORMATION: Synthetic Probe

<400> SEQUENCE: 37
tccatcatca aaacaaatgg agt                                   23

<210> SEQ ID NO 38
<211> LENGTH: 22
<212> TYPE: DNA
<213> ORGANISM: Artificial Sequence
<220> FEATURE:
<223> OTHER INFORMATION: Synthetic Probe

<400> SEQUENCE: 38
ctacgcgtat tcttaagcaa ta                                    22

<210> SEQ ID NO 39
<211> LENGTH: 17
<212> TYPE: DNA
<213> ORGANISM: Artificial Sequence
<220> FEATURE:
<223> OTHER INFORMATION: Synthetic Probe

<400> SEQUENCE: 39
gattcacaac accagct                                          17

<210> SEQ ID NO 40
<211> LENGTH: 18
<212> TYPE: DNA
<213> ORGANISM: Artificial Sequence
<220> FEATURE:
<223> OTHER INFORMATION: Synthetic Probe

<400> SEQUENCE: 40
agacacgtgc actgtaga                                         18

<210> SEQ ID NO 41
<211> LENGTH: 21
<212> TYPE: DNA
<213> ORGANISM: Artificial Sequence
<220> FEATURE:
<223> OTHER INFORMATION: Synthetic Probe

<400> SEQUENCE: 41
ctaccatagg gtaaaaccac t                                     21

<210> SEQ ID NO 42
<211> LENGTH: 22
<212> TYPE: DNA
<213> ORGANISM: Artificial Sequence
<220> FEATURE:
<223> OTHER INFORMATION: Synthetic Probe

<400> SEQUENCE: 42
ccatctttac cagacagtgt ta                                    22

<210> SEQ ID NO 43

<211> LENGTH: 23
<212> TYPE: DNA
<213> ORGANISM: Artificial Sequence
<220> FEATURE:
<223> OTHER INFORMATION: Synthetic Probe

<400> SEQUENCE: 43
tccataaagt aggaaacact aca                                    23

<210> SEQ ID NO 44
<211> LENGTH: 20
<212> TYPE: DNA
<213> ORGANISM: Artificial Sequence
<220> FEATURE:
<223> OTHER INFORMATION: Synthetic Probe

<400> SEQUENCE: 44
gtagtgcttt ctactttatg                                        20

<210> SEQ ID NO 45
<211> LENGTH: 22
<212> TYPE: DNA
<213> ORGANISM: Artificial Sequence
<220> FEATURE:
<223> OTHER INFORMATION: Synthetic Probe

<400> SEQUENCE: 45
tgagctacag tgcttcatct ca                                     22

<210> SEQ ID NO 46
<211> LENGTH: 22
<212> TYPE: DNA
<213> ORGANISM: Artificial Sequence
<220> FEATURE:
<223> OTHER INFORMATION: Synthetic Probe

<400> SEQUENCE: 46
ctagtacatc atctatactg ta                                     22

<210> SEQ ID NO 47
<211> LENGTH: 24
<212> TYPE: DNA
<213> ORGANISM: Artificial Sequence
<220> FEATURE:
<223> OTHER INFORMATION: Synthetic Probe

<400> SEQUENCE: 47
aagggattcc tgggaaaact ggac                                   24

<210> SEQ ID NO 48
<211> LENGTH: 22
<212> TYPE: DNA
<213> ORGANISM: Artificial Sequence
<220> FEATURE:
<223> OTHER INFORMATION: Synthetic Probe

<400> SEQUENCE: 48
aacccatgga attcagttct ca                                     22

<210> SEQ ID NO 49
<211> LENGTH: 22
<212> TYPE: DNA
<213> ORGANISM: Artificial Sequence
<220> FEATURE:
<223> OTHER INFORMATION: Synthetic Probe

<400> SEQUENCE: 49
agcctatgga attcagttct ca                                              22

<210> SEQ ID NO 50
<211> LENGTH: 20
<212> TYPE: DNA
<213> ORGANISM: Artificial Sequence
<220> FEATURE:
<223> OTHER INFORMATION: Synthetic Probe

<400> SEQUENCE: 50
gcagaagcat ttccacacac                                                 20

<210> SEQ ID NO 51
<211> LENGTH: 22
<212> TYPE: DNA
<213> ORGANISM: Artificial Sequence
<220> FEATURE:
<223> OTHER INFORMATION: Synthetic Probe

<400> SEQUENCE: 51
acaaagttct gtagtgcact ga                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic Probe

<400> SEQUENCE: 52
acaaagttct gtgatgcact ga                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic Probe

<400> SEQUENCE: 53
ggagtgaaga cacggagcca ga                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Probe

<400> SEQUENCE: 54
cactggtaca agggttggga ga                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic Probe

<400> SEQUENCE: 55
cctcaaggag cttcagtcta gt                                              22

<210> SEQ ID NO 56
<211> LENGTH: 22
<212> TYPE: DNA

```
<213> ORGANISM: Artificial Sequence
<220> FEATURE:
<223> OTHER INFORMATION: Synthetic Probe

<400> SEQUENCE: 56
cccaagttct gtcatgcact ga                                              22

<210> SEQ ID NO 57
<211> LENGTH: 20
<212> TYPE: DNA
<213> ORGANISM: Artificial Sequence
<220> FEATURE:
<223> OTHER INFORMATION: Synthetic Probe

<400> SEQUENCE: 57
tcacttttgt gactatgcaa                                                 20

<210> SEQ ID NO 58
<211> LENGTH: 22
<212> TYPE: DNA
<213> ORGANISM: Artificial Sequence
<220> FEATURE:
<223> OTHER INFORMATION: Synthetic Probe

<400> SEQUENCE: 58
cgaaggcaac acggataacc ta                                              22

<210> SEQ ID NO 59
<211> LENGTH: 22
<212> TYPE: DNA
<213> ORGANISM: Artificial Sequence
<220> FEATURE:
<223> OTHER INFORMATION: Synthetic Probe

<400> SEQUENCE: 59
aataggtcaa ccgtgtatga tt                                              22

<210> SEQ ID NO 60
<211> LENGTH: 22
<212> TYPE: DNA
<213> ORGANISM: Artificial Sequence
<220> FEATURE:
<223> OTHER INFORMATION: Synthetic Probe

<400> SEQUENCE: 60
cccctatcac gattagcatt aa                                              22

<210> SEQ ID NO 61
<211> LENGTH: 22
<212> TYPE: DNA
<213> ORGANISM: Artificial Sequence
<220> FEATURE:
<223> OTHER INFORMATION: Synthetic Probe

<400> SEQUENCE: 61
cacaaaccat tatgtgctgc ta                                              22

<210> SEQ ID NO 62
<211> LENGTH: 22
<212> TYPE: DNA
<213> ORGANISM: Artificial Sequence
<220> FEATURE:
<223> OTHER INFORMATION: Synthetic Probe

<400> SEQUENCE: 62
tgtaaaccat gatgtgctgc ta                                              22
```

<210> SEQ ID NO 63
<211> LENGTH: 22
<212> TYPE: DNA
<213> ORGANISM: Artificial Sequence
<220> FEATURE:
<223> OTHER INFORMATION: Synthetic Probe

<400> SEQUENCE: 63
cgccaatatt tacgtgctgc ta                                              22

<210> SEQ ID NO 64
<211> LENGTH: 20
<212> TYPE: DNA
<213> ORGANISM: Artificial Sequence
<220> FEATURE:
<223> OTHER INFORMATION: Synthetic Probe

<400> SEQUENCE: 64
acaagtgcct tcactgcagt                                                 20

<210> SEQ ID NO 65
<211> LENGTH: 24
<212> TYPE: DNA
<213> ORGANISM: Artificial Sequence
<220> FEATURE:
<223> OTHER INFORMATION: Synthetic Probe

<400> SEQUENCE: 65
actacctgca ctgtaagcac tttg                                            24

<210> SEQ ID NO 66
<211> LENGTH: 23
<212> TYPE: DNA
<213> ORGANISM: Artificial Sequence
<220> FEATURE:
<223> OTHER INFORMATION: Synthetic Probe

<400> SEQUENCE: 66
actcaccgac agcgttgaat gtt                                             23

<210> SEQ ID NO 67
<211> LENGTH: 22
<212> TYPE: DNA
<213> ORGANISM: Artificial Sequence
<220> FEATURE:
<223> OTHER INFORMATION: Synthetic Probe

<400> SEQUENCE: 67
cccaccgaca gcaatgaatg tt                                              22

<210> SEQ ID NO 68
<211> LENGTH: 22
<212> TYPE: DNA
<213> ORGANISM: Artificial Sequence
<220> FEATURE:
<223> OTHER INFORMATION: Synthetic Probe

<400> SEQUENCE: 68
actcaccgac aggttgaatg tt                                              22

<210> SEQ ID NO 69
<211> LENGTH: 24
<212> TYPE: DNA
<213> ORGANISM: Artificial Sequence
<220> FEATURE:

<223> OTHER INFORMATION: Synthetic Probe

<400> SEQUENCE: 69
aacccaccga caacaatgaa tgtt                                          24

<210> SEQ ID NO 70
<211> LENGTH: 22
<212> TYPE: DNA
<213> ORGANISM: Artificial Sequence
<220> FEATURE:
<223> OTHER INFORMATION: Synthetic Probe

<400> SEQUENCE: 70
tgtgagttct accattgcca aa                                            22

<210> SEQ ID NO 71
<211> LENGTH: 21
<212> TYPE: DNA
<213> ORGANISM: Artificial Sequence
<220> FEATURE:
<223> OTHER INFORMATION: Synthetic Probe

<400> SEQUENCE: 71
tagttggcaa gtctagaacc a                                             21

<210> SEQ ID NO 72
<211> LENGTH: 23
<212> TYPE: DNA
<213> ORGANISM: Artificial Sequence
<220> FEATURE:
<223> OTHER INFORMATION: Synthetic Probe

<400> SEQUENCE: 72
cagtgaattc taccagtgcc ata                                           23

<210> SEQ ID NO 73
<211> LENGTH: 22
<212> TYPE: DNA
<213> ORGANISM: Artificial Sequence
<220> FEATURE:
<223> OTHER INFORMATION: Synthetic Probe

<400> SEQUENCE: 73
acccttatca gttctccgtc ca                                            22

<210> SEQ ID NO 74
<211> LENGTH: 18
<212> TYPE: DNA
<213> ORGANISM: Artificial Sequence
<220> FEATURE:
<223> OTHER INFORMATION: Synthetic Probe

<400> SEQUENCE: 74
gaactgcctt tctctcca                                                 18

<210> SEQ ID NO 75
<211> LENGTH: 23
<212> TYPE: DNA
<213> ORGANISM: Artificial Sequence
<220> FEATURE:
<223> OTHER INFORMATION: Synthetic Probe

<400> SEQUENCE: 75
aagcccaaaa ggagaattct ttg                                           23

```
<210> SEQ ID NO 76
<211> LENGTH: 21
<212> TYPE: DNA
<213> ORGANISM: Artificial Sequence
<220> FEATURE:
<223> OTHER INFORMATION: Synthetic Probe

<400> SEQUENCE: 76
cggctgcaac acaagacacg a                                              21

<210> SEQ ID NO 77
<211> LENGTH: 22
<212> TYPE: DNA
<213> ORGANISM: Artificial Sequence
<220> FEATURE:
<223> OTHER INFORMATION: Synthetic Probe

<400> SEQUENCE: 77
accctccacc atgcaaggga tg                                             22

<210> SEQ ID NO 78
<211> LENGTH: 23
<212> TYPE: DNA
<213> ORGANISM: Artificial Sequence
<220> FEATURE:
<223> OTHER INFORMATION: Synthetic Probe

<400> SEQUENCE: 78
actgatatca gctcagtagg cac                                            23

<210> SEQ ID NO 79
<211> LENGTH: 22
<212> TYPE: DNA
<213> ORGANISM: Artificial Sequence
<220> FEATURE:
<223> OTHER INFORMATION: Synthetic Probe

<400> SEQUENCE: 79
tatctgcact agatgcacct ta                                             22

<210> SEQ ID NO 80
<211> LENGTH: 21
<212> TYPE: DNA
<213> ORGANISM: Artificial Sequence
<220> FEATURE:
<223> OTHER INFORMATION: Synthetic Probe

<400> SEQUENCE: 80
agaaggagca cttagggcag t                                              21

<210> SEQ ID NO 81
<211> LENGTH: 22
<212> TYPE: DNA
<213> ORGANISM: Artificial Sequence
<220> FEATURE:
<223> OTHER INFORMATION: Synthetic Probe

<400> SEQUENCE: 81
taactgcact agatgcacct ta                                             22

<210> SEQ ID NO 82
<211> LENGTH: 22
<212> TYPE: DNA
<213> ORGANISM: Artificial Sequence
<220> FEATURE:
<223> OTHER INFORMATION: Synthetic Probe
```

<400> SEQUENCE: 82
acctaatata tcaaacatat ca                                                  22

<210> SEQ ID NO 83
<211> LENGTH: 22
<212> TYPE: DNA
<213> ORGANISM: Artificial Sequence
<220> FEATURE:
<223> OTHER INFORMATION: Synthetic Probe

<400> SEQUENCE: 83
agctgctttt gggattccgt tg                                                  22

<210> SEQ ID NO 84
<211> LENGTH: 22
<212> TYPE: DNA
<213> ORGANISM: Artificial Sequence
<220> FEATURE:
<223> OTHER INFORMATION: Synthetic Probe

<400> SEQUENCE: 84
ggggacgaaa tccaagcgca gc                                                  22

<210> SEQ ID NO 85
<211> LENGTH: 21
<212> TYPE: DNA
<213> ORGANISM: Artificial Sequence
<220> FEATURE:
<223> OTHER INFORMATION: Synthetic Probe

<400> SEQUENCE: 85
ggctgtcaat tcataggtca g                                                   21

<210> SEQ ID NO 86
<211> LENGTH: 21
<212> TYPE: DNA
<213> ORGANISM: Artificial Sequence
<220> FEATURE:
<223> OTHER INFORMATION: Synthetic Probe

<400> SEQUENCE: 86
ctgggacttt gtaggccagt t                                                   21

<210> SEQ ID NO 87
<211> LENGTH: 24
<212> TYPE: DNA
<213> ORGANISM: Artificial Sequence
<220> FEATURE:
<223> OTHER INFORMATION: Synthetic Probe

<400> SEQUENCE: 87
aaagcgggac tttgagggcc agtt                                                24

<210> SEQ ID NO 88
<211> LENGTH: 22
<212> TYPE: DNA
<213> ORGANISM: Artificial Sequence
<220> FEATURE:
<223> OTHER INFORMATION: Synthetic Probe

<400> SEQUENCE: 88
tccacatgga gttgctgtta ca                                                  22

<210> SEQ ID NO 89
<211> LENGTH: 21

```
<212> TYPE: DNA
<213> ORGANISM: Artificial Sequence
<220> FEATURE:
<223> OTHER INFORMATION: Synthetic Probe

<400> SEQUENCE: 89
gccaatattt ctgtgctgct a                                              21

<210> SEQ ID NO 90
<211> LENGTH: 21
<212> TYPE: DNA
<213> ORGANISM: Artificial Sequence
<220> FEATURE:
<223> OTHER INFORMATION: Synthetic Probe

<400> SEQUENCE: 90
ccaacaacat gaaactacct a                                              21

<210> SEQ ID NO 91
<211> LENGTH: 21
<212> TYPE: DNA
<213> ORGANISM: Artificial Sequence
<220> FEATURE:
<223> OTHER INFORMATION: Synthetic Probe

<400> SEQUENCE: 91
ccaacaacag gaaactacct a                                              21

<210> SEQ ID NO 92
<211> LENGTH: 22
<212> TYPE: DNA
<213> ORGANISM: Artificial Sequence
<220> FEATURE:
<223> OTHER INFORMATION: Synthetic Probe

<400> SEQUENCE: 92
gctgggtgga gaaggtggtg aa                                             22

<210> SEQ ID NO 93
<211> LENGTH: 19
<212> TYPE: DNA
<213> ORGANISM: Artificial Sequence
<220> FEATURE:
<223> OTHER INFORMATION: Synthetic Probe

<400> SEQUENCE: 93
cctatctccc ctctggacc                                                 19

<210> SEQ ID NO 94
<211> LENGTH: 23
<212> TYPE: DNA
<213> ORGANISM: Artificial Sequence
<220> FEATURE:
<223> OTHER INFORMATION: Synthetic Probe

<400> SEQUENCE: 94
gaacaggtag tctgaacact ggg                                            23

<210> SEQ ID NO 95
<211> LENGTH: 22
<212> TYPE: DNA
<213> ORGANISM: Artificial Sequence
<220> FEATURE:
<223> OTHER INFORMATION: Synthetic Probe

<400> SEQUENCE: 95
```

-continued

```
aaccaatgtg cagactactg ta                                          22

<210> SEQ ID NO 96
<211> LENGTH: 23
<212> TYPE: DNA
<213> ORGANISM: Artificial Sequence
<220> FEATURE:
<223> OTHER INFORMATION: Synthetic Probe

<400> SEQUENCE: 96
gaacagatag tctaaacact ggg                                         23

<210> SEQ ID NO 97
<211> LENGTH: 23
<212> TYPE: DNA
<213> ORGANISM: Artificial Sequence
<220> FEATURE:
<223> OTHER INFORMATION: Synthetic Probe

<400> SEQUENCE: 97
tcagttttgc atagatttgc aca                                         23

<210> SEQ ID NO 98
<211> LENGTH: 23
<212> TYPE: DNA
<213> ORGANISM: Artificial Sequence
<220> FEATURE:
<223> OTHER INFORMATION: Synthetic Probe

<400> SEQUENCE: 98
tcagttttgc atggatttgc aca                                         23

<210> SEQ ID NO 99
<211> LENGTH: 22
<212> TYPE: DNA
<213> ORGANISM: Artificial Sequence
<220> FEATURE:
<223> OTHER INFORMATION: Synthetic Probe

<400> SEQUENCE: 99
acatcgttac cagacagtgt ta                                          22

<210> SEQ ID NO 100
<211> LENGTH: 22
<212> TYPE: DNA
<213> ORGANISM: Artificial Sequence
<220> FEATURE:
<223> OTHER INFORMATION: Synthetic Probe

<400> SEQUENCE: 100
tccagcactg tccggtaaga tg                                          22

<210> SEQ ID NO 101
<211> LENGTH: 23
<212> TYPE: DNA
<213> ORGANISM: Artificial Sequence
<220> FEATURE:
<223> OTHER INFORMATION: Synthetic Probe

<400> SEQUENCE: 101
gtcatcatta ccaggcagta tta                                         23

<210> SEQ ID NO 102
<211> LENGTH: 22
<212> TYPE: DNA
<213> ORGANISM: Artificial Sequence
```

```
<220> FEATURE:
<223> OTHER INFORMATION: Synthetic Probe

<400> SEQUENCE: 102
ccatcattac ccggcagtat ta                                              22

<210> SEQ ID NO 103
<211> LENGTH: 22
<212> TYPE: DNA
<213> ORGANISM: Artificial Sequence
<220> FEATURE:
<223> OTHER INFORMATION: Synthetic Probe

<400> SEQUENCE: 103
ttttcccatg ccctatacct ct                                              22

<210> SEQ ID NO 104
<211> LENGTH: 22
<212> TYPE: DNA
<213> ORGANISM: Artificial Sequence
<220> FEATURE:
<223> OTHER INFORMATION: Synthetic Probe

<400> SEQUENCE: 104
aaagaagtat atgcatagga aa                                              22

<210> SEQ ID NO 105
<211> LENGTH: 22
<212> TYPE: DNA
<213> ORGANISM: Artificial Sequence
<220> FEATURE:
<223> OTHER INFORMATION: Synthetic Probe

<400> SEQUENCE: 105
ctagtggtcc taaacatttc ac                                              22

<210> SEQ ID NO 106
<211> LENGTH: 22
<212> TYPE: DNA
<213> ORGANISM: Artificial Sequence
<220> FEATURE:
<223> OTHER INFORMATION: Synthetic Probe

<400> SEQUENCE: 106
aggcatagga tgacaaaggg aa                                              22

<210> SEQ ID NO 107
<211> LENGTH: 22
<212> TYPE: DNA
<213> ORGANISM: Artificial Sequence
<220> FEATURE:
<223> OTHER INFORMATION: Synthetic Probe

<400> SEQUENCE: 107
cagactccgg tggaatgaag ga                                              22

<210> SEQ ID NO 108
<211> LENGTH: 22
<212> TYPE: DNA
<213> ORGANISM: Artificial Sequence
<220> FEATURE:
<223> OTHER INFORMATION: Synthetic Probe

<400> SEQUENCE: 108
ccacacactt ccttacattc ca                                              22
```

<210> SEQ ID NO 109
<211> LENGTH: 22
<212> TYPE: DNA
<213> ORGANISM: Artificial Sequence
<220> FEATURE:
<223> OTHER INFORMATION: Synthetic Probe

<400> SEQUENCE: 109
acaagctttt tgctcgtctt at                                              22

<210> SEQ ID NO 110
<211> LENGTH: 23
<212> TYPE: DNA
<213> ORGANISM: Artificial Sequence
<220> FEATURE:
<223> OTHER INFORMATION: Synthetic Probe

<400> SEQUENCE: 110
ctacctgcac tataagcact tta                                             23

<210> SEQ ID NO 111
<211> LENGTH: 23
<212> TYPE: DNA
<213> ORGANISM: Artificial Sequence
<220> FEATURE:
<223> OTHER INFORMATION: Synthetic Probe

<400> SEQUENCE: 111
ctacctgcac tatgagcact ttg                                             23

<210> SEQ ID NO 112
<211> LENGTH: 22
<212> TYPE: DNA
<213> ORGANISM: Artificial Sequence
<220> FEATURE:
<223> OTHER INFORMATION: Synthetic Probe

<400> SEQUENCE: 112
tcaacatcag tctgataagc ta                                              22

<210> SEQ ID NO 113
<211> LENGTH: 22
<212> TYPE: DNA
<213> ORGANISM: Artificial Sequence
<220> FEATURE:
<223> OTHER INFORMATION: Synthetic Probe

<400> SEQUENCE: 113
tcagccgctg tcacacgcac ag                                              22

<210> SEQ ID NO 114
<211> LENGTH: 22
<212> TYPE: DNA
<213> ORGANISM: Artificial Sequence
<220> FEATURE:
<223> OTHER INFORMATION: Synthetic Probe

<400> SEQUENCE: 114
aggcgaagga tgacaaaggg aa                                              22

<210> SEQ ID NO 115
<211> LENGTH: 21
<212> TYPE: DNA
<213> ORGANISM: Artificial Sequence
<220> FEATURE:
<223> OTHER INFORMATION: Synthetic Probe

```
<400> SEQUENCE: 115
ggccgtgact ggagactgtt a                                              21

<210> SEQ ID NO 116
<211> LENGTH: 22
<212> TYPE: DNA
<213> ORGANISM: Artificial Sequence
<220> FEATURE:
<223> OTHER INFORMATION: Synthetic Probe

<400> SEQUENCE: 116
ggtacaatca acggtcgatg gt                                             22

<210> SEQ ID NO 117
<211> LENGTH: 21
<212> TYPE: DNA
<213> ORGANISM: Artificial Sequence
<220> FEATURE:
<223> OTHER INFORMATION: Synthetic Probe

<400> SEQUENCE: 117
ctgcctgtct gtgcctgctg t                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic Probe

<400> SEQUENCE: 118
gtctgtcaat tcataggtca t                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic Probe

<400> SEQUENCE: 119
cacagttgcc agctgagatt a                                              21

<210> SEQ ID NO 120
<211> LENGTH: 24
<212> TYPE: DNA
<213> ORGANISM: Artificial Sequence
<220> FEATURE:
<223> OTHER INFORMATION: Synthetic Probe

<400> SEQUENCE: 120
atccaatcag ttcctgatgc agta                                           24

<210> SEQ ID NO 121
<211> LENGTH: 21
<212> TYPE: DNA
<213> ORGANISM: Artificial Sequence
<220> FEATURE:
<223> OTHER INFORMATION: Synthetic Probe

<400> SEQUENCE: 121
acatggttag atcaagcaca a                                              21

<210> SEQ ID NO 122
```

```
<211> LENGTH: 21
<212> TYPE: DNA
<213> ORGANISM: Artificial Sequence
<220> FEATURE:
<223> OTHER INFORMATION: Synthetic Probe

<400> SEQUENCE: 122
agaattgcgt ttggacaatc a                                              21

<210> SEQ ID NO 123
<211> LENGTH: 22
<212> TYPE: DNA
<213> ORGANISM: Artificial Sequence
<220> FEATURE:
<223> OTHER INFORMATION: Synthetic Probe

<400> SEQUENCE: 123
acagttcttc aactggcagc tt                                             22

<210> SEQ ID NO 124
<211> LENGTH: 21
<212> TYPE: DNA
<213> ORGANISM: Artificial Sequence
<220> FEATURE:
<223> OTHER INFORMATION: Synthetic Probe

<400> SEQUENCE: 124
aaagtgtcag atacggtgtg g                                              21

<210> SEQ ID NO 125
<211> LENGTH: 23
<212> TYPE: DNA
<213> ORGANISM: Artificial Sequence
<220> FEATURE:
<223> OTHER INFORMATION: Synthetic Probe

<400> SEQUENCE: 125
gaaacccagc agacaatgta gct                                            23

<210> SEQ ID NO 126
<211> LENGTH: 24
<212> TYPE: DNA
<213> ORGANISM: Artificial Sequence
<220> FEATURE:
<223> OTHER INFORMATION: Synthetic Probe

<400> SEQUENCE: 126
gagacccagt agccagatgt agct                                           24

<210> SEQ ID NO 127
<211> LENGTH: 21
<212> TYPE: DNA
<213> ORGANISM: Artificial Sequence
<220> FEATURE:
<223> OTHER INFORMATION: Synthetic Probe

<400> SEQUENCE: 127
ggggtatttg acaaactgac a                                              21

<210> SEQ ID NO 128
<211> LENGTH: 23
<212> TYPE: DNA
<213> ORGANISM: Artificial Sequence
<220> FEATURE:
<223> OTHER INFORMATION: Synthetic Probe

<400> SEQUENCE: 128
```
taaacggaac cactagtgac ttg                                                    23

<210> SEQ ID NO 129
<211> LENGTH: 21
<212> TYPE: DNA
<213> ORGANISM: Artificial Sequence
<220> FEATURE:
<223> OTHER INFORMATION: Synthetic Probe

<400> SEQUENCE: 129
ggaaatccct ggcaatgtga t                                                      21

<210> SEQ ID NO 130
<211> LENGTH: 21
<212> TYPE: DNA
<213> ORGANISM: Artificial Sequence
<220> FEATURE:
<223> OTHER INFORMATION: Synthetic Probe

<400> SEQUENCE: 130
ggtaatccct ggcaatgtga t                                                      21

<210> SEQ ID NO 131
<211> LENGTH: 22
<212> TYPE: DNA
<213> ORGANISM: Artificial Sequence
<220> FEATURE:
<223> OTHER INFORMATION: Synthetic Probe

<400> SEQUENCE: 131
ctgttcctgc tgaactgagc ca                                                     22

<210> SEQ ID NO 132
<211> LENGTH: 22
<212> TYPE: DNA
<213> ORGANISM: Artificial Sequence
<220> FEATURE:
<223> OTHER INFORMATION: Synthetic Probe

<400> SEQUENCE: 132
tcagaccgag acaagtgcaa tg                                                     22

<210> SEQ ID NO 133
<211> LENGTH: 21
<212> TYPE: DNA
<213> ORGANISM: Artificial Sequence
<220> FEATURE:
<223> OTHER INFORMATION: Synthetic Probe

<400> SEQUENCE: 133
gcctatcctg gattacttga a                                                      21

<210> SEQ ID NO 134
<211> LENGTH: 22
<212> TYPE: DNA
<213> ORGANISM: Artificial Sequence
<220> FEATURE:
<223> OTHER INFORMATION: Synthetic Probe

<400> SEQUENCE: 134
aacctatcct gaattacttg aa                                                     22

<210> SEQ ID NO 135
<211> LENGTH: 21
<212> TYPE: DNA

```
<213> ORGANISM: Artificial Sequence
<220> FEATURE:
<223> OTHER INFORMATION: Synthetic Probe

<400> SEQUENCE: 135
gcggaactta gccactgtga a                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic Probe

<400> SEQUENCE: 136
gcagaactta gccactgtga a                                              21

<210> SEQ ID NO 137
<211> LENGTH: 22
<212> TYPE: DNA
<213> ORGANISM: Artificial Sequence
<220> FEATURE:
<223> OTHER INFORMATION: Synthetic Probe

<400> SEQUENCE: 137
ctcaatagac tgtgagctcc tt                                             22

<210> SEQ ID NO 138
<211> LENGTH: 21
<212> TYPE: DNA
<213> ORGANISM: Artificial Sequence
<220> FEATURE:
<223> OTHER INFORMATION: Synthetic Probe

<400> SEQUENCE: 138
acaggattga ggggggggccc t                                             21

<210> SEQ ID NO 139
<211> LENGTH: 22
<212> TYPE: DNA
<213> ORGANISM: Artificial Sequence
<220> FEATURE:
<223> OTHER INFORMATION: Synthetic Probe

<400> SEQUENCE: 139
aagcggttta ccatcccaca ta                                             22

<210> SEQ ID NO 140
<211> LENGTH: 22
<212> TYPE: DNA
<213> ORGANISM: Artificial Sequence
<220> FEATURE:
<223> OTHER INFORMATION: Synthetic Probe

<400> SEQUENCE: 140
atgtatgtgg gacggtaaac ca                                             22

<210> SEQ ID NO 141
<211> LENGTH: 21
<212> TYPE: DNA
<213> ORGANISM: Artificial Sequence
<220> FEATURE:
<223> OTHER INFORMATION: Synthetic Probe

<400> SEQUENCE: 141 aaccgattte agatggtgct a                                              21
```

<210> SEQ ID NO 142
<211> LENGTH: 23
<212> TYPE: DNA
<213> ORGANISM: Artificial Sequence
<220> FEATURE:
<223> OTHER INFORMATION: Synthetic Probe

<400> SEQUENCE: 142
aacactgatt tcaaatggtg cta                                          23

<210> SEQ ID NO 143
<211> LENGTH: 20
<212> TYPE: DNA
<213> ORGANISM: Artificial Sequence
<220> FEATURE:
<223> OTHER INFORMATION: Synthetic Probe

<400> SEQUENCE: 143
accgatttca aatggtgcta                                              20

<210> SEQ ID NO 144
<211> LENGTH: 23
<212> TYPE: DNA
<213> ORGANISM: Artificial Sequence
<220> FEATURE:
<223> OTHER INFORMATION: Synthetic Probe

<400> SEQUENCE: 144
gctttgacaa tactattgca ctg                                          23

<210> SEQ ID NO 145
<211> LENGTH: 23
<212> TYPE: DNA
<213> ORGANISM: Artificial Sequence
<220> FEATURE:
<223> OTHER INFORMATION: Synthetic Probe

<400> SEQUENCE: 145
tcaccaaaac atggaagcac tta                                          23

<210> SEQ ID NO 146
<211> LENGTH: 22
<212> TYPE: DNA
<213> ORGANISM: Artificial Sequence
<220> FEATURE:
<223> OTHER INFORMATION: Synthetic Probe

<400> SEQUENCE: 146
aaagcaagta catccacgtt ta                                           22

<210> SEQ ID NO 147
<211> LENGTH: 23
<212> TYPE: DNA
<213> ORGANISM: Artificial Sequence
<220> FEATURE:
<223> OTHER INFORMATION: Synthetic Probe

<400> SEQUENCE: 147
ctactaaaac atggaagcac tta                                          23

<210> SEQ ID NO 148
<211> LENGTH: 23
<212> TYPE: DNA
<213> ORGANISM: Artificial Sequence
<220> FEATURE:

<223> OTHER INFORMATION: Synthetic Probe

<400> SEQUENCE: 148
agaaagcact tccatgttaa agt                                            23

<210> SEQ ID NO 149
<211> LENGTH: 23
<212> TYPE: DNA
<213> ORGANISM: Artificial Sequence
<220> FEATURE:
<223> OTHER INFORMATION: Synthetic Probe

<400> SEQUENCE: 149
ccactgaaac atggaagcac tta                                            23

<210> SEQ ID NO 150
<211> LENGTH: 22
<212> TYPE: DNA
<213> ORGANISM: Artificial Sequence
<220> FEATURE:
<223> OTHER INFORMATION: Synthetic Probe

<400> SEQUENCE: 150
cagcaggtac ccccatgtta aa                                             22

<210> SEQ ID NO 151
<211> LENGTH: 23
<212> TYPE: DNA
<213> ORGANISM: Artificial Sequence
<220> FEATURE:
<223> OTHER INFORMATION: Synthetic Probe

<400> SEQUENCE: 151
acactcaaac atggaagcac tta                                            23

<210> SEQ ID NO 152
<211> LENGTH: 22
<212> TYPE: DNA
<213> ORGANISM: Artificial Sequence
<220> FEATURE:
<223> OTHER INFORMATION: Synthetic Probe

<400> SEQUENCE: 152
gctgcaaaca tccgactgaa ag                                             22

<210> SEQ ID NO 153
<211> LENGTH: 22
<212> TYPE: DNA
<213> ORGANISM: Artificial Sequence
<220> FEATURE:
<223> OTHER INFORMATION: Synthetic Probe

<400> SEQUENCE: 153
cttccagtcg aggatgttta ca                                             22

<210> SEQ ID NO 154
<211> LENGTH: 22
<212> TYPE: DNA
<213> ORGANISM: Artificial Sequence
<220> FEATURE:
<223> OTHER INFORMATION: Synthetic Probe

<400> SEQUENCE: 154
agctgagtgt aggatgttta ca                                             22

```
<210> SEQ ID NO 155
<211> LENGTH: 23
<212> TYPE: DNA
<213> ORGANISM: Artificial Sequence
<220> FEATURE:
<223> OTHER INFORMATION: Synthetic Probe

<400> SEQUENCE: 155
gctgagagtg taggatgttt aca                                          23

<210> SEQ ID NO 156
<211> LENGTH: 22
<212> TYPE: DNA
<213> ORGANISM: Artificial Sequence
<220> FEATURE:
<223> OTHER INFORMATION: Synthetic Probe

<400> SEQUENCE: 156
cttccagtcg gggatgttta ca                                           22

<210> SEQ ID NO 157
<211> LENGTH: 22
<212> TYPE: DNA
<213> ORGANISM: Artificial Sequence
<220> FEATURE:
<223> OTHER INFORMATION: Synthetic Probe

<400> SEQUENCE: 157
gctgtaaaca tccgactgaa ag                                           22

<210> SEQ ID NO 158
<211> LENGTH: 20
<212> TYPE: DNA
<213> ORGANISM: Artificial Sequence
<220> FEATURE:
<223> OTHER INFORMATION: Synthetic Probe

<400> SEQUENCE: 158
tccagtcaag gatgtttaca                                              20

<210> SEQ ID NO 159
<211> LENGTH: 21
<212> TYPE: DNA
<213> ORGANISM: Artificial Sequence
<220> FEATURE:
<223> OTHER INFORMATION: Synthetic Probe

<400> SEQUENCE: 159
cagctatgcc agcatcttgc c                                            21

<210> SEQ ID NO 160
<211> LENGTH: 21
<212> TYPE: DNA
<213> ORGANISM: Artificial Sequence
<220> FEATURE:
<223> OTHER INFORMATION: Synthetic Probe

<400> SEQUENCE: 160
gcaacttagt aatgtgcaat a                                            21

<210> SEQ ID NO 161
<211> LENGTH: 23
<212> TYPE: DNA
<213> ORGANISM: Artificial Sequence
<220> FEATURE:
<223> OTHER INFORMATION: Synthetic Probe
```

```
<400> SEQUENCE: 161
ttcgccctct caacccagct ttt                                          23

<210> SEQ ID NO 162
<211> LENGTH: 22
<212> TYPE: DNA
<213> ORGANISM: Artificial Sequence
<220> FEATURE:
<223> OTHER INFORMATION: Synthetic Probe

<400> SEQUENCE: 162
agaggtcgac cgtgtaatgt gc                                           22

<210> SEQ ID NO 163
<211> LENGTH: 22
<212> TYPE: DNA
<213> ORGANISM: Artificial Sequence
<220> FEATURE:
<223> OTHER INFORMATION: Synthetic Probe

<400> SEQUENCE: 163
ccagcagcac ctggggcagt gg                                           22

<210> SEQ ID NO 164
<211> LENGTH: 23
<212> TYPE: DNA
<213> ORGANISM: Artificial Sequence
<220> FEATURE:
<223> OTHER INFORMATION: Synthetic Probe

<400> SEQUENCE: 164
acaccaatgc cctaggggat gcg                                          23

<210> SEQ ID NO 165
<211> LENGTH: 23
<212> TYPE: DNA
<213> ORGANISM: Artificial Sequence
<220> FEATURE:
<223> OTHER INFORMATION: Synthetic Probe

<400> SEQUENCE: 165
acacttactg gacacctact agg                                          23

<210> SEQ ID NO 166
<211> LENGTH: 20
<212> TYPE: DNA
<213> ORGANISM: Artificial Sequence
<220> FEATURE:
<223> OTHER INFORMATION: Synthetic Probe

<400> SEQUENCE: 166
ctggaggaag ggcccagagg                                              20

<210> SEQ ID NO 167
<211> LENGTH: 22
<212> TYPE: DNA
<213> ORGANISM: Artificial Sequence
<220> FEATURE:
<223> OTHER INFORMATION: Synthetic Probe

<400> SEQUENCE: 167
acggaagggc agagagggcc ag                                           22

<210> SEQ ID NO 168
<211> LENGTH: 22
```

<212> TYPE: DNA
<213> ORGANISM: Artificial Sequence
<220> FEATURE:
<223> OTHER INFORMATION: Synthetic Probe

<400> SEQUENCE: 168
aaagaggtta accaggtgtg tt                                      22

<210> SEQ ID NO 169
<211> LENGTH: 19
<212> TYPE: DNA
<213> ORGANISM: Artificial Sequence
<220> FEATURE:
<223> OTHER INFORMATION: Synthetic Probe

<400> SEQUENCE: 169
caatgcaact acaatgcac                                          19

<210> SEQ ID NO 170
<211> LENGTH: 23
<212> TYPE: DNA
<213> ORGANISM: Artificial Sequence
<220> FEATURE:
<223> OTHER INFORMATION: Synthetic Probe

<400> SEQUENCE: 170
tctctgcagg ccgtgtgctt tgc                                     23

<210> SEQ ID NO 171
<211> LENGTH: 21
<212> TYPE: DNA
<213> ORGANISM: Artificial Sequence
<220> FEATURE:
<223> OTHER INFORMATION: Synthetic Probe

<400> SEQUENCE: 171
ttctaggata ggcccagggg c                                       21

<210> SEQ ID NO 172
<211> LENGTH: 23
<212> TYPE: DNA
<213> ORGANISM: Artificial Sequence
<220> FEATURE:
<223> OTHER INFORMATION: Synthetic Probe

<400> SEQUENCE: 172 acattttcg ttattgctct tga                                      23

<210> SEQ ID NO 173
<211> LENGTH: 23
<212> TYPE: DNA
<213> ORGANISM: Artificial Sequence
<220> FEATURE:
<223> OTHER INFORMATION: Synthetic Probe

<400> SEQUENCE: 173
aaaggcatca tataggagct gga                                     23

<210> SEQ ID NO 174
<211> LENGTH: 23
<212> TYPE: DNA
<213> ORGANISM: Artificial Sequence
<220> FEATURE:
<223> OTHER INFORMATION: Synthetic Probe

<400> SEQUENCE: 174
tcaacaaaat cactgatgct gga                                              23

<210> SEQ ID NO 175
<211> LENGTH: 21
<212> TYPE: DNA
<213> ORGANISM: Artificial Sequence
<220> FEATURE:
<223> OTHER INFORMATION: Synthetic Probe

<400> SEQUENCE: 175
tgagctcctg gaggacaggg a                                                21

<210> SEQ ID NO 176
<211> LENGTH: 21
<212> TYPE: DNA
<213> ORGANISM: Artificial Sequence
<220> FEATURE:
<223> OTHER INFORMATION: Synthetic Probe

<400> SEQUENCE: 176
tgcaatgcaa cagcaatgca c                                                21

<210> SEQ ID NO 177
<211> LENGTH: 23
<212> TYPE: DNA
<213> ORGANISM: Artificial Sequence
<220> FEATURE:
<223> OTHER INFORMATION: Synthetic Probe

<400> SEQUENCE: 177
ggctataaag taactgagac gga                                              23

<210> SEQ ID NO 178
<211> LENGTH: 24
<212> TYPE: DNA
<213> ORGANISM: Artificial Sequence
<220> FEATURE:
<223> OTHER INFORMATION: Synthetic Probe

<400> SEQUENCE: 178
gacgggtgcg atttctgtgt gaga                                             24

<210> SEQ ID NO 179
<211> LENGTH: 21
<212> TYPE: DNA
<213> ORGANISM: Artificial Sequence
<220> FEATURE:
<223> OTHER INFORMATION: Synthetic Probe

<400> SEQUENCE: 179
gccctggact aggagtcagc a                                                21

<210> SEQ ID NO 180
<211> LENGTH: 23
<212> TYPE: DNA
<213> ORGANISM: Artificial Sequence
<220> FEATURE:
<223> OTHER INFORMATION: Synthetic Probe

<400> SEQUENCE: 180
agaggcaggc atgcgggcag aca                                              23

<210> SEQ ID NO 181
<211> LENGTH: 23
<212> TYPE: DNA
<213> ORGANISM: Artificial Sequence
<220> FEATURE:
<223> OTHER INFORMATION: Synthetic Probe

<400> SEQUENCE: 181
aacaaccagc taagacactg cca                                              23

<210> SEQ ID NO 182
<211> LENGTH: 23
<212> TYPE: DNA
<213> ORGANISM: Artificial Sequence
<220> FEATURE:
<223> OTHER INFORMATION: Synthetic Probe

<400> SEQUENCE: 182
caatcagcta atgacactgc cta                                              23

<210> SEQ ID NO 183
<211> LENGTH: 23
<212> TYPE: DNA
<213> ORGANISM: Artificial Sequence
<220> FEATURE:
<223> OTHER INFORMATION: Synthetic Probe

<400> SEQUENCE: 183
gcaatcagct aactacactg cct                                              23

<210> SEQ ID NO 184
<211> LENGTH: 22
<212> TYPE: DNA
<213> ORGANISM: Artificial Sequence
<220> FEATURE:
<223> OTHER INFORMATION: Synthetic Probe

<400> SEQUENCE: 184
gtacccctgg agattctgat aa                                               22

<210> SEQ ID NO 185
<211> LENGTH: 23
<212> TYPE: DNA
<213> ORGANISM: Artificial Sequence
<220> FEATURE:
<223> OTHER INFORMATION: Synthetic Probe

<400> SEQUENCE: 185
ctcacaccta ggttccaagg att                                              23

<210> SEQ ID NO 186
<211> LENGTH: 22
<212> TYPE: DNA
<213> ORGANISM: Artificial Sequence
<220> FEATURE:
<223> OTHER INFORMATION: Synthetic Probe

<400> SEQUENCE: 186
ttacagatgg ataccgtgca at                                               22

<210> SEQ ID NO 187
<211> LENGTH: 22
<212> TYPE: DNA
<213> ORGANISM: Artificial Sequence
<220> FEATURE:
<223> OTHER INFORMATION: Synthetic Probe

<400> SEQUENCE: 187
aaattgcatc gtgatccacc cg                                               22

<210> SEQ ID NO 188
<211> LENGTH: 22
<212> TYPE: DNA
<213> ORGANISM: Artificial Sequence
<220> FEATURE:
<223> OTHER INFORMATION: Synthetic Probe

<400> SEQUENCE: 188
ataaggattt ttaggggcat ta                                              22

<210> SEQ ID NO 189
<211> LENGTH: 22
<212> TYPE: DNA
<213> ORGANISM: Artificial Sequence
<220> FEATURE:
<223> OTHER INFORMATION: Synthetic Probe

<400> SEQUENCE: 189
tcaccattgc taaagtgcaa tt                                              22

<210> SEQ ID NO 190
<211> LENGTH: 22
<212> TYPE: DNA
<213> ORGANISM: Artificial Sequence
<220> FEATURE:
<223> OTHER INFORMATION: Synthetic Probe

<400> SEQUENCE: 190
aaacgtggaa tttcctctat gt                                              22

<210> SEQ ID NO 191
<211> LENGTH: 21
<212> TYPE: DNA
<213> ORGANISM: Artificial Sequence
<220> FEATURE:
<223> OTHER INFORMATION: Synthetic Probe

<400> SEQUENCE: 191
aaagatcaac catgtattat t                                               21

<210> SEQ ID NO 192
<211> LENGTH: 22
<212> TYPE: DNA
<213> ORGANISM: Artificial Sequence
<220> FEATURE:
<223> OTHER INFORMATION: Synthetic Probe

<400> SEQUENCE: 192
gcgaatataa cacggtcgat ct                                              22

<210> SEQ ID NO 193
<211> LENGTH: 21
<212> TYPE: DNA
<213> ORGANISM: Artificial Sequence
<220> FEATURE:
<223> OTHER INFORMATION: Synthetic Probe

<400> SEQUENCE: 193
ccaggttcca ccccagcagg c                                               21

<210> SEQ ID NO 194
<211> LENGTH: 21
<212> TYPE: DNA
<213> ORGANISM: Artificial Sequence
<220> FEATURE:
<223> OTHER INFORMATION: Synthetic Probe

<400> SEQUENCE: 194
acactcaaaa gatggcggca c                                                   21

<210> SEQ ID NO 195
<211> LENGTH: 23
<212> TYPE: DNA
<213> ORGANISM: Artificial Sequence
<220> FEATURE:
<223> OTHER INFORMATION: Synthetic Probe

<400> SEQUENCE: 195
acgctcaaat gtcgcagcac ttt                                                 23

<210> SEQ ID NO 196
<211> LENGTH: 23
<212> TYPE: DNA
<213> ORGANISM: Artificial Sequence
<220> FEATURE:
<223> OTHER INFORMATION: Synthetic Probe

<400> SEQUENCE: 196
acaccccaaa atcgaagcac ttc                                                 23

<210> SEQ ID NO 197
<211> LENGTH: 22
<212> TYPE: DNA
<213> ORGANISM: Artificial Sequence
<220> FEATURE:
<223> OTHER INFORMATION: Synthetic Probe

<400> SEQUENCE: 197
ggaaagcgcc cccattttga gt                                                  22

<210> SEQ ID NO 198
<211> LENGTH: 22
<212> TYPE: DNA
<213> ORGANISM: Artificial Sequence
<220> FEATURE:
<223> OTHER INFORMATION: Synthetic Probe

<400> SEQUENCE: 198
cacttatcag gttgtattat aa                                                  22

<210> SEQ ID NO 199
<211> LENGTH: 22
<212> TYPE: DNA
<213> ORGANISM: Artificial Sequence
<220> FEATURE:
<223> OTHER INFORMATION: Synthetic Probe

<400> SEQUENCE: 199
tcacgcgagc cgaacgaaca aa                                                  22

<210> SEQ ID NO 200
<211> LENGTH: 21
<212> TYPE: DNA
<213> ORGANISM: Artificial Sequence
<220> FEATURE:
<223> OTHER INFORMATION: Synthetic Probe

<400> SEQUENCE: 200
acgtggattt tcctctatga t                                                   21

<210> SEQ ID NO 201

```
<211> LENGTH: 21
<212> TYPE: DNA
<213> ORGANISM: Artificial Sequence
<220> FEATURE:
<223> OTHER INFORMATION: Synthetic Probe

<400> SEQUENCE: 201
ctcatagaag gagaatctac c                                                  21

<210> SEQ ID NO 202
<211> LENGTH: 22
<212> TYPE: DNA
<213> ORGANISM: Artificial Sequence
<220> FEATURE:
<223> OTHER INFORMATION: Synthetic Probe

<400> SEQUENCE: 202
aacatggatt ttcctctatg at                                                 22

<210> SEQ ID NO 203
<211> LENGTH: 22
<212> TYPE: DNA
<213> ORGANISM: Artificial Sequence
<220> FEATURE:
<223> OTHER INFORMATION: Synthetic Probe

<400> SEQUENCE: 203
acaaaagttg cctttgtgtg at                                                 22

<210> SEQ ID NO 204
<211> LENGTH: 22
<212> TYPE: DNA
<213> ORGANISM: Artificial Sequence
<220> FEATURE:
<223> OTHER INFORMATION: Synthetic Probe

<400> SEQUENCE: 204
acacaggacc tggagtcagg ag                                                 22

<210> SEQ ID NO 205
<211> LENGTH: 19
<212> TYPE: DNA
<213> ORGANISM: Artificial Sequence
<220> FEATURE:
<223> OTHER INFORMATION: Synthetic Probe

<400> SEQUENCE: 205
tacgttccat agtctacca                                                     19

<210> SEQ ID NO 206
<211> LENGTH: 22
<212> TYPE: DNA
<213> ORGANISM: Artificial Sequence
<220> FEATURE:
<223> OTHER INFORMATION: Synthetic Probe

<400> SEQUENCE: 206
aagatgtgga ccatattaca ta                                                 22

<210> SEQ ID NO 207
<211> LENGTH: 22
<212> TYPE: DNA
<213> ORGANISM: Artificial Sequence
<220> FEATURE:
<223> OTHER INFORMATION: Synthetic Probe

<400> SEQUENCE: 207
```
gcgcatgttc tatggtcaac ca                                              22

<210> SEQ ID NO 208
<211> LENGTH: 22
<212> TYPE: DNA
<213> ORGANISM: Artificial Sequence
<220> FEATURE:
<223> OTHER INFORMATION: Synthetic Probe

<400> SEQUENCE: 208
acagagagct tgcccttgta ta                                              22

<210> SEQ ID NO 209
<211> LENGTH: 22
<212> TYPE: DNA
<213> ORGANISM: Artificial Sequence
<220> FEATURE:
<223> OTHER INFORMATION: Synthetic Probe

<400> SEQUENCE: 209
cgaatccacc acgaacaact tc                                              22

<210> SEQ ID NO 210
<211> LENGTH: 22
<212> TYPE: DNA
<213> ORGANISM: Artificial Sequence
<220> FEATURE:
<223> OTHER INFORMATION: Synthetic Probe

<400> SEQUENCE: 210
agccacaatc accttctgat ct                                              22

<210> SEQ ID NO 211
<211> LENGTH: 20
<212> TYPE: DNA
<213> ORGANISM: Artificial Sequence
<220> FEATURE:
<223> OTHER INFORMATION: Synthetic Probe

<400> SEQUENCE: 211
tatgaacaat ttctaggaat                                                 20

<210> SEQ ID NO 212
<211> LENGTH: 23
<212> TYPE: DNA
<213> ORGANISM: Artificial Sequence
<220> FEATURE:
<223> OTHER INFORMATION: Synthetic Probe

<400> SEQUENCE: 212
aggggttcac cgagcaacat tcg                                             23

<210> SEQ ID NO 213
<211> LENGTH: 22
<212> TYPE: DNA
<213> ORGANISM: Artificial Sequence
<220> FEATURE:
<223> OTHER INFORMATION: Synthetic Probe

<400> SEQUENCE: 213
tgcaaagttg ctcgggtaac ct                                              22

<210> SEQ ID NO 214
<211> LENGTH: 22
<212> TYPE: DNA

```
<213> ORGANISM: Artificial Sequence
<220> FEATURE:
<223> OTHER INFORMATION: Synthetic Probe

<400> SEQUENCE: 214
aacaggccat ctgtgttata tt                                              22

<210> SEQ ID NO 215
<211> LENGTH: 21
<212> TYPE: DNA
<213> ORGANISM: Artificial Sequence
<220> FEATURE:
<223> OTHER INFORMATION: Synthetic Probe

<400> SEQUENCE: 215
cgtacgctat acggtctact a                                               21

<210> SEQ ID NO 216
<211> LENGTH: 23
<212> TYPE: DNA
<213> ORGANISM: Artificial Sequence
<220> FEATURE:
<223> OTHER INFORMATION: Synthetic Probe

<400> SEQUENCE: 216
acggctagtg gaccaggtga agt                                             23

<210> SEQ ID NO 217
<211> LENGTH: 23
<212> TYPE: DNA
<213> ORGANISM: Artificial Sequence
<220> FEATURE:
<223> OTHER INFORMATION: Synthetic Probe

<400> SEQUENCE: 217
gcgcccaatt aatgtctgtt gat                                             23

<210> SEQ ID NO 218
<211> LENGTH: 22
<212> TYPE: DNA
<213> ORGANISM: Artificial Sequence
<220> FEATURE:
<223> OTHER INFORMATION: Synthetic Probe

<400> SEQUENCE: 218
ggccttctga ccctaagtcc ag                                              22

<210> SEQ ID NO 219
<211> LENGTH: 22
<212> TYPE: DNA
<213> ORGANISM: Artificial Sequence
<220> FEATURE:
<223> OTHER INFORMATION: Synthetic Probe

<400> SEQUENCE: 219
ggccttctga ctccaagtcc ag                                              22

<210> SEQ ID NO 220
<211> LENGTH: 22
<212> TYPE: DNA
<213> ORGANISM: Artificial Sequence
<220> FEATURE:
<223> OTHER INFORMATION: Synthetic Probe

<400> SEQUENCE: 220
ctgaggggcc tcagaccgag ct                                              22
```

<210> SEQ ID NO 221
<211> LENGTH: 22
<212> TYPE: DNA
<213> ORGANISM: Artificial Sequence
<220> FEATURE:
<223> OTHER INFORMATION: Synthetic Probe

<400> SEQUENCE: 221
ttcaaaacat gaattgctgc tg                                              22

<210> SEQ ID NO 222
<211> LENGTH: 21
<212> TYPE: DNA
<213> ORGANISM: Artificial Sequence
<220> FEATURE:
<223> OTHER INFORMATION: Synthetic Probe

<400> SEQUENCE: 222
ggcggacacg acattcccga t                                               21

<210> SEQ ID NO 223
<211> LENGTH: 23
<212> TYPE: DNA
<213> ORGANISM: Artificial Sequence
<220> FEATURE:
<223> OTHER INFORMATION: Synthetic Probe

<400> SEQUENCE: 223
tcaacgggag tgatcgtgtc att                                             23

<210> SEQ ID NO 224
<211> LENGTH: 22
<212> TYPE: DNA
<213> ORGANISM: Artificial Sequence
<220> FEATURE:
<223> OTHER INFORMATION: Synthetic Probe

<400> SEQUENCE: 224
acggttttac cagacagtat ta                                              22

<210> SEQ ID NO 225
<211> LENGTH: 21
<212> TYPE: DNA
<213> ORGANISM: Artificial Sequence
<220> FEATURE:
<223> OTHER INFORMATION: Synthetic Probe

<400> SEQUENCE: 225
tgcatgacgg cctgcaagac a                                               21

<210> SEQ ID NO 226
<211> LENGTH: 23
<212> TYPE: DNA
<213> ORGANISM: Artificial Sequence
<220> FEATURE:
<223> OTHER INFORMATION: Synthetic Probe

<400> SEQUENCE: 226
ccacccaatg acctactcca aga                                             23

<210> SEQ ID NO 227
<211> LENGTH: 21
<212> TYPE: DNA
<213> ORGANISM: Artificial Sequence
<220> FEATURE:

<223> OTHER INFORMATION: Synthetic Probe

<400> SEQUENCE: 227
agacatggag gagccatcca g                                            21

<210> SEQ ID NO 228
<211> LENGTH: 22
<212> TYPE: DNA
<213> ORGANISM: Artificial Sequence
<220> FEATURE:
<223> OTHER INFORMATION: Synthetic Probe

<400> SEQUENCE: 228
acaccgagga gcccatcatg at                                           22

<210> SEQ ID NO 229
<211> LENGTH: 22
<212> TYPE: DNA
<213> ORGANISM: Artificial Sequence
<220> FEATURE:
<223> OTHER INFORMATION: Synthetic Probe

<400> SEQUENCE: 229
atgggacatc ctacatatgc aa                                           22

<210> SEQ ID NO 230
<211> LENGTH: 22
<212> TYPE: DNA
<213> ORGANISM: Artificial Sequence
<220> FEATURE:
<223> OTHER INFORMATION: Synthetic Probe

<400> SEQUENCE: 230
accagctaac aatacactgc ca                                           22

<210> SEQ ID NO 231
<211> LENGTH: 22
<212> TYPE: DNA
<213> ORGANISM: Artificial Sequence
<220> FEATURE:
<223> OTHER INFORMATION: Synthetic Probe

<400> SEQUENCE: 231
tattaggaac acatcgcaaa aa                                           22

<210> SEQ ID NO 232
<211> LENGTH: 23
<212> TYPE: DNA
<213> ORGANISM: Artificial Sequence
<220> FEATURE:
<223> OTHER INFORMATION: Synthetic Probe

<400> SEQUENCE: 232
aaactcagta atggtaacgg ttt                                          23

<210> SEQ ID NO 233
<211> LENGTH: 22
<212> TYPE: DNA
<213> ORGANISM: Artificial Sequence
<220> FEATURE:
<223> OTHER INFORMATION: Synthetic Probe

<400> SEQUENCE: 233
gtctcagttt cctctgcaaa ca                                           22

```
<210> SEQ ID NO 234
<211> LENGTH: 21
<212> TYPE: DNA
<213> ORGANISM: Artificial Sequence
<220> FEATURE:
<223> OTHER INFORMATION: Synthetic Probe

<400> SEQUENCE: 234
cttctttgca gatgagactg a                                              21

<210> SEQ ID NO 235
<211> LENGTH: 22
<212> TYPE: DNA
<213> ORGANISM: Artificial Sequence
<220> FEATURE:
<223> OTHER INFORMATION: Synthetic Probe

<400> SEQUENCE: 235
cgaactcacc acggacaacc tc                                             22

<210> SEQ ID NO 236
<211> LENGTH: 22
<212> TYPE: DNA
<213> ORGANISM: Artificial Sequence
<220> FEATURE:
<223> OTHER INFORMATION: Synthetic Probe

<400> SEQUENCE: 236
cgatgtagtc caaaggcaca ta                                             22

<210> SEQ ID NO 237
<211> LENGTH: 23
<212> TYPE: DNA
<213> ORGANISM: Artificial Sequence
<220> FEATURE:
<223> OTHER INFORMATION: Synthetic Probe

<400> SEQUENCE: 237
agaagacggg aggagaggag tga                                            23

<210> SEQ ID NO 238
<211> LENGTH: 22
<212> TYPE: DNA
<213> ORGANISM: Artificial Sequence
<220> FEATURE:
<223> OTHER INFORMATION: Synthetic Probe

<400> SEQUENCE: 238
atcgggaggg gactgagcct ga                                             22

<210> SEQ ID NO 239
<211> LENGTH: 20
<212> TYPE: DNA
<213> ORGANISM: Artificial Sequence
<220> FEATURE:
<223> OTHER INFORMATION: Synthetic Probe

<400> SEQUENCE: 239
agaggagagc cgtgtatgac                                                20

<210> SEQ ID NO 240
<211> LENGTH: 22
<212> TYPE: DNA
<213> ORGANISM: Artificial Sequence
<220> FEATURE:
<223> OTHER INFORMATION: Synthetic Probe
```

<400> SEQUENCE: 240
gaattcatca cggccagcct ct                                              22

<210> SEQ ID NO 241
<211> LENGTH: 22
<212> TYPE: DNA
<213> ORGANISM: Artificial Sequence
<220> FEATURE:
<223> OTHER INFORMATION: Synthetic Probe

<400> SEQUENCE: 241
ctcggggcag ctcagtacag ga                                              22

<210> SEQ ID NO 242
<211> LENGTH: 22
<212> TYPE: DNA
<213> ORGANISM: Artificial Sequence
<220> FEATURE:
<223> OTHER INFORMATION: Synthetic Probe

<400> SEQUENCE: 242
aactggatgt ccctgtatga tt                                              22

<210> SEQ ID NO 243
<211> LENGTH: 22
<212> TYPE: DNA
<213> ORGANISM: Artificial Sequence
<220> FEATURE:
<223> OTHER INFORMATION: Synthetic Probe

<400> SEQUENCE: 243
aagtggatga ccctgtacga tt                                              22

<210> SEQ ID NO 244
<211> LENGTH: 21
<212> TYPE: DNA
<213> ORGANISM: Artificial Sequence
<220> FEATURE:
<223> OTHER INFORMATION: Synthetic Probe

<400> SEQUENCE: 244
ttgagagtgc cattatctgg g                                               21

<210> SEQ ID NO 245
<211> LENGTH: 23
<212> TYPE: DNA
<213> ORGANISM: Artificial Sequence
<220> FEATURE:
<223> OTHER INFORMATION: Synthetic Probe

<400> SEQUENCE: 245
gctgccgtat atgtgatgtc act                                             23

<210> SEQ ID NO 246
<211> LENGTH: 22
<212> TYPE: DNA
<213> ORGANISM: Artificial Sequence
<220> FEATURE:
<223> OTHER INFORMATION: Synthetic Probe

<400> SEQUENCE: 246
cagcatggag tcctccaggt tg                                              22

<210> SEQ ID NO 247
<211> LENGTH: 23

```
<212> TYPE: DNA
<213> ORGANISM: Artificial Sequence
<220> FEATURE:
<223> OTHER INFORMATION: Synthetic Probe

<400> SEQUENCE: 247
tcctcatgga agggttcccc act                                             23

<210> SEQ ID NO 248
<211> LENGTH: 23
<212> TYPE: DNA
<213> ORGANISM: Artificial Sequence
<220> FEATURE:
<223> OTHER INFORMATION: Synthetic Probe

<400> SEQUENCE: 248
aagaatcttg tcccgcaggt cct                                             23

<210> SEQ ID NO 249
<211> LENGTH: 22
<212> TYPE: DNA
<213> ORGANISM: Artificial Sequence
<220> FEATURE:
<223> OTHER INFORMATION: Synthetic Probe

<400> SEQUENCE: 249
aatgaaagcc taccatgtac aa                                              22

<210> SEQ ID NO 250
<211> LENGTH: 21
<212> TYPE: DNA
<213> ORGANISM: Artificial Sequence
<220> FEATURE:
<223> OTHER INFORMATION: Synthetic Probe

<400> SEQUENCE: 250
ctggcacaca gtagaccttc a                                               21

<210> SEQ ID NO 251
<211> LENGTH: 24
<212> TYPE: DNA
<213> ORGANISM: Artificial Sequence
<220> FEATURE:
<223> OTHER INFORMATION: Synthetic Probe

<400> SEQUENCE: 251
aagaggtttc ccgtgtatgt ttca                                            24

<210> SEQ ID NO 252
<211> LENGTH: 23
<212> TYPE: DNA
<213> ORGANISM: Artificial Sequence
<220> FEATURE:
<223> OTHER INFORMATION: Synthetic Probe

<400> SEQUENCE: 252
aaagaagtgc accatgtttg ttt                                             23

<210> SEQ ID NO 253
<211> LENGTH: 17
<212> TYPE: DNA
<213> ORGANISM: Artificial Sequence
<220> FEATURE:
<223> OTHER INFORMATION: Synthetic Probe

<400> SEQUENCE: 253
```
gagattggcc atgtaat                                                  17

<210> SEQ ID NO 254
<211> LENGTH: 21
<212> TYPE: DNA
<213> ORGANISM: Artificial Sequence
<220> FEATURE:
<223> OTHER INFORMATION: Synthetic Probe

<400> SEQUENCE: 254
acaaaccaca gtgtgctgct g                                             21

<210> SEQ ID NO 255
<211> LENGTH: 23
<212> TYPE: DNA
<213> ORGANISM: Artificial Sequence
<220> FEATURE:
<223> OTHER INFORMATION: Synthetic Probe

<400> SEQUENCE: 255
gaaaaacgcc ccctggcttg aaa                                           23

<210> SEQ ID NO 256
<211> LENGTH: 23
<212> TYPE: DNA
<213> ORGANISM: Artificial Sequence
<220> FEATURE:
<223> OTHER INFORMATION: Synthetic Probe

<400> SEQUENCE: 256
ttaaacatca ctgcaagtct taa                                           23

<210> SEQ ID NO 257
<211> LENGTH: 22
<212> TYPE: DNA
<213> ORGANISM: Artificial Sequence
<220> FEATURE:
<223> OTHER INFORMATION: Synthetic Probe

<400> SEQUENCE: 257
cagaatcctt gcccaggtgc at                                            22

<210> SEQ ID NO 258
<211> LENGTH: 22
<212> TYPE: DNA
<213> ORGANISM: Artificial Sequence
<220> FEATURE:
<223> OTHER INFORMATION: Synthetic Probe

<400> SEQUENCE: 258
tctcacccag ggacaaagga tt                                            22

<210> SEQ ID NO 259
<211> LENGTH: 21
<212> TYPE: DNA
<213> ORGANISM: Artificial Sequence
<220> FEATURE:
<223> OTHER INFORMATION: Synthetic Probe

<400> SEQUENCE: 259
tagcacccag atagcaagga t                                             21

<210> SEQ ID NO 260
<211> LENGTH: 23
<212> TYPE: DNA
<213> ORGANISM: Artificial Sequence -continued

```
<220> FEATURE:
<223> OTHER INFORMATION: Synthetic Probe

<400> SEQUENCE: 260
ctgcagaact gttcccgctg cta                                              23

<210> SEQ ID NO 261
<211> LENGTH: 21
<212> TYPE: DNA
<213> ORGANISM: Artificial Sequence
<220> FEATURE:
<223> OTHER INFORMATION: Synthetic Probe

<400> SEQUENCE: 261
atagagtgca gaccagggtc t                                                21

<210> SEQ ID NO 262
<211> LENGTH: 22
<212> TYPE: DNA
<213> ORGANISM: Artificial Sequence
<220> FEATURE:
<223> OTHER INFORMATION: Synthetic Probe

<400> SEQUENCE: 262
gaggaaacca gcaagtgttg ac                                               22

<210> SEQ ID NO 263
<211> LENGTH: 21
<212> TYPE: DNA
<213> ORGANISM: Artificial Sequence
<220> FEATURE:
<223> OTHER INFORMATION: Synthetic Probe

<400> SEQUENCE: 263
tctactcaga agggtgcctt a                                                21

<210> SEQ ID NO 264
<211> LENGTH: 21
<212> TYPE: DNA
<213> ORGANISM: Artificial Sequence
<220> FEATURE:
<223> OTHER INFORMATION: Synthetic Probe

<400> SEQUENCE: 264
ttcactccaa aaggtgcaaa a                                                21

<210> SEQ ID NO 265
<211> LENGTH: 23
<212> TYPE: DNA
<213> ORGANISM: Artificial Sequence
<220> FEATURE:
<223> OTHER INFORMATION: Synthetic Probe

<400> SEQUENCE: 265
tctactccaa aaggctacaa tca                                              23

<210> SEQ ID NO 266
<211> LENGTH: 23
<212> TYPE: DNA
<213> ORGANISM: Artificial Sequence
<220> FEATURE:
<223> OTHER INFORMATION: Synthetic Probe

<400> SEQUENCE: 266
tctacccaca gacgtaccaa tca                                              23
```

<210> SEQ ID NO 267
<211> LENGTH: 23
<212> TYPE: DNA
<213> ORGANISM: Artificial Sequence
<220> FEATURE:
<223> OTHER INFORMATION: Synthetic Probe

<400> SEQUENCE: 267
tgtgattgcc actctcctga gta                                             23

<210> SEQ ID NO 268
<211> LENGTH: 21
<212> TYPE: DNA
<213> ORGANISM: Artificial Sequence
<220> FEATURE:
<223> OTHER INFORMATION: Synthetic Probe

<400> SEQUENCE: 268
tgactgcaga gcaaaagaca c                                               21

<210> SEQ ID NO 269
<211> LENGTH: 22
<212> TYPE: DNA
<213> ORGANISM: Artificial Sequence
<220> FEATURE:
<223> OTHER INFORMATION: Synthetic Probe

<400> SEQUENCE: 269
gacctcagct atgacagcac tt                                              22

<210> SEQ ID NO 270
<211> LENGTH: 23
<212> TYPE: DNA
<213> ORGANISM: Artificial Sequence
<220> FEATURE:
<223> OTHER INFORMATION: Synthetic Probe

<400> SEQUENCE: 270
gaaagtgccc tcaaggctga gtg                                             23

<210> SEQ ID NO 271
<211> LENGTH: 22
<212> TYPE: DNA
<213> ORGANISM: Artificial Sequence
<220> FEATURE:
<223> OTHER INFORMATION: Synthetic Probe

<400> SEQUENCE: 271
ataaatgaca cctccctgtg aa                                              22

<210> SEQ ID NO 272
<211> LENGTH: 20
<212> TYPE: DNA
<213> ORGANISM: Artificial Sequence
<220> FEATURE:
<223> OTHER INFORMATION: Synthetic Probe

<400> SEQUENCE: 272
ctactcacag aagtgtcaat                                                 20

<210> SEQ ID NO 273
<211> LENGTH: 21
<212> TYPE: DNA
<213> ORGANISM: Artificial Sequence
<220> FEATURE:
<223> OTHER INFORMATION: Synthetic Probe

```
<400> SEQUENCE: 273
acgctccaaa agaaggcact c                                              21

<210> SEQ ID NO 274
<211> LENGTH: 24
<212> TYPE: DNA
<213> ORGANISM: Artificial Sequence
<220> FEATURE:
<223> OTHER INFORMATION: Synthetic Probe

<400> SEQUENCE: 274
cagaaagtgc tttcttttgg agaa                                           24

<210> SEQ ID NO 275
<211> LENGTH: 18
<212> TYPE: DNA
<213> ORGANISM: Artificial Sequence
<220> FEATURE:
<223> OTHER INFORMATION: Synthetic Probe

<400> SEQUENCE: 275
accctctgaa aggaagca                                                  18

<210> SEQ ID NO 276
<211> LENGTH: 22
<212> TYPE: DNA
<213> ORGANISM: Artificial Sequence
<220> FEATURE:
<223> OTHER INFORMATION: Synthetic Probe

<400> SEQUENCE: 276
aaagtgcttc ttacctccag at                                             22

<210> SEQ ID NO 277
<211> LENGTH: 22
<212> TYPE: DNA
<213> ORGANISM: Artificial Sequence
<220> FEATURE:
<223> OTHER INFORMATION: Synthetic Probe

<400> SEQUENCE: 277
agacagtgct tccatctaga gg                                             22

<210> SEQ ID NO 278
<211> LENGTH: 23
<212> TYPE: DNA
<213> ORGANISM: Artificial Sequence
<220> FEATURE:
<223> OTHER INFORMATION: Synthetic Probe

<400> SEQUENCE: 278
aacactctaa aggatgcac gat                                             23

<210> SEQ ID NO 279
<211> LENGTH: 22
<212> TYPE: DNA
<213> ORGANISM: Artificial Sequence
<220> FEATURE:
<223> OTHER INFORMATION: Synthetic Probe

<400> SEQUENCE: 279
aacactctaa agggatgcac ga                                             22

<210> SEQ ID NO 280
```

<211> LENGTH: 22
<212> TYPE: DNA
<213> ORGANISM: Artificial Sequence
<220> FEATURE:
<223> OTHER INFORMATION: Synthetic Probe

<400> SEQUENCE: 280
acactctaaa aggatgcacg at                                              22

<210> SEQ ID NO 281
<211> LENGTH: 21
<212> TYPE: DNA
<213> ORGANISM: Artificial Sequence
<220> FEATURE:
<223> OTHER INFORMATION: Synthetic Probe

<400> SEQUENCE: 281
tccagcaaag ggaagcgctt t                                               21

<210> SEQ ID NO 282
<211> LENGTH: 20
<212> TYPE: DNA
<213> ORGANISM: Artificial Sequence
<220> FEATURE:
<223> OTHER INFORMATION: Synthetic Probe

<400> SEQUENCE: 282
aaagggcttc cctttgcaga                                                 20

<210> SEQ ID NO 283
<211> LENGTH: 22
<212> TYPE: DNA
<213> ORGANISM: Artificial Sequence
<220> FEATURE:
<223> OTHER INFORMATION: Synthetic Probe

<400> SEQUENCE: 283
acctctaaag gggagcgctt tg                                              22

<210> SEQ ID NO 284
<211> LENGTH: 22
<212> TYPE: DNA
<213> ORGANISM: Artificial Sequence
<220> FEATURE:
<223> OTHER INFORMATION: Synthetic Probe

<400> SEQUENCE: 284
cactctaaag agaagcgctt tg                                              22

<210> SEQ ID NO 285
<211> LENGTH: 23
<212> TYPE: DNA
<213> ORGANISM: Artificial Sequence
<220> FEATURE:
<223> OTHER INFORMATION: Synthetic Probe

<400> SEQUENCE: 285
cagaaagtgc ttccctccag aga                                             23

<210> SEQ ID NO 286
<211> LENGTH: 21
<212> TYPE: DNA
<213> ORGANISM: Artificial Sequence
<220> FEATURE:
<223> OTHER INFORMATION: Synthetic Probe

<400> SEQUENCE: 286
gctccaaagg gaagcgcttt g                                                 21

<210> SEQ ID NO 287
<211> LENGTH: 22
<212> TYPE: DNA
<213> ORGANISM: Artificial Sequence
<220> FEATURE:
<223> OTHER INFORMATION: Synthetic Probe

<400> SEQUENCE: 287
acactctgaa gggaagcgct tt                                                22

<210> SEQ ID NO 288
<211> LENGTH: 21
<212> TYPE: DNA
<213> ORGANISM: Artificial Sequence
<220> FEATURE:
<223> OTHER INFORMATION: Synthetic Probe

<400> SEQUENCE: 288
tcctctaaag agaagcgctt t                                                 21

<210> SEQ ID NO 289
<211> LENGTH: 23
<212> TYPE: DNA
<213> ORGANISM: Artificial Sequence
<220> FEATURE:
<223> OTHER INFORMATION: Synthetic Probe

<400> SEQUENCE: 289
agagaaagtg cttccctcta gag                                               23

<210> SEQ ID NO 290
<211> LENGTH: 25
<212> TYPE: DNA
<213> ORGANISM: Artificial Sequence
<220> FEATURE:
<223> OTHER INFORMATION: Synthetic Probe

<400> SEQUENCE: 290
gtaacactct aaaaggatgc acttt                                             25

<210> SEQ ID NO 291
<211> LENGTH: 23
<212> TYPE: DNA
<213> ORGANISM: Artificial Sequence
<220> FEATURE:
<223> OTHER INFORMATION: Synthetic Probe

<400> SEQUENCE: 291
aaacctctaa aaggatgcac ttt                                               23

<210> SEQ ID NO 292
<211> LENGTH: 22
<212> TYPE: DNA
<213> ORGANISM: Artificial Sequence
<220> FEATURE:
<223> OTHER INFORMATION: Synthetic Probe

<400> SEQUENCE: 292
atcctctaaa aagatgcact tt                                                22

<210> SEQ ID NO 293
<211> LENGTH: 23
<212> TYPE: DNA

```
<213> ORGANISM: Artificial Sequence
<220> FEATURE:
<223> OTHER INFORMATION: Synthetic Probe

<400> SEQUENCE: 293
acactctaaa gggaggcact ttg                                              23

<210> SEQ ID NO 294
<211> LENGTH: 22
<212> TYPE: DNA
<213> ORGANISM: Artificial Sequence
<220> FEATURE:
<223> OTHER INFORMATION: Synthetic Probe

<400> SEQUENCE: 294
acactctaaa aggaggcact tt                                               22

<210> SEQ ID NO 295
<211> LENGTH: 22
<212> TYPE: DNA
<213> ORGANISM: Artificial Sequence
<220> FEATURE:
<223> OTHER INFORMATION: Synthetic Probe

<400> SEQUENCE: 295
gaaagtgctc cctttggag aa                                                22

<210> SEQ ID NO 296
<211> LENGTH: 22
<212> TYPE: DNA
<213> ORGANISM: Artificial Sequence
<220> FEATURE:
<223> OTHER INFORMATION: Synthetic Probe

<400> SEQUENCE: 296
acagtccaaa gggaagcact tt                                               22

<210> SEQ ID NO 297
<211> LENGTH: 21
<212> TYPE: DNA
<213> ORGANISM: Artificial Sequence
<220> FEATURE:
<223> OTHER INFORMATION: Synthetic Probe

<400> SEQUENCE: 297
agaaagtact ccctctgga g                                                 21

<210> SEQ ID NO 298
<211> LENGTH: 21
<212> TYPE: DNA
<213> ORGANISM: Artificial Sequence
<220> FEATURE:
<223> OTHER INFORMATION: Synthetic Probe

<400> SEQUENCE: 298
ccctctaaaa ggaagcactt t                                                21

<210> SEQ ID NO 299
<211> LENGTH: 23
<212> TYPE: DNA
<213> ORGANISM: Artificial Sequence
<220> FEATURE:
<223> OTHER INFORMATION: Synthetic Probe

<400> SEQUENCE: 299
aaccctctaa aaggaagcac ttt                                              23
```

<210> SEQ ID NO 300
<211> LENGTH: 23
<212> TYPE: DNA
<213> ORGANISM: Artificial Sequence
<220> FEATURE:
<223> OTHER INFORMATION: Synthetic Probe

<400> SEQUENCE: 300
aacccaccaa agagaagcac ttt                                    23

<210> SEQ ID NO 301
<211> LENGTH: 23
<212> TYPE: DNA
<213> ORGANISM: Artificial Sequence
<220> FEATURE:
<223> OTHER INFORMATION: Synthetic Probe

<400> SEQUENCE: 301
cagaaagggc ttccctttgt aga                                    23

<210> SEQ ID NO 302
<211> LENGTH: 21
<212> TYPE: DNA
<213> ORGANISM: Artificial Sequence
<220> FEATURE:
<223> OTHER INFORMATION: Synthetic Probe

<400> SEQUENCE: 302
ccctcaaaaa ggaagcactt t                                      21

<210> SEQ ID NO 303
<211> LENGTH: 22
<212> TYPE: DNA
<213> ORGANISM: Artificial Sequence
<220> FEATURE:
<223> OTHER INFORMATION: Synthetic Probe

<400> SEQUENCE: 303
aaccctctaa aaggaagcac tt                                     22

<210> SEQ ID NO 304
<211> LENGTH: 24
<212> TYPE: DNA
<213> ORGANISM: Artificial Sequence
<220> FEATURE:
<223> OTHER INFORMATION: Synthetic Probe

<400> SEQUENCE: 304
acactctaaa gggaagcact ttgt                                   24

<210> SEQ ID NO 305
<211> LENGTH: 22
<212> TYPE: DNA
<213> ORGANISM: Artificial Sequence
<220> FEATURE:
<223> OTHER INFORMATION: Synthetic Probe

<400> SEQUENCE: 305
actctaaagg gaagcactt gt                                      22

<210> SEQ ID NO 306
<211> LENGTH: 22
<212> TYPE: DNA
<213> ORGANISM: Artificial Sequence
<220> FEATURE:

<223> OTHER INFORMATION: Synthetic Probe

<400> SEQUENCE: 306
acactctaaa gggaagtgcg tt                                    22

<210> SEQ ID NO 307
<211> LENGTH: 23
<212> TYPE: DNA
<213> ORGANISM: Artificial Sequence
<220> FEATURE:
<223> OTHER INFORMATION: Synthetic Probe

<400> SEQUENCE: 307
aacactctaa agggaaccat ttt                                   23

<210> SEQ ID NO 308
<211> LENGTH: 21
<212> TYPE: DNA
<213> ORGANISM: Artificial Sequence
<220> FEATURE:
<223> OTHER INFORMATION: Synthetic Probe

<400> SEQUENCE: 308
ccctctatag ggaagcgcgt t                                     21

<210> SEQ ID NO 309
<211> LENGTH: 21
<212> TYPE: DNA
<213> ORGANISM: Artificial Sequence
<220> FEATURE:
<223> OTHER INFORMATION: Synthetic Probe

<400> SEQUENCE: 309
actccaaagg gaagcgcctt c                                     21

<210> SEQ ID NO 310
<211> LENGTH: 22
<212> TYPE: DNA
<213> ORGANISM: Artificial Sequence
<220> FEATURE:
<223> OTHER INFORMATION: Synthetic Probe

<400> SEQUENCE: 310
gagaaagtgc ttccctttgt ag                                    22

<210> SEQ ID NO 311
<211> LENGTH: 21
<212> TYPE: DNA
<213> ORGANISM: Artificial Sequence
<220> FEATURE:
<223> OTHER INFORMATION: Synthetic Probe

<400> SEQUENCE: 311
agaaagtgca tccctctgga g                                     21

<210> SEQ ID NO 312
<211> LENGTH: 21
<212> TYPE: DNA
<213> ORGANISM: Artificial Sequence
<220> FEATURE:
<223> OTHER INFORMATION: Synthetic Probe

<400> SEQUENCE: 312
gctctaaagg gaagcgcctt c                                     21

<210> SEQ ID NO 313
<211> LENGTH: 21
<212> TYPE: DNA
<213> ORGANISM: Artificial Sequence
<220> FEATURE:
<223> OTHER INFORMATION: Synthetic Probe

<400> SEQUENCE: 313
agaaagtgct tccctctaga g                                              21

<210> SEQ ID NO 314
<211> LENGTH: 24
<212> TYPE: DNA
<213> ORGANISM: Artificial Sequence
<220> FEATURE:
<223> OTHER INFORMATION: Synthetic Probe

<400> SEQUENCE: 314
aacagaaagt gcttccctca agag                                           24

<210> SEQ ID NO 315
<211> LENGTH: 21
<212> TYPE: DNA
<213> ORGANISM: Artificial Sequence
<220> FEATURE:
<223> OTHER INFORMATION: Synthetic Probe

<400> SEQUENCE: 315
gcctctaaaa ggaagcactt t                                              21

<210> SEQ ID NO 316
<211> LENGTH: 24
<212> TYPE: DNA
<213> ORGANISM: Artificial Sequence
<220> FEATURE:
<223> OTHER INFORMATION: Synthetic Probe

<400> SEQUENCE: 316
aacagaaagc gcttccctct agag                                           24

<210> SEQ ID NO 317
<211> LENGTH: 21
<212> TYPE: DNA
<213> ORGANISM: Artificial Sequence
<220> FEATURE:
<223> OTHER INFORMATION: Synthetic Probe

<400> SEQUENCE: 317
agaaagggct tccctttgca g                                              21

<210> SEQ ID NO 318
<211> LENGTH: 22
<212> TYPE: DNA
<213> ORGANISM: Artificial Sequence
<220> FEATURE:
<223> OTHER INFORMATION: Synthetic Probe

<400> SEQUENCE: 318
acggtcctac actcaaggca tg                                             22

<210> SEQ ID NO 319
<211> LENGTH: 22
<212> TYPE: DNA
<213> ORGANISM: Artificial Sequence
<220> FEATURE:
<223> OTHER INFORMATION: Synthetic Probe

<400> SEQUENCE: 319
tttcagttat caatctgtca ca                                          22

<210> SEQ ID NO 320
<211> LENGTH: 22
<212> TYPE: DNA
<213> ORGANISM: Artificial Sequence
<220> FEATURE:
<223> OTHER INFORMATION: Synthetic Probe

<400> SEQUENCE: 320
ctcgtgacat gatgatcccc ga                                          22

<210> SEQ ID NO 321
<211> LENGTH: 20
<212> TYPE: DNA
<213> ORGANISM: Artificial Sequence
<220> FEATURE:
<223> OTHER INFORMATION: Synthetic Probe

<400> SEQUENCE: 321
acttgctaaa aatgcagaat                                             20

<210> SEQ ID NO 322
<211> LENGTH: 22
<212> TYPE: DNA
<213> ORGANISM: Artificial Sequence
<220> FEATURE:
<223> OTHER INFORMATION: Synthetic Probe

<400> SEQUENCE: 322
cacacaataa atgtttgctg at                                          22

<210> SEQ ID NO 323
<211> LENGTH: 22
<212> TYPE: DNA
<213> ORGANISM: Artificial Sequence
<220> FEATURE:
<223> OTHER INFORMATION: Synthetic Probe

<400> SEQUENCE: 323
gcaaaagtaa ttgccagttt tg                                          22

<210> SEQ ID NO 324
<211> LENGTH: 22
<212> TYPE: DNA
<213> ORGANISM: Artificial Sequence
<220> FEATURE:
<223> OTHER INFORMATION: Synthetic Probe

<400> SEQUENCE: 324
acaaaagcaa ctgaggttct tg                                          22

<210> SEQ ID NO 325
<211> LENGTH: 22
<212> TYPE: DNA
<213> ORGANISM: Artificial Sequence
<220> FEATURE:
<223> OTHER INFORMATION: Synthetic Probe

<400> SEQUENCE: 325
gcaaaagtaa ttgagatttt tg                                          22

<210> SEQ ID NO 326
<211> LENGTH: 22

```
<212> TYPE: DNA
<213> ORGANISM: Artificial Sequence
<220> FEATURE:
<223> OTHER INFORMATION: Synthetic Probe

<400> SEQUENCE: 326
gcaaaagaaa ctgtggtttt tg                                              22

<210> SEQ ID NO 327
<211> LENGTH: 21
<212> TYPE: DNA
<213> ORGANISM: Artificial Sequence
<220> FEATURE:
<223> OTHER INFORMATION: Synthetic Probe

<400> SEQUENCE: 327
agagctcatc catagttgtc a                                               21

<210> SEQ ID NO 328
<211> LENGTH: 22
<212> TYPE: DNA
<213> ORGANISM: Artificial Sequence
<220> FEATURE:
<223> OTHER INFORMATION: Synthetic Probe

<400> SEQUENCE: 328
atgtgcctga gggagtaaga ca                                              22

<210> SEQ ID NO 329
<211> LENGTH: 21
<212> TYPE: DNA
<213> ORGANISM: Artificial Sequence
<220> FEATURE:
<223> OTHER INFORMATION: Synthetic Probe

<400> SEQUENCE: 329
tggaaaccaa gagtgggtcg c                                               21

<210> SEQ ID NO 330
<211> LENGTH: 21
<212> TYPE: DNA
<213> ORGANISM: Artificial Sequence
<220> FEATURE:
<223> OTHER INFORMATION: Synthetic Probe

<400> SEQUENCE: 330
ttgtctaacc agtcacctgt t                                               21

<210> SEQ ID NO 331
<211> LENGTH: 21
<212> TYPE: DNA
<213> ORGANISM: Artificial Sequence
<220> FEATURE:
<223> OTHER INFORMATION: Synthetic Probe

<400> SEQUENCE: 331
aaaacaaaat ctcaccgttt t                                               21

<210> SEQ ID NO 332
<211> LENGTH: 21
<212> TYPE: DNA
<213> ORGANISM: Artificial Sequence
<220> FEATURE:
<223> OTHER INFORMATION: Synthetic Probe

<400> SEQUENCE: 332
```

```
actggctgag tcaggactag c                                         21

<210> SEQ ID NO 333
<211> LENGTH: 21
<212> TYPE: DNA
<213> ORGANISM: Artificial Sequence
<220> FEATURE:
<223> OTHER INFORMATION: Synthetic Probe

<400> SEQUENCE: 333
atcagaggtt cagcttaccc t                                         21

<210> SEQ ID NO 334
<211> LENGTH: 20
<212> TYPE: DNA
<213> ORGANISM: Artificial Sequence
<220> FEATURE:
<223> OTHER INFORMATION: Synthetic Probe

<400> SEQUENCE: 334
catattacaa tgagctcatc                                           20

<210> SEQ ID NO 335
<211> LENGTH: 23
<212> TYPE: DNA
<213> ORGANISM: Artificial Sequence
<220> FEATURE:
<223> OTHER INFORMATION: Synthetic Probe

<400> SEQUENCE: 335
agacaaggcc cacccgtgca aac                                       23

<210> SEQ ID NO 336
<211> LENGTH: 19
<212> TYPE: DNA
<213> ORGANISM: Artificial Sequence
<220> FEATURE:
<223> OTHER INFORMATION: Synthetic Probe

<400> SEQUENCE: 336
attttggtac agcagctca                                            19

<210> SEQ ID NO 337
<211> LENGTH: 21
<212> TYPE: DNA
<213> ORGANISM: Artificial Sequence
<220> FEATURE:
<223> OTHER INFORMATION: Synthetic Probe

<400> SEQUENCE: 337
ttttggtgca tatttacttt a                                         21

<210> SEQ ID NO 338
<211> LENGTH: 20
<212> TYPE: DNA
<213> ORGANISM: Artificial Sequence
<220> FEATURE:
<223> OTHER INFORMATION: Synthetic Probe

<400> SEQUENCE: 338
ggcggccggc cggcgcacgc                                           20

<210> SEQ ID NO 339
<211> LENGTH: 22
<212> TYPE: DNA
<213> ORGANISM: Artificial Sequence
```

<220> FEATURE:
<223> OTHER INFORMATION: Synthetic Probe

<400> SEQUENCE: 339
acttcaagga tcttaaactt tg                                              22

<210> SEQ ID NO 340
<211> LENGTH: 20
<212> TYPE: DNA
<213> ORGANISM: Artificial Sequence
<220> FEATURE:
<223> OTHER INFORMATION: Synthetic Probe

<400> SEQUENCE: 340
gcaaatggta cagctacttt                                                 20

<210> SEQ ID NO 341
<211> LENGTH: 19
<212> TYPE: DNA
<213> ORGANISM: Artificial Sequence
<220> FEATURE:
<223> OTHER INFORMATION: Synthetic Probe

<400> SEQUENCE: 341
gggaaacgta tgtcaacct                                                  19

<210> SEQ ID NO 342
<211> LENGTH: 19
<212> TYPE: DNA
<213> ORGANISM: Artificial Sequence
<220> FEATURE:
<223> OTHER INFORMATION: Synthetic Probe

<400> SEQUENCE: 342
gcctgctgac accgtgcct                                                  19

<210> SEQ ID NO 343
<211> LENGTH: 22
<212> TYPE: DNA
<213> ORGANISM: Artificial Sequence
<220> FEATURE:
<223> OTHER INFORMATION: Synthetic Probe

<400> SEQUENCE: 343
aaacagacat cgcgagccag cc                                              22

<210> SEQ ID NO 344
<211> LENGTH: 19
<212> TYPE: DNA
<213> ORGANISM: Artificial Sequence
<220> FEATURE:
<223> OTHER INFORMATION: Synthetic Probe

<400> SEQUENCE: 344
gttgggatca caggcgccc                                                  19

<210> SEQ ID NO 345
<211> LENGTH: 23
<212> TYPE: DNA
<213> ORGANISM: Artificial Sequence
<220> FEATURE:
<223> OTHER INFORMATION: Synthetic Probe

<400> SEQUENCE: 345
gttctgtcct ggaagaacat act                                             23

```
<210> SEQ ID NO 346
<211> LENGTH: 20
<212> TYPE: DNA
<213> ORGANISM: Artificial Sequence
<220> FEATURE:
<223> OTHER INFORMATION: Synthetic Probe

<400> SEQUENCE: 346
gtgtgtatac atttatacat                                                 20

<210> SEQ ID NO 347
<211> LENGTH: 21
<212> TYPE: DNA
<213> ORGANISM: Artificial Sequence
<220> FEATURE:
<223> OTHER INFORMATION: Synthetic Probe

<400> SEQUENCE: 347
actttccagg attcattaac t                                               21

<210> SEQ ID NO 348
<211> LENGTH: 22
<212> TYPE: DNA
<213> ORGANISM: Artificial Sequence
<220> FEATURE:
<223> OTHER INFORMATION: Synthetic Probe

<400> SEQUENCE: 348
tgcaaaggta attgctgttt tc                                              22

<210> SEQ ID NO 349
<211> LENGTH: 21
<212> TYPE: DNA
<213> ORGANISM: Artificial Sequence
<220> FEATURE:
<223> OTHER INFORMATION: Synthetic Probe

<400> SEQUENCE: 349
ctcactcaga tggccaactc a                                               21

<210> SEQ ID NO 350
<211> LENGTH: 20
<212> TYPE: DNA
<213> ORGANISM: Artificial Sequence
<220> FEATURE:
<223> OTHER INFORMATION: Synthetic Probe

<400> SEQUENCE: 350
tgggccaccg ccgagcggac                                                 20

<210> SEQ ID NO 351
<211> LENGTH: 24
<212> TYPE: DNA
<213> ORGANISM: Artificial Sequence
<220> FEATURE:
<223> OTHER INFORMATION: Synthetic Probe

<400> SEQUENCE: 351
ctgatcagtt acacatcact tcag                                            24

<210> SEQ ID NO 352
<211> LENGTH: 21
<212> TYPE: DNA
<213> ORGANISM: Artificial Sequence
<220> FEATURE:
<223> OTHER INFORMATION: Synthetic Probe
```

<400> SEQUENCE: 352
gtgggtgtgt gcatgagcgt g							21

<210> SEQ ID NO 353
<211> LENGTH: 19
<212> TYPE: DNA
<213> ORGANISM: Artificial Sequence
<220> FEATURE:
<223> OTHER INFORMATION: Synthetic Probe

<400> SEQUENCE: 353
gctcctgtcc aactggctc							19

<210> SEQ ID NO 354
<211> LENGTH: 23
<212> TYPE: DNA
<213> ORGANISM: Artificial Sequence
<220> FEATURE:
<223> OTHER INFORMATION: Synthetic Probe

<400> SEQUENCE: 354
caaagacgtg gagaaattag aat							23

<210> SEQ ID NO 355
<211> LENGTH: 21
<212> TYPE: DNA
<213> ORGANISM: Artificial Sequence
<220> FEATURE:
<223> OTHER INFORMATION: Synthetic Probe

<400> SEQUENCE: 355
caggtaccaa tattttatct a							21

<210> SEQ ID NO 356
<211> LENGTH: 21
<212> TYPE: DNA
<213> ORGANISM: Artificial Sequence
<220> FEATURE:
<223> OTHER INFORMATION: Synthetic Probe

<400> SEQUENCE: 356
acaatcctag agcacaagaa g							21

<210> SEQ ID NO 357
<211> LENGTH: 23
<212> TYPE: DNA
<213> ORGANISM: Artificial Sequence
<220> FEATURE:
<223> OTHER INFORMATION: Synthetic Probe

<400> SEQUENCE: 357
atcgcggttt ataccaaatg aat							23

<210> SEQ ID NO 358
<211> LENGTH: 22
<212> TYPE: DNA
<213> ORGANISM: Artificial Sequence
<220> FEATURE:
<223> OTHER INFORMATION: Synthetic Probe

<400> SEQUENCE: 358
cctaatgatt catcattctc aa							22

<210> SEQ ID NO 359

```
<211> LENGTH: 21
<212> TYPE: DNA
<213> ORGANISM: Artificial Sequence
<220> FEATURE:
<223> OTHER INFORMATION: Synthetic Probe

<400> SEQUENCE: 359
actgatctag agaacacaag a                                              21

<210> SEQ ID NO 360
<211> LENGTH: 23
<212> TYPE: DNA
<213> ORGANISM: Artificial Sequence
<220> FEATURE:
<223> OTHER INFORMATION: Synthetic Probe

<400> SEQUENCE: 360
agtaactggt tgaacaactg taa                                            23

<210> SEQ ID NO 361
<211> LENGTH: 21
<212> TYPE: DNA
<213> ORGANISM: Artificial Sequence
<220> FEATURE:
<223> OTHER INFORMATION: Synthetic Probe

<400> SEQUENCE: 361
gtaatgggac cttcctcttt g                                              21

<210> SEQ ID NO 362
<211> LENGTH: 22
<212> TYPE: DNA
<213> ORGANISM: Artificial Sequence
<220> FEATURE:
<223> OTHER INFORMATION: Synthetic Probe

<400> SEQUENCE: 362
ctcagtccca ggcaaaccat aa                                             22

<210> SEQ ID NO 363
<211> LENGTH: 19
<212> TYPE: DNA
<213> ORGANISM: Artificial Sequence
<220> FEATURE:
<223> OTHER INFORMATION: Synthetic Probe

<400> SEQUENCE: 363
tagcatacag atacgccca                                                 19

<210> SEQ ID NO 364
<211> LENGTH: 22
<212> TYPE: DNA
<213> ORGANISM: Artificial Sequence
<220> FEATURE:
<223> OTHER INFORMATION: Synthetic Probe

<400> SEQUENCE: 364
ggacctaaaa atacaatgca ta                                             22

<210> SEQ ID NO 365
<211> LENGTH: 21
<212> TYPE: DNA
<213> ORGANISM: Artificial Sequence
<220> FEATURE:
<223> OTHER INFORMATION: Synthetic Probe

<400> SEQUENCE: 365
```

```
gtgactcatc acctatggaa a                                                 21
```

<210> SEQ ID NO 366
<211> LENGTH: 21
<212> TYPE: DNA
<213> ORGANISM: Artificial Sequence
<220> FEATURE:
<223> OTHER INFORMATION: Synthetic Probe

<400> SEQUENCE: 366

```
gttctaaccc attgtggcca a                                                 21
```

<210> SEQ ID NO 367
<211> LENGTH: 24
<212> TYPE: DNA
<213> ORGANISM: Artificial Sequence
<220> FEATURE:
<223> OTHER INFORMATION: Synthetic Probe

<400> SEQUENCE: 367

```
tctgggaacc ggcatttgtt ctga                                              24
```

<210> SEQ ID NO 368
<211> LENGTH: 22
<212> TYPE: DNA
<213> ORGANISM: Artificial Sequence
<220> FEATURE:
<223> OTHER INFORMATION: Synthetic Probe

<400> SEQUENCE: 368

```
ctgcactttt atgaataagc tc                                                22
```

<210> SEQ ID NO 369
<211> LENGTH: 20
<212> TYPE: DNA
<213> ORGANISM: Artificial Sequence
<220> FEATURE:
<223> OTHER INFORMATION: Synthetic Probe

<400> SEQUENCE: 369

```
acaatgagaa cccatggtct                                                   20
```

<210> SEQ ID NO 370
<211> LENGTH: 22
<212> TYPE: DNA
<213> ORGANISM: Artificial Sequence
<220> FEATURE:
<223> OTHER INFORMATION: Synthetic Probe

<400> SEQUENCE: 370

```
acatcatcgc atattgacac aa                                                22
```

<210> SEQ ID NO 371
<211> LENGTH: 25
<212> TYPE: DNA
<213> ORGANISM: Artificial Sequence
<220> FEATURE:
<223> OTHER INFORMATION: Synthetic Probe

<400> SEQUENCE: 371

```
gctgagcaat gcctggctgg tgcct                                             25
```

<210> SEQ ID NO 372
<211> LENGTH: 25
<212> TYPE: DNA

<213> ORGANISM: Artificial Sequence
<220> FEATURE:
<223> OTHER INFORMATION: Synthetic Probe

<400> SEQUENCE: 372
aaagtcacag gccaccccag atggg          25

<210> SEQ ID NO 373
<211> LENGTH: 21
<212> TYPE: DNA
<213> ORGANISM: Artificial Sequence
<220> FEATURE:
<223> OTHER INFORMATION: Synthetic Probe

<400> SEQUENCE: 373
agacacacca cggcacactt c              21

<210> SEQ ID NO 374
<211> LENGTH: 21
<212> TYPE: DNA
<213> ORGANISM: Artificial Sequence
<220> FEATURE:
<223> OTHER INFORMATION: Synthetic Probe

<400> SEQUENCE: 374
cccgaggagc cgggcaggct t              21

<210> SEQ ID NO 375
<211> LENGTH: 22
<212> TYPE: DNA
<213> ORGANISM: Artificial Sequence
<220> FEATURE:
<223> OTHER INFORMATION: Synthetic Probe

<400> SEQUENCE: 375
acagtggtca tcgagtgaca ca             22

<210> SEQ ID NO 376
<211> LENGTH: 22
<212> TYPE: DNA
<213> ORGANISM: Artificial Sequence
<220> FEATURE:
<223> OTHER INFORMATION: Synthetic Probe

<400> SEQUENCE: 376
tgacgatgac aacgatgacg ta             22

<210> SEQ ID NO 377
<211> LENGTH: 20
<212> TYPE: DNA
<213> ORGANISM: Artificial Sequence
<220> FEATURE:
<223> OTHER INFORMATION: Synthetic Probe

<400> SEQUENCE: 377
gtttgataaa ctgacacaac                20

<210> SEQ ID NO 378
<211> LENGTH: 23
<212> TYPE: DNA
<213> ORGANISM: Artificial Sequence
<220> FEATURE:
<223> OTHER INFORMATION: Synthetic Probe

<400> SEQUENCE: 378
gagcaaggct cttgtctgta agt            23

```
<210> SEQ ID NO 379
<211> LENGTH: 22
<212> TYPE: DNA
<213> ORGANISM: Artificial Sequence
<220> FEATURE:
<223> OTHER INFORMATION: Synthetic Probe

<400> SEQUENCE: 379
ctcctccaac aatcctagac ca                                               22

<210> SEQ ID NO 380
<211> LENGTH: 23
<212> TYPE: DNA
<213> ORGANISM: Artificial Sequence
<220> FEATURE:
<223> OTHER INFORMATION: Synthetic Probe

<400> SEQUENCE: 380
gggccgcagc tgtcgcccgt gtc                                              23

<210> SEQ ID NO 381
<211> LENGTH: 22
<212> TYPE: DNA
<213> ORGANISM: Artificial Sequence
<220> FEATURE:
<223> OTHER INFORMATION: Synthetic Probe

<400> SEQUENCE: 381
gcaaaagtaa ttgcagtgtg tg                                               22

<210> SEQ ID NO 382
<211> LENGTH: 19
<212> TYPE: DNA
<213> ORGANISM: Artificial Sequence
<220> FEATURE:
<223> OTHER INFORMATION: Synthetic Probe

<400> SEQUENCE: 382
gtcctgaatt ccgcagcct                                                   19

<210> SEQ ID NO 383
<211> LENGTH: 23
<212> TYPE: DNA
<213> ORGANISM: Artificial Sequence
<220> FEATURE:
<223> OTHER INFORMATION: Synthetic Probe

<400> SEQUENCE: 383
aggagaaggc accatgggat tta                                              23

<210> SEQ ID NO 384
<211> LENGTH: 21
<212> TYPE: DNA
<213> ORGANISM: Artificial Sequence
<220> FEATURE:
<223> OTHER INFORMATION: Synthetic Probe

<400> SEQUENCE: 384
atctttgatt ttcagtagtt t                                                21

<210> SEQ ID NO 385
<211> LENGTH: 21
<212> TYPE: DNA
<213> ORGANISM: Artificial Sequence
<220> FEATURE:
```

<223> OTHER INFORMATION: Synthetic Probe

<400> SEQUENCE: 385
gttatagatc tggatttgaa c                                         21

<210> SEQ ID NO 386
<211> LENGTH: 25
<212> TYPE: DNA
<213> ORGANISM: Artificial Sequence
<220> FEATURE:
<223> OTHER INFORMATION: Synthetic Probe

<400> SEQUENCE: 386
acggagctgt cccaacacca cccct                                     25

<210> SEQ ID NO 387
<211> LENGTH: 20
<212> TYPE: DNA
<213> ORGANISM: Artificial Sequence
<220> FEATURE:
<223> OTHER INFORMATION: Synthetic Probe

<400> SEQUENCE: 387
agagatgaga gaaacaccct                                           20

<210> SEQ ID NO 388
<211> LENGTH: 21
<212> TYPE: DNA
<213> ORGANISM: Artificial Sequence
<220> FEATURE:
<223> OTHER INFORMATION: Synthetic Probe

<400> SEQUENCE: 388
tcccagcaca catttagctc a                                         21

<210> SEQ ID NO 389
<211> LENGTH: 23
<212> TYPE: DNA
<213> ORGANISM: Artificial Sequence
<220> FEATURE:
<223> OTHER INFORMATION: Synthetic Probe

<400> SEQUENCE: 389
gtcagacccc gagggtcct cgc                                        23

<210> SEQ ID NO 390
<211> LENGTH: 25
<212> TYPE: DNA
<213> ORGANISM: Artificial Sequence
<220> FEATURE:
<223> OTHER INFORMATION: Synthetic Probe

<400> SEQUENCE: 390
aaggagctca gaagccctgc ccagc                                     25

<210> SEQ ID NO 391
<211> LENGTH: 20
<212> TYPE: DNA
<213> ORGANISM: Artificial Sequence
<220> FEATURE:
<223> OTHER INFORMATION: Synthetic Probe

<400> SEQUENCE: 391
ggcaaagaag gaacattcct                                           20

```
<210> SEQ ID NO 392
<211> LENGTH: 23
<212> TYPE: DNA
<213> ORGANISM: Artificial Sequence
<220> FEATURE:
<223> OTHER INFORMATION: Synthetic Probe

<400> SEQUENCE: 392
ccacctggca agaacaggcg ttc                                    23

<210> SEQ ID NO 393
<211> LENGTH: 21
<212> TYPE: DNA
<213> ORGANISM: Artificial Sequence
<220> FEATURE:
<223> OTHER INFORMATION: Synthetic Probe

<400> SEQUENCE: 393
agagggagac ccaggctcgg a                                      21

<210> SEQ ID NO 394
<211> LENGTH: 22
<212> TYPE: DNA
<213> ORGANISM: Artificial Sequence
<220> FEATURE:
<223> OTHER INFORMATION: Synthetic Probe

<400> SEQUENCE: 394
aagtcactga agggttttga gt                                     22

<210> SEQ ID NO 395
<211> LENGTH: 22
<212> TYPE: DNA
<213> ORGANISM: Artificial Sequence
<220> FEATURE:
<223> OTHER INFORMATION: Synthetic Probe

<400> SEQUENCE: 395
gccaccttca aatgggaagt ct                                     22

<210> SEQ ID NO 396
<211> LENGTH: 23
<212> TYPE: DNA
<213> ORGANISM: Artificial Sequence
<220> FEATURE:
<223> OTHER INFORMATION: Synthetic Probe

<400> SEQUENCE: 396
actcagaagg acaagtagag ttt                                    23

<210> SEQ ID NO 397
<211> LENGTH: 24
<212> TYPE: DNA
<213> ORGANISM: Artificial Sequence
<220> FEATURE:
<223> OTHER INFORMATION: Synthetic Probe

<400> SEQUENCE: 397
actgggcaca aacatgtcca ggtc                                   24

<210> SEQ ID NO 398
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 398
atttctatat ctatctccat                                              20

<210> SEQ ID NO 399
<211> LENGTH: 21
<212> TYPE: DNA
<213> ORGANISM: Artificial Sequence
<220> FEATURE:
<223> OTHER INFORMATION: Synthetic Probe

<400> SEQUENCE: 399
aggtaagcgc tgttgctagc c                                            21

<210> SEQ ID NO 400
<211> LENGTH: 21
<212> TYPE: DNA
<213> ORGANISM: Artificial Sequence
<220> FEATURE:
<223> OTHER INFORMATION: Synthetic Probe

<400> SEQUENCE: 400
gctccaacct cagcagactg t                                            21

<210> SEQ ID NO 401
<211> LENGTH: 23
<212> TYPE: DNA
<213> ORGANISM: Artificial Sequence
<220> FEATURE:
<223> OTHER INFORMATION: Synthetic Probe

<400> SEQUENCE: 401
acccaacagc ccctgcaagg gat                                          23

<210> SEQ ID NO 402
<211> LENGTH: 22
<212> TYPE: DNA
<213> ORGANISM: Artificial Sequence
<220> FEATURE:
<223> OTHER INFORMATION: Synthetic Probe

<400> SEQUENCE: 402
tgaacacaag gtactggtac ta                                           22

<210> SEQ ID NO 403
<211> LENGTH: 22
<212> TYPE: DNA
<213> ORGANISM: Artificial Sequence
<220> FEATURE:
<223> OTHER INFORMATION: Synthetic Probe

<400> SEQUENCE: 403
aggactatag aactttcccc ct                                           22

<210> SEQ ID NO 404
<211> LENGTH: 19
<212> TYPE: DNA
<213> ORGANISM: Artificial Sequence
<220> FEATURE:
<223> OTHER INFORMATION: Synthetic Probe

<400> SEQUENCE: 404
aagacatttt cagacagct                                               19

<210> SEQ ID NO 405
<211> LENGTH: 22
```

```
<212> TYPE: DNA
<213> ORGANISM: Artificial Sequence
<220> FEATURE:
<223> OTHER INFORMATION: Synthetic Probe

<400> SEQUENCE: 405
tcctcttttc ttagagactc ac                                              22

<210> SEQ ID NO 406
<211> LENGTH: 20
<212> TYPE: DNA
<213> ORGANISM: Artificial Sequence
<220> FEATURE:
<223> OTHER INFORMATION: Synthetic Probe

<400> SEQUENCE: 406
cgactgccac tcttactaga                                                 20

<210> SEQ ID NO 407
<211> LENGTH: 22
<212> TYPE: DNA
<213> ORGANISM: Artificial Sequence
<220> FEATURE:
<223> OTHER INFORMATION: Synthetic Probe

<400> SEQUENCE: 407
gctgggctta cgttgggaga ac                                              22

<210> SEQ ID NO 408
<211> LENGTH: 22
<212> TYPE: DNA
<213> ORGANISM: Artificial Sequence
<220> FEATURE:
<223> OTHER INFORMATION: Synthetic Probe

<400> SEQUENCE: 408
accttccctg gtacagaata ct                                              22

<210> SEQ ID NO 409
<211> LENGTH: 21
<212> TYPE: DNA
<213> ORGANISM: Artificial Sequence
<220> FEATURE:
<223> OTHER INFORMATION: Synthetic Probe

<400> SEQUENCE: 409
gctgaggtct gggccaggtc t                                               21

<210> SEQ ID NO 410
<211> LENGTH: 19
<212> TYPE: DNA
<213> ORGANISM: Artificial Sequence
<220> FEATURE:
<223> OTHER INFORMATION: Synthetic Probe

<400> SEQUENCE: 410
tcccacagga agcagacac                                                  19

<210> SEQ ID NO 411
<211> LENGTH: 23
<212> TYPE: DNA
<213> ORGANISM: Artificial Sequence
<220> FEATURE:
<223> OTHER INFORMATION: Synthetic Probe

<400> SEQUENCE: 411
```
tttattgtgg tagatactat tag                                              23

<210> SEQ ID NO 412
<211> LENGTH: 22
<212> TYPE: DNA
<213> ORGANISM: Artificial Sequence
<220> FEATURE:
<223> OTHER INFORMATION: Synthetic Probe

<400> SEQUENCE: 412
gtccaaagtt ggggtgctgg tt                                               22

<210> SEQ ID NO 413
<211> LENGTH: 23
<212> TYPE: DNA
<213> ORGANISM: Artificial Sequence
<220> FEATURE:
<223> OTHER INFORMATION: Synthetic Probe

<400> SEQUENCE: 413
ggacattgtt tcagtgccca agt                                              23

<210> SEQ ID NO 414
<211> LENGTH: 24
<212> TYPE: DNA
<213> ORGANISM: Artificial Sequence
<220> FEATURE:
<223> OTHER INFORMATION: Synthetic Probe

<400> SEQUENCE: 414
ctgcgggcgg gacgagcaag caca                                             24

<210> SEQ ID NO 415
<211> LENGTH: 24
<212> TYPE: DNA
<213> ORGANISM: Artificial Sequence
<220> FEATURE:
<223> OTHER INFORMATION: Synthetic Probe

<400> SEQUENCE: 415
acgcagagcc cgaaagcccc cagt                                             24

<210> SEQ ID NO 416
<211> LENGTH: 25
<212> TYPE: DNA
<213> ORGANISM: Artificial Sequence
<220> FEATURE:
<223> OTHER INFORMATION: Synthetic Probe

<400> SEQUENCE: 416
aggccgccac ccgcccgcga tccct                                            25

<210> SEQ ID NO 417
<211> LENGTH: 23
<212> TYPE: DNA
<213> ORGANISM: Artificial Sequence
<220> FEATURE:
<223> OTHER INFORMATION: Synthetic Probe

<400> SEQUENCE: 417
acagcgctcg caaccgcagc gat                                              23

<210> SEQ ID NO 418
<211> LENGTH: 21
<212> TYPE: DNA
<213> ORGANISM: Artificial Sequence

```
<220> FEATURE:
<223> OTHER INFORMATION: Synthetic Probe

<400> SEQUENCE: 418
agaggcaggt tcctggatca t                                           21

<210> SEQ ID NO 419
<211> LENGTH: 24
<212> TYPE: DNA
<213> ORGANISM: Artificial Sequence
<220> FEATURE:
<223> OTHER INFORMATION: Synthetic Probe

<400> SEQUENCE: 419
gaggtgactc tatcctatgt cttt                                        24

<210> SEQ ID NO 420
<211> LENGTH: 22
<212> TYPE: DNA
<213> ORGANISM: Artificial Sequence
<220> FEATURE:
<223> OTHER INFORMATION: Synthetic Probe

<400> SEQUENCE: 420
caagacacat ttggagaggg ac                                          22

<210> SEQ ID NO 421
<211> LENGTH: 22
<212> TYPE: DNA
<213> ORGANISM: Artificial Sequence
<220> FEATURE:
<223> OTHER INFORMATION: Synthetic Probe

<400> SEQUENCE: 421
ctacctgagc tagcatacaa gt                                          22

<210> SEQ ID NO 422
<211> LENGTH: 19
<212> TYPE: DNA
<213> ORGANISM: Artificial Sequence
<220> FEATURE:
<223> OTHER INFORMATION: Synthetic Probe

<400> SEQUENCE: 422
gctctaagaa agccacact                                              19

<210> SEQ ID NO 423
<211> LENGTH: 19
<212> TYPE: DNA
<213> ORGANISM: Artificial Sequence
<220> FEATURE:
<223> OTHER INFORMATION: Synthetic Probe

<400> SEQUENCE: 423
tcagcagtac cagcctaga                                              19

<210> SEQ ID NO 424
<211> LENGTH: 19
<212> TYPE: DNA
<213> ORGANISM: Artificial Sequence
<220> FEATURE:
<223> OTHER INFORMATION: Synthetic Probe

<400> SEQUENCE: 424
gcctcagagg cagctgctt                                              19
```

<210> SEQ ID NO 425
<211> LENGTH: 21
<212> TYPE: DNA
<213> ORGANISM: Artificial Sequence
<220> FEATURE:
<223> OTHER INFORMATION: Synthetic Probe

<400> SEQUENCE: 425
gaaggaagtg agtgcagcca c                                              21

<210> SEQ ID NO 426
<211> LENGTH: 19
<212> TYPE: DNA
<213> ORGANISM: Artificial Sequence
<220> FEATURE:
<223> OTHER INFORMATION: Synthetic Probe

<400> SEQUENCE: 426
accagtgccc tgcacactt                                                 19

<210> SEQ ID NO 427
<211> LENGTH: 22
<212> TYPE: DNA
<213> ORGANISM: Artificial Sequence
<220> FEATURE:
<223> OTHER INFORMATION: Synthetic Probe

<400> SEQUENCE: 427
gactcttgaa caacacaggt tt                                             22

<210> SEQ ID NO 428
<211> LENGTH: 21
<212> TYPE: DNA
<213> ORGANISM: Artificial Sequence
<220> FEATURE:
<223> OTHER INFORMATION: Synthetic Probe

<400> SEQUENCE: 428
gtcctgagag cgctgcctcc t                                              21

<210> SEQ ID NO 429
<211> LENGTH: 22
<212> TYPE: DNA
<213> ORGANISM: Artificial Sequence
<220> FEATURE:
<223> OTHER INFORMATION: Synthetic Probe

<400> SEQUENCE: 429
caaaagtcaa gcttatccta aa                                             22

<210> SEQ ID NO 430
<211> LENGTH: 23
<212> TYPE: DNA
<213> ORGANISM: Artificial Sequence
<220> FEATURE:
<223> OTHER INFORMATION: Synthetic Probe

<400> SEQUENCE: 430
tgcacaaccc tagtggcgcc att                                            23

<210> SEQ ID NO 431
<211> LENGTH: 21
<212> TYPE: DNA
<213> ORGANISM: Artificial Sequence
<220> FEATURE:
<223> OTHER INFORMATION: Synthetic Probe

```
<400> SEQUENCE: 431
gttcagtaga gattgtttca a                                              21

<210> SEQ ID NO 432
<211> LENGTH: 22
<212> TYPE: DNA
<213> ORGANISM: Artificial Sequence
<220> FEATURE:
<223> OTHER INFORMATION: Synthetic Probe

<400> SEQUENCE: 432
gcacatgttc tgcggcccac ca                                             22

<210> SEQ ID NO 433
<211> LENGTH: 22
<212> TYPE: DNA
<213> ORGANISM: Artificial Sequence
<220> FEATURE:
<223> OTHER INFORMATION: Synthetic Probe

<400> SEQUENCE: 433
aaagaggtta accatgtatt at                                             22

<210> SEQ ID NO 434
<211> LENGTH: 21
<212> TYPE: DNA
<213> ORGANISM: Artificial Sequence
<220> FEATURE:
<223> OTHER INFORMATION: Synthetic Probe

<400> SEQUENCE: 434
agaggttgac tgtataatat t                                              21

<210> SEQ ID NO 435
<211> LENGTH: 23
<212> TYPE: DNA
<213> ORGANISM: Artificial Sequence
<220> FEATURE:
<223> OTHER INFORMATION: Synthetic Probe

<400> SEQUENCE: 435
cctagagagg gtgagaacct gcc                                            23

<210> SEQ ID NO 436
<211> LENGTH: 25
<212> TYPE: DNA
<213> ORGANISM: Artificial Sequence
<220> FEATURE:
<223> OTHER INFORMATION: Synthetic Probe

<400> SEQUENCE: 436
accaacggac ctacttccct ccgcc                                          25

<210> SEQ ID NO 437
<211> LENGTH: 22
<212> TYPE: DNA
<213> ORGANISM: Artificial Sequence
<220> FEATURE:
<223> OTHER INFORMATION: Synthetic Probe

<400> SEQUENCE: 437
tggggaccct ccctgaacca ag                                             22

<210> SEQ ID NO 438
```

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 438
caactccgat atgcaatggg ta                                                  22

<210> SEQ ID NO 439
<211> LENGTH: 24
<212> TYPE: DNA
<213> ORGANISM: Artificial Sequence
<220> FEATURE:
<223> OTHER INFORMATION: Synthetic Probe

<400> SEQUENCE: 439
acgcgcaggc cagagaccca ggca                                                24

<210> SEQ ID NO 440
<211> LENGTH: 21
<212> TYPE: DNA
<213> ORGANISM: Artificial Sequence
<220> FEATURE:
<223> OTHER INFORMATION: Synthetic Probe

<400> SEQUENCE: 440
ctgctgggcc acaacgtggg a                                                   21

<210> SEQ ID NO 441
<211> LENGTH: 22
<212> TYPE: DNA
<213> ORGANISM: Artificial Sequence
<220> FEATURE:
<223> OTHER INFORMATION: Synthetic Probe

<400> SEQUENCE: 441
gcggtcccgc ggcgccccgc ct                                                  22

<210> SEQ ID NO 442
<211> LENGTH: 22
<212> TYPE: DNA
<213> ORGANISM: Artificial Sequence
<220> FEATURE:
<223> OTHER INFORMATION: Synthetic Probe

<400> SEQUENCE: 442
caacaaaatc actagtcttc ca                                                  22

<210> SEQ ID NO 443
<211> LENGTH: 23
<212> TYPE: DNA
<213> ORGANISM: Artificial Sequence
<220> FEATURE:
<223> OTHER INFORMATION: Synthetic Probe

<400> SEQUENCE: 443
tcatacagct agataaccaa aga                                                 23

<210> SEQ ID NO 444
<211> LENGTH: 21
<212> TYPE: DNA
<213> ORGANISM: Artificial Sequence
<220> FEATURE:
<223> OTHER INFORMATION: Synthetic Probe

<400> SEQUENCE: 444
```
actttcggtt atctagcttt a                                    21

<210> SEQ ID NO 445
<211> LENGTH: 21
<212> TYPE: DNA
<213> ORGANISM: Artificial Sequence
<220> FEATURE:
<223> OTHER INFORMATION: Synthetic Probe

<400> SEQUENCE: 445
caggccggga caagtgcaat a                                    21

<210> SEQ ID NO 446
<211> LENGTH: 22
<212> TYPE: DNA
<213> ORGANISM: Artificial Sequence
<220> FEATURE:
<223> OTHER INFORMATION: Synthetic Probe

<400> SEQUENCE: 446
ctacctgcac gaacagcact tt                                   22

<210> SEQ ID NO 447
<211> LENGTH: 22
<212> TYPE: DNA
<213> ORGANISM: Artificial Sequence
<220> FEATURE:
<223> OTHER INFORMATION: Synthetic Probe

<400> SEQUENCE: 447
tgctcaataa atacccgttg aa                                   22

<210> SEQ ID NO 448
<211> LENGTH: 22
<212> TYPE: DNA
<213> ORGANISM: Artificial Sequence
<220> FEATURE:
<223> OTHER INFORMATION: Synthetic Probe

<400> SEQUENCE: 448
gcaaaaatgt gctagtgcca aa                                   22

<210> SEQ ID NO 449
<211> LENGTH: 22
<212> TYPE: DNA
<213> ORGANISM: Artificial Sequence
<220> FEATURE:
<223> OTHER INFORMATION: Synthetic Probe

<400> SEQUENCE: 449
aacaatacaa cttactacct ca                                   22

<210> SEQ ID NO 450
<211> LENGTH: 22
<212> TYPE: DNA
<213> ORGANISM: Artificial Sequence
<220> FEATURE:
<223> OTHER INFORMATION: Synthetic Probe

<400> SEQUENCE: 450
cacaagatcg gatctacggg tt                                   22

<210> SEQ ID NO 451
<211> LENGTH: 22
<212> TYPE: DNA

```
<213> ORGANISM: Artificial Sequence
<220> FEATURE:
<223> OTHER INFORMATION: Synthetic Probe

<400> SEQUENCE: 451
cgcaaggtcg gttctacggg tg                                      22
```